United States Patent
Wittekind et al.

(10) Patent No.: US 9,718,875 B2
(45) Date of Patent: *Aug. 1, 2017

(54) COMPOSITION AND METHODS BASED ON NEUTRALIZING ANTIBODIES DELIVERED INTRANASALLY FOR ENHANCED THERAPEUTIC EFFICACY

(71) Applicant: ContraFect Corporation, Yonkers, NY (US)

(72) Inventors: Michael Wittekind, Yonkers, NY (US); Adam Vigil, Yonkers, NY (US)

(73) Assignee: ContraFect Corporation, Yonkers, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/268,091

(22) Filed: Sep. 16, 2016

(65) Prior Publication Data

US 2017/0002062 A1 Jan. 5, 2017

Related U.S. Application Data

(63) Continuation of application No. 14/769,795, filed as application No. PCT/US2014/027939 on Mar. 14, 2014.

(60) Provisional application No. 61/782,661, filed on Mar. 14, 2013.

(51) Int. Cl.
| | |
|---|---|
| *C12N 7/00* | (2006.01) |
| *C07K 16/10* | (2006.01) |
| *A61K 9/00* | (2006.01) |
| *A61K 39/42* | (2006.01) |
| *A61K 45/06* | (2006.01) |
| *A61K 39/00* | (2006.01) |

(52) U.S. Cl.
CPC ......... *C07K 16/1018* (2013.01); *A61K 9/007* (2013.01); *A61K 9/0043* (2013.01); *A61K 39/42* (2013.01); *A61K 45/06* (2013.01); *A61K 2039/505* (2013.01); *A61K 2039/507* (2013.01); *A61K 2039/543* (2013.01); *A61K 2039/544* (2013.01); *A61K 2039/545* (2013.01); *C07K 2317/21* (2013.01); *C07K 2317/24* (2013.01); *C07K 2317/33* (2013.01); *C07K 2317/52* (2013.01); *C07K 2317/54* (2013.01); *C07K 2317/55* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,625,015 A | 11/1986 | Green et al. | |
| 6,235,708 B1 | 5/2001 | Holloway et al. | |
| 7,262,270 B2 | 8/2007 | Weissenhorn et al. | |
| 7,696,330 B2 | 4/2010 | Meulen et al. | |
| 8,288,090 B2* | 10/2012 | Fomsgaard | A61K 39/145 424/202.1 |
| 2003/0100096 A1 | 5/2003 | Holloway | |
| 2009/0203538 A1 | 8/2009 | Sugioka et al. | |
| 2009/0311183 A1 | 12/2009 | Devy et al. | |
| 2009/0311265 A1 | 12/2009 | Van Den Brink et al. | |
| 2010/0086555 A1 | 4/2010 | Lanzavecchia | |
| 2011/0319600 A1 | 12/2011 | Kuta et al. | |
| 2012/0039899 A1 | 2/2012 | Olsen et al. | |
| 2012/0128671 A1 | 5/2012 | Horowitz et al. | |
| 2016/0083456 A1* | 3/2016 | Wittekind | C07K 16/1018 424/147.1 |

FOREIGN PATENT DOCUMENTS

| | | |
|---|---|---|
| JP | 62175426 A | 8/1987 |
| WO | 2003080672 A1 | 10/2003 |
| WO | 2004/080403 A2 | 9/2004 |
| WO | 2007/134327 A2 | 11/2007 |
| WO | 2008/028946 A2 | 3/2008 |
| WO | 2008/110937 A2 | 9/2008 |
| WO | 2009/053604 A2 | 4/2009 |
| WO | 2009/079259 A2 | 6/2009 |
| WO | 2009/121004 A2 | 10/2009 |
| WO | 2010/010466 A2 | 1/2010 |
| WO | 2010/010467 A2 | 1/2010 |
| WO | 2010/022120 A1 | 2/2010 |
| WO | 2010/027818 A2 | 3/2010 |
| WO | 2010/074656 A1 | 7/2010 |
| WO | 2010/130636 A1 | 11/2010 |

(Continued)

OTHER PUBLICATIONS

Ye et al. Intranasal Delivery of an IgA Monoclonal Antibody Effective against Sublethal H5N1 Influenza Virus Infection in Mice. Clinical and Vaccine Immunology, Sep. 2010, p. 1363-1370.*
Carragher et al. A Novel Role for Non-Neutralizing Antibodies against Nucleoprotein in Facilitating Resistance to Influenza Virus. J Immunol 2008; 181:4168-4176.*
Bianchi et al., "Universal influenza B vaccine based on the maturational cleavage site of the hemagglutinin pecursor," J Virol (2005) 79(12):7380-7388BIANCHI et al., "Universal influenza B vaccine based on the maturational cleavage site of the hemagglutinin precursor," J Virol (2005) 79(12):7380-7388.
Bright; et al., "Cross-clade protective immune responses to influenza viruses with H5N1 HA and NA elicited by an influenza virus-like particle", PLoS One (Jan. 30, 2008), 3(1):e1501.
Corti et al., "A Neutralizing Antibody Selected from Plasma Cells That Binds to Group 1 and Group 2 Influenza A Hemagglutinins", Science (2011) 333:850-856.

(Continued)

*Primary Examiner* — Michelle S Horning
(74) *Attorney, Agent, or Firm* — Hueschen and Sage

(57) ABSTRACT

The present invention provides methods for treatment or prophylaxis of viruses, particularly influenza virus, by administration of agents, particularly neutralizing antibodies or active fragments thereof, directly to the respiratory tract, including by intranasal or inhalation administration. The invention provides compositions suitable for intranasal or inhalation treatment and administration. The invention includes methods for treatment or prophylaxis combining intranasal or inhalation administration with intraperitoneal or intravenous administration of antibodies.

16 Claims, 41 Drawing Sheets

(56) References Cited

FOREIGN PATENT DOCUMENTS

| WO | 2011/117848 A1 | 9/2011 |
|----|----------------|--------|
| WO | 2011/126370 A1 | 10/2011 |
| WO | 2011/160083 A1 | 12/2011 |
| WO | 2012/045001 A2 | 4/2012 |
| WO | 2013/007770 A1 | 1/2013 |
| WO | 2013/114885 A1 | 8/2013 |
| WO | 2013/132007 A1 | 9/2013 |
| WO | 2014152841 A1 | 9/2014 |

OTHER PUBLICATIONS

Donis et al., "Distinct Lineages of Influenza Virus H4 Hemagglutinin Genes in Different ReQions of the World", Virology (1989) 169:408-417.
Doyle; et al., "A monoclonal antibody targeting a highly conserved epitope in influenza B neuraminidase provides protection against drug resistant strains", Biochemical and Biophysical Research Communications (Nov. 2013), 441 (1):226-229.
Dreyfus et al., "Highly conserved protective epitopes on influenza B viruses," Science (2012) 337(6100):1343-1348.
Ekiert et al., "A highly conserved neutralizing epitope on group 2 influenza A viruses," Science (2011) 333(6044):843-850.
Ekiert et al., "Antibody Recognition of a Highly Conserved Influenza Virus Epitope", Science (2009) 324:246-251.
European Search Report dated Aug. 7, 2015, by the European Patent Office for European Patent Application No. 12854682.7, 8 pages.
Grandea et al., "Human antibodies reveal a protective epitope that is highly conserved among human and nonhuman influenza A viruses," Proc Natl Acad Sci USA (2010) 107(28):12658-12663.
International Preliminary Report on Patentability and Written Opinion for PCT/US2012/068037, issued Jun. 10, 2014, 8 pages.
International Search Report and Written Opinion mailed Aug. 11, 2015, from the European Patent Office, for International Patent Application No. PCT/US2015/014521 (filed Feb. 4, 2015), 17 pages.
International Search Report and Written Opinion mailed Jun. 12, 2013, from the International Searching Authority, for International Patent Application No. PCT/US12/68037 (filed Dec. 5, 2012), 14 pages.
International Search Report and Written Opinion mailed Nov. 25, 2011, from the International Searching Authority, for International Patent Application No. PCT/US11/40982 (filed Jun. 17, 2011), 11 pages.
International Search Report and Written Opinion mailed Aug. 28, 2014, from the International Searching Authority, for International Patent Application No. PCT/US14/27939 (filed Mar. 14, 2014), 14 pages.
International Search Report by the International Searching Authority mailed Aug. 28, 2014, for International Application No. PCT/US14/27939 (filed Mar. 14, 2014), 3 pages.
Krause et al: 11A Broadly Neutralizing Human Monoclonal Antibody That Recognizes a Conserved, Novel Epitope on the Globular Head of the Influenza HINI Virus Hemagglutinin, Journal of Virology, vol. 85, No. 20, Oct. 15, 2011 (Oct. 15, 2011), pp. 10905-10908, XP055044176, ISSN: 0022-538X, DOI: 10.1128/JVI.00700-11.
Kostolansky et al., "Antibody Response to Hidden Epitope of Influenza A Haemagglutinin Elicited by Anti-Idiotypic Antibodies", Acta vifologica (1994) 38:215-222.
Kuboto-Koketsu; et al., "Broad neutralizing human monoclonal antibodies against influenza virus from vaccinated healthy donors", Biochem Biophys Res Commun (Sep. 11, 2009), 387(1):180-5.
McCutcheon; et al., "Multiplexed screening of natural humoral immunity identifies antibodies at fine specificity for complex and dynamic viral targets", MABS (Jan. 8, 2014), 6(2):460-473.
Prabhu et al., "Monoclonal Antibodies against the Fusion Peptide of Hemagglutinin Protect Mice from Lethal Influenza A Virus H5N1 Infection", Journal of Virology (2009) 83(6):2553-2562.
Steel; et al., "Influenza virus vaccine based on the conserved hemagglutinin stalk domain", Mbio (Apr. 2010), 1(1):1-9.
Sui et al., "Structural and functional bases for broad-spectrum neutralization of avian and human influenza A viruses," Nat Struct Mol Biol (2009) 16(3):265-273.
Sui; et al., "Wide Prevalence of Heterosubtypic Broadly Neutralizing Human Anti-Influenza A Antibodies", Clinical Infectious Diseases (Apr. 15, 2011), 52(8):1003-1009.
Supplementary European Search Report for EP 11796555.8, mailed Oct. 22, 2013, 17 pages.
Throsby et al., "Heterosubtypic neutralizing monoclonal antibodies cross-protective against H5N1 and H1 N1 recovered from human IgM+ memory B cells," PLoS One (2008) 3(12):e3942.
Usinger; et al., "Human monoclonal antibody 53 shows unique cross-clade neutralization of influenza", American Society of Viraology (Jul. 16-20, 2011), Abstract only.
Wagner; et al., "Bispecific antibody generated with sortase and click chemistry has broad antiinfluenza virus activity", Proceedings of the National Academy of Sciences (Nov. 10, 2014), 111(47):16820-16825.
Wang; et al., "Broadly Protective Monoclonal Antibodies against H3 Influenz Viruses following Sequential Immunization with Different Hemagglutinins", PLoS (Feb. 2010), 6(2):e1000796.
Weltzin R et al: 11 Intranasal Antibody Prophylaxis for Protection Against Viral Disease, Clinical Microbiology Reviews, Washington, DC, US, vol. 12, No. 3, Jul. 1, 1999 (Jul. 1, 1999), pp. 383-393, XP000911981, ISSN: 0893-8512.
Yasugi; et al., "Human monoclonal antibodies broadly neutralizing against influenza B virus", PLoS Pathogens (Feb. 2013), 9(2):1-12.
Yoshida et al., "Cross-protective potential of a novel monoclonal antibody directed against antigenic site B of the hemagglutinin of influenza A viruses," PLoS Pathog (2009) 5(3):e1000350.
Zanin; et al., "An Anti-H5N1 Influenza Virus FcDart Antibody is a Highly Efficacious Therapeutic Agent and Prophylactic against H5N1 Influenza Virus Infection", Journal of Virology (Feb. 11, 2015), 89(8):4549-4561.
Ziegler et al., "Type- and Subtype-Specific Detection of influenza Viruses in Clinical Specimens by Rapid Culture Assay", Journal of Clinical Microbiology (1995) 33(2):318-321.
Abrahamson, M. et al. "Identification of the Probable Inhibitory Reactive Sites of the Cysteine Proteinase Inhibitors Human Cystatin C and Chicken Cystatin." The Journal of Biological Chemistry, 1987, vol. 262, No. 20, pp. 9688-9694.
Mottet et al. "Characterization of Sendai virus M protein mutants that can partially interfere with virus particle production." Journal of Virology, 1999, vol. 80, p. 2977-2986.
Schoofs et al. "Epitopes of an influenza viral peptide recognized by antibody at single amino acid resolution." Journal of Immunology, 1988, vol. 140 p. 611-616.
Song, G. et al. "Progesterone and Interferon Regulate Cystatin C in the Endometrium." Endocrinology, 2006, vol. 147, pp. 3478-3483.
Rudikoff et al. "Single amino acid substitution altering antigen-binding specificity." PNAS, vol. 79, p. 1979-83, Mar. 1982 (Mar. 1982).
Tamura et al. "Structural Correlates of an Anticarcinoma Antibody: Identification of Specificity-Determining Residues (SDRs) and Development of a Minimally Immunogenic Antibody Variant by Retention of SDRs Only." J Immunol., vol. 164, p. 1432-41, Feb. 2000 (Feb. 2000).

* cited by examiner

COMPOSITION AND METHODS BASED ON NEUTRALIZING ANTIBODIES DELIVERED INTRANASALLY FOR ENHANCED THERAPEUTIC EFFICACY

FIELD OF THE INVENTION

The present invention relates generally to methods for treatment or prophylaxis of respiratory infectious agents, particularly viruses, particularly influenza virus, by administration of agents, particularly antibodies or active fragments thereof, particularly neutralizing antibodies, directly to the respiratory tract, including by intranasal or inhalation administration. The invention relates to compositions suitable for intranasal or inhalation treatment and administration and protocol and methods for treatment or prophylaxis via intranasal or inhalation administration of antibody(ies) or combining intranasal or inhalation administration with intraperitoneal or intravenous administration of antibodies.

BACKGROUND OF THE INVENTION

Influenza is a leading cause of death and illness and affects the upper and lower respiratory tracts. Influenza virus causes a highly infectious respiratory illness that results in over 200,000 hospitalizations and 36,000 casualties in the US during severe seasons. Globally, 20% of children and 5% of adults develop symptomatic influenza every year (Nicholson, K. G. et al (2003) Lancet 362:1733-1745). Morbidity and mortality varies due to the virulence of the influenza strain and the host's exposure history, age, and immune status. In addition to seasonal epidemics, pandemic influenza strains emerge with some regularity. Due to the lack of pre-existing immunity against the major viral antigens, pandemic influenza can spread quickly, often with more severe disease than seasonal influenza (Swartz, K. A. & Luby, J. P. (2007) Tex Med 103: 31-34). For example, the 1918-1919 "Spanish Flu" pandemic strain was the most deadly plague of the 20th century, infecting 32% of the global population and leading to over 20 million deaths (Webster, R. G. (1999) Proc Natl Acad Sci USA 96:1164-1166). Recently, the 2009 H1N1 virus spread to 61 million people in the U.S., leading to an estimated 274,000 hospitalizations from April 2009-April 2010 (Lagace-Wiens, P. R. et al (2010) Crit Care Med 38:e1-9). This pandemic shut down schools and commercial establishments due to uncertainty how to respond to the threat.

There are three types of influenza viruses, influenza A, B and C. Human influenza A and B viruses cause seasonal epidemics of disease. Influenza type C infections cause a mild respiratory illness and are not thought to cause epidemics. Influenza A viruses are divided into subtypes based on two proteins on the surface of the virus: the hemagglutinin (H) and the neuraminidase (N). There are 17 different hemagglutinin subtypes and 10 different neuraminidase subtypes. Influenza A viruses can be further broken down into different strains. Current subtypes of influenza A viruses found in people are influenza A (H1N1) and influenza A (H3N2) viruses. Influenza B viruses are not divided into subtypes, but can be further broken down into two different lineages. Influenza A (H1N1), A (H3N2), and influenza B viruses are included in each year's influenza vaccine.

Five kinds of clinically relevant influenza viruses are circulating in the human population at the present time, three of influenza A and also two of influenza B. Influenza A type virus is divided into two distinct phylogenetic groups 1 and 2. Group 1 includes hemagglutinin subtypes H1, H2, H5, H6, H8, H9, H11, H13 and H16. Group 2 includes H3, H4, H7, H10, H15 and H14. Currently relevant circulating influenza A viruses of group 1 are of subtype H1, which is further divided into those of human and swine origin, and group 2 relevant circulating viruses are presently of subtype H3. Influenza A viruses are responsible for the bulk of seasonal disease, with H3 viruses dominating eight of the past twelve influenza seasons in the United States (CDC Seasonal flu; United States Surveillance Data). In 1968, an H3 virus caused one of the three major influenza pandemics of the twentieth century and H3 viruses have persisted since that time as a significant agent of human disease. In addition to humans, H3 influenza viruses commonly infect birds, swine, and horses. Influenza B viruses have been circulating in humans for more than 100 years, with current strains divided into two lineages, the Yamagata lineage and Victoria lineage. Recently the trivalent influenza vaccine has expanded to a quadrivalent vaccine covering both lineages of influenza B, as well as an H1 virus and H3 virus.

Current treatments for influenza are not adequate and can be ineffective. Despite widespread vaccination, susceptibility to influenza remains. The factors contributing to susceptibility include (1) incomplete vaccination coverage such as with the 2009 H1N1 pandemic, when vaccine shortages were widespread, (2) years such as 2008 when the vaccine formulation poorly represented the strains in circulation, (3) reduced efficacy of vaccination in the elderly, as the average efficacy ranges from 40-50% at age 65, and only 15-30% past age 70, and (4) the emergence of pandemic strains not represented in seasonal vaccines. Further, drug resistance against the anti-viral therapeutics currently available for the treatment of influenza has become a serious problem. Resistance to adamantanes (amantidine and rimantadine), drugs that act on the M2 protein and inhibit viral fusion, increased from 1.9% in 2004 to 14.5% during the first 6 months of the 2004-2005 flu season, and currently has surpassed 90% (Sheu, T. G. et al (2011) J Infect Dis 203:13-17). Resistance to Tamiflu, an antiviral drug that inhibits the influenza neuraminidase protein, dramatically increased from 1-2% of H1N1 viruses during the 2006-2007 flu season, to 12% by 2007-2008, and exceeded 99% of the seasonal H1N1 viruses in 2009. Fortunately, the pandemic H1N1 strain of 2009 was sensitive to Tamiflu and likely resulted in fewer deaths during the pandemic. As such there is an overwhelming need for new influenza therapeutics.

The development of therapeutic antibodies for influenza is gaining attention as conserved epitopes within the hemagglutinin (HA) molecule have recently been discovered. There have been several reports of the isolation and characterization of human monoclonal antibodies (MAb) capable of recognizing and neutralizing a diverse number of influenza A virus subtypes. Many of these are targeted to the hemagglutinin (HA) glycoprotein, which elicits the most robust neutralizing antibodies during vaccination or natural infection. HA is composed of two subunits HA1 and HA2 which are critical components in virus infection. HA1 is involved in attachment to the host cell receptor sialic acid and HA2 mediates fusion of viral and endosome membranes. MAb CR6261 is a well characterized antibody that binds to H1 viruses and other subtypes (H5) within group 1 and binds on the HA2 subunit (Throsby M et al (2008) PLoS ONE 3:e3942; Eckert D C et al (2009) Science 324:246-251; Friesen R H E et al (2010) PLoS ONE 5(2):e1906; U.S. Pat. No. 8,192,927). MAb CR8020 binds to the membrane-proximal region of HA2 on both H3 and another subtype (H7) viruses which are group 2 viruses (Eckert D C et al (2011) Science 333:843-850). The antibody FI6v3 from researchers in Switzerland can bind to an epitope present on both group 1 (H1) and 2 (H3) viruses, however FI6 has shown limited efficacy in mice (Corti D et al (2011) Science 333:850-856). Palese and colleagues have reported broadly protective monoclonal antibodies against H3 influenza viruses using sequential immunization in mice with different hemagglutinins (Wang T T et al (2010) PLoS Pathog 6(2): e1000796; US Application 20110027270). Using this approach, a broadly reactive H1 antibody was isolated (Tan G S et al (2012) J Virol 86(11):6179-6188).

Currently, the usual antibody therapy doses are well-established to be multiple mg/kg per dose, based on research and clinical experience to date with numerous recombinant antibodies, including the over twenty monoclonal antibodies that have been clinically approved in the United States (Newsome B W and Ernstoff M S (2008) Br J Clin Pharmacol 66(1):6-19). For example, panitumumab, an anti-EGFR fully human antibody approved for colorectal cancer, is administered intravenously at 6 mg/kg over 1-1½ hours every 2 weeks. Using an average human weight of 70 kg, this amounts to 420 mg of antibody per dose.

No monoclonal antibody has yet been clinically approved for influenza. Reports of studies with influenza antibodies in animals demonstrate that the effective dose range of these antibodies when given intravenously or intraperitoneally for therapeutic or prophylactic purposes require ranges from 1 mg/kg up to 100 mg/kg. Phase I clinical trials in the US with some of these antibodies (CR6261, CR8020, TCN-032) use a dose escalation in safety and tolerance studies from 2 mg/kg up to 50 mg/kg (clinicaltrials.gov; NCT01390025, NCT01406418, NCT01756950). This large amount of material presents a major hurdle in the development of this new line of antibody therapeutics. Specifically, systemic doses in this range results in a significant cost of material and also time and personnel costs involved in infusions. As such there is an imperative need to either increase efficacy and/or reduce the amount of material needed for antibody therapy or prophylaxis against influenza to be a viable alternative.

The citation of references herein shall not be construed as an admission that such is prior art to the present invention.

SUMMARY OF THE INVENTION

The invention provides a novel method and means for effective treatment and prophylaxis of viral infections, particularly including influenza virus, by administration of neutralizing antibody(ies) directly to the respiratory tract or airways, including by intranasal or inhalation administration. The invention demonstrates that direct delivery of neutralizing antibody to the respiratory tract, including by inhalation (IH) and/or intranasal (IN) delivery and administration, is superior, more efficacious and effective at lower doses than systemic administration (IV or IP) of the same antibody in the same amounts. Treatment or prophylaxis with IN or IH delivered antibody before or even after virus exposure or infection is effective.

The invention provides inhalation or intranasal compositions effective for treatment or prophylaxis of viral infection in a mammal comprising one or more virus neutralizing monoclonal antibody. In a first aspect, the invention provides inhalation or intranasal compositions effective for treatment or prophylaxis of viral infection in a mammal comprising a virus neutralizing monoclonal antibody in a single unit dose of 1 mg/kg or less. The invention provides inhalation or intranasal compositions effective for treatment or prophylaxis of viral infection in a mammal comprising one or more virus neutralizing monoclonal antibody in a single unit dose of 10 mg/kg or less. The invention provides inhalation or intranasal compositions effective for treatment or prophylaxis of viral infection in a mammal comprising one or more virus neutralizing monoclonal antibody in a single unit dose of less than 1 mg/kg. The invention provides inhalation or intranasal compositions effective for treatment or prophylaxis of viral infection in a mammal comprising a virus neutralizing monoclonal antibody in a single unit dose of less than 0.5 mg/kg. The invention provides inhalation or intranasal compositions effective for treatment or prophylaxis of viral infection in a mammal comprising a virus neutralizing monoclonal antibody in a single unit dose of less than 0.1 mg/kg.

In a particular aspect, the invention provides inhalation or intranasal compositions effective for treatment or prophylaxis of influenza virus, including influenza virus infection, in a mammal comprising one or more influenza virus neutralizing monoclonal antibody. In a further aspect, the invention provides inhalation or intranasal compositions effective for treatment, prophylaxis or reduction of transmission of influenza virus in a mammal comprising a combination of influenza neutralizing antibodies directed against circulating influenza virus strains. In an aspect the invention provides compositions for intranasal administration consisting of a combination of influenza neutralizing antibodies directed against circulating influenza virus strains, particularly consisting of an influenza A anti-H1 antibody, an influenza A anti-H3 antibody and an anti-influenza B antibody. In one aspect, the composition includes an influenza A antibody effective against or further effective against other influenza strains, including but not limited to H2, H5, and H7 strains.

The compositions are suitable and applicable for use and for treatment or prophylaxis of influenza virus. In a particular aspect, the compositions are suitable for reducing transmission of a respiratory virus. The compositions are suitable for reducing transmission of influenza virus.

In an aspect, the composition(s) comprise a virus neutralizing monoclonal antibody in a single unit dose of 0.5 mg/kg or less. In an aspect, the composition(s) comprise a virus neutralizing monoclonal antibody in a single unit dose of 0.1 mg/kg or less. In a further aspect, the composition(s) comprise a virus neutralizing monoclonal antibody in a single unit dose of 0.05 mg/kg or less.

In an aspect, the composition(s) comprise a virus neutralizing monoclonal antibody in a single unit dose of less than 0.5 mg/kg. In an aspect, the composition(s) comprise a virus neutralizing monoclonal antibody in a single unit dose of less than 0.1 mg/kg. In a further aspect, the composition(s) comprise a virus neutralizing monoclonal antibody in a single unit dose of less than 0.05 mg/kg.

In an exemplary aspect the compositions may comprise one or more virus neutralizing antibody which is an influenza virus neutralizing antibody. The composition may particularly comprise one or more influenza virus neutralizing antibody directed against influenza A, particularly against influenza A Group 1 and/or influenza A Group 2. The composition may particularly comprise one or more influenza virus neutralizing antibody directed against influenza B, particularly against Yamagata lineage and/or Victoria lineage. The composition may comprise one or more influenza virus antibody directed against influenza A virus, particularly against Group 1 and Group 2 influenza A virus, including H1 virus and/or H3 virus, and/or against influenza B virus, including Yamagata lineage and/or Victoria lineage. In a particular aspect, the composition may comprise one or more influenza virus antibody directed against influenza A virus, particularly against Group 1 and Group 2 influenza A virus, including H1 virus and/or H3 virus, and one or more influenza antibody against influenza B virus, including Yamagata lineage and/or Victoria lineage. The composition may comprise a combination of antibodies comprising one or more antibody directed against influenza A virus, particularly against Group 1 and Group 2 influenza A virus, including H1 virus and/or H3 virus, and one or more influenza antibody against influenza B virus.

In accordance with the invention, including as exemplified in the studies provided herein, numerous and various neutralizing antibodies have enhanced efficacy at lower doses when administered to the airway or respiratory tract, such as by intranasal or inhalation administration. Thus, a composition of the invention may comprise a neutralizing antibody or fragment thereof, including a Fab fragment, which is capable of neutralizing influenza virus and which may be directed against influenza A and/or influenza B virus. A composition of the invention may comprise one or more influenza virus neutralizing antibody selected from CR6261, CR8020, CR9114, 6F12, GG3, 5A7, Mab53 and Mab579, fragments thereof, synthetic or recombinant derivatives thereof, humanized or chimerized versions thereof, and antibodies having the heavy and light chain CDRs thereof.

The composition may particularly comprise influenza neutralizing antibody 6F12, fragments thereof, synthetic or recombinant derivatives thereof, humanized or chimerized versions thereof, and antibodies having the heavy and light chain CDRs thereof. The composition may particularly comprise influenza neutralizing antibody GG3, fragments thereof, synthetic or recombinant derivatives thereof, humanized or chimerized versions thereof, and antibodies having the heavy and light chain CDRs thereof. The composition may particularly comprise influenza neutralizing antibody 5A7, fragments thereof, synthetic or recombinant derivatives thereof, humanized or chimerized versions thereof, and antibodies having the heavy and light chain CDRs thereof. The composition may particularly comprise influenza neutralizing antibody Mab53, fragments thereof, synthetic or recombinant derivatives thereof, humanized or chimerized versions thereof, and antibodies having the heavy and light chain CDRs thereof. The composition may particularly comprise influenza neutralizing antibody Mab579, fragments thereof, synthetic or recombinant derivatives thereof, humanized or chimerized versions thereof, and antibodies having the heavy and light chain CDRs thereof.

The composition may particularly comprise one or more influenza virus neutralizing antibody directed against influenza A, particularly against influenza A Group 1 and/or influenza A Group 2. In an exemplary aspect, a composition may comprise one or more influenza virus neutralizing antibody directed against influenza A, particularly against influenza A Group 1, particularly against H1 virus subtype, wherein one or more antibody is selected from CR6261 or CA6261, 6F12, GG3, mAb53, or active fragments thereof. The composition may comprise one or more influenza virus neutralizing antibody directed against influenza A, particularly against influenza A Group 2, particularly against H3 virus subtype, wherein one or more antibody is selected from CR8020 or CA8020, mAb579, or active fragments thereof. In an aspect, the composition may comprise influenza virus neutralizing antibody CR9114 or CA9114, or active fragments thereof, said antibody providing an influenza virus neutralizing antibody against influenza A and/or against influenza B. The composition may comprise one or more influenza virus neutralizing antibody directed against influenza B, particularly against Yamagata lineage and/or Victoria lineage, wherein one or more antibody is selected from 5A7, CR9114, CA9114, or active fragments thereof.

The virus neutralizing antibody may particularly be an antibody fragment capable of neutralization. In an aspect, the antibody fragment lacks the Fc and/or lacks or has reduced effector function. The antibody fragment may be selected from Fab, Fab', and F(ab')$_2$. The virus neutralizing antibody or fragment may be derived from recombinant protein, may be recombinantly expressed, including as an active fragment, or may be derived or generated by other means or methods, including means or methods to provide neutralizing antibody or fragment(s) within the airway or respiratory tract, including by way of genetic material or DNA or DNA vector expression, such as by delivering DNA or RNA encoding neutralizing antibody or fragment(s) thereof.

A composition of the invention may further comprise a pharmaceutically acceptable excipient, carrier or diluent. The composition may comprise an excipient, carrier, diluents or additive suitable or appropriate for nasal or pulmonary delivery and for intranasal or inhalation administration. The composition may comprise an excipient, carrier, diluents or additive suitable or appropriate to stimulate or enhance immunological response and/or antibody-mediated cellular or system effects. The composition may comprise an immunological mediator or stimulator of the immune response.

The invention provides methods for treatment, prophylaxis or reduction or inhibition of transmission of virus, particularly respiratory virus, particularly influenza virus. The invention provides a method for treatment or prophylaxis of viral infection in a mammal exposed to, having contracted, or suffering from a respiratory virus comprising administering intranasally (IN) or via inhalation to said mammal one or more monoclonal antibody capable of neutralizing the respiratory virus.

In an aspect of the method, the monoclonal antibody is an IgG antibody. In an aspect of the method, the respiratory virus is influenza virus. The respiratory virus may be an influenza A or B type virus, or of unknown or undetermined type. In an aspect, the antibody is a neutralizing antibody capable of neutralizing and directed against influenza A or B. In an aspect, the antibody is a combination of monoclonal antibodies capable of neutralizing and directed against influenza A and B viruses.

In accordance with the method, the antibody can be administered post infection or after presumed infection, exposure or manifestation of clinical symptoms. In an aspect thereof, the antibody can be administered in a time period up to 8 hours post infection. Alternatively, the antibody is administered in a time period up to 24 hours post infection. In a further alternative, the antibody is administered in a time period up to 48 hours post infection. In a still further alternative, the antibody is administered in a time period up to 72 hours post infection. Antibody may be administered, including as a single dose or in multiple sequential doses, up to 8 hours post infection (8 hpi), 12 hpi, 18 hpi, 24 hpi, 36 hpi, 48 hpi, 72 hpi, 1 day post infection, 2 days post infection, 3 days post infection, 4 days post infection, 5 days post infection, 6 days post infection 7 days post infection, a week post infection, 10 days post infection, 2 weeks post infection, 3 weeks post infection, 4 weeks post infection, a month post infection, months post infection.

The antibody may be administered in a single dose. The single dose may be of less than 10 mg/kg body weight, of less than 5 mg/kg body weight, of less than 2 mg/kg body weight, of 1 mg/kg body weight or less. The single dose may be of less than 1 mg/kg body weight, of less than 0.5 mg/kg, of less than 0.1 mg/kg, of less than 0.05 mg/kg. The antibody may be administered in multiple doses. The doses may be the same each dose or may vary in each dose, or may be an initial higher dose, followed by lower doses. The single dose or doses or any dose may be of less than 1 mg/kg body weight, of less than 0.5 mg/kg, of less than 0.1 mg/kg, of less than 0.05 mg/kg. The initial dose may be greater than 1 mg/kg and further or subsequent doses may be lower or may be less than 1 mg/kg.

Antibody may be administered to the airways or respiratory tract in multiple doses of less than 1 mg/kg per dose. Antibody may be administered intranasally or via inhalation in multiple doses of less than 1 mg/kg per dose. In such an aspect, the multiple doses may be administered at least 2 hours apart and up to 72 hours or later after presumed infection, exposure or manifestation of clinical symptoms. Thus the antibody doses may be administered minutes or hours or days apart. The antibody doses may be administered post infection or post presumed infection or exposure hours or days apart. The antibody doses may be administered post infection or post presumed infection or exposure and up to 2, 4, 6, 8, 12, 24, 36, 48 or 72 hours after.

The administration protocol or method of the invention may particularly comprise a first administration of antibody to the airway or respiratory tract, particularly by inhalation or intranasal administration of antibody, combined with or followed by a second or one or more additional administration(s) which is or are not via the inhalation or intranasal route, for example systemic delivery, such as IP or IV administration(s). Thus the method may comprise additional administration IP or IV of a virus specific monoclonal antibody wherein the antibody additionally administered is a neutralizing or non-neutralizing antibody. The antibody additionally administered IP or IV may be the same antibody as administered IN or via inhalation or may be a different or altered antibody as administered IN or via inhalation. The antibody additionally administered, for example via IP or IV, may be administered simultaneously, sequentially, or subsequently to the IN or inhalation administered antibody. Any such subsequent administration may be hours later and may be 2, 4, 6, 8, 12 or up to 24 hours later. Subsequent administration may be days later and may be 1 day, 2 days, or 3 days later. Subsequent administration may be days later and may be up to 7 days later, a week later, or weeks later. Subsequent administration may be in a single dose or multiple doses hours and/or days and/or weeks later.

In a further aspect, the invention provides a protocol for administration of monoclonal antibody against respiratory virus, particularly influenza virus, comprising administering a first intranasal or inhalation dose of neutralizing antibody and subsequently or simultaneously administering a second dose, or one or more additional dose(s), of antibody which is not administered to the respiratory tract, and may be administered intraperitoneally or intravenously, wherein the antibody of the second dose or additional dose(s) is the same or a different antibody as antibody of the first dose. The antibody of the second dose or additional dose(s) may be an altered or modified antibody which is altered or modified to be more effective or efficacious IV or IP. In an aspect, the antibody of the first dose may lack effector function, such as an Fab antibody, and the antibody of the second dose may have effector function, have Fc, or may be modified to have enhanced effector function.

The protocol may include multiple doses of antibody via the inhalation or intranasal route and may include multiple doses of the same or an alternative antibody via the IP or IV route. In an aspect of the protocol, the subject or patient being administered antibody may be monitored, such as for clinical manifestation of disease or viral infection, and the dose or doses may be altered, reduced or enhanced or administered closer or further apart depending on the status of the patient or subject and of the infection or illness.

In an aspect of the protocol, the respiratory virus may be influenza virus, and may be influenza A or influenza B or an unknown or undetermined influenza virus. The antibody of the second dose, which is not administered to the respiratory tract, may be a neutralizing or a non-neutralizing antibody, and may have effector function or enhanced effector function.

In an aspect of the protocol, the first intranasal or inhalation dose may less than 1 mg/kg, less than 0.5 mg/kg, less than 0.1 mg/kg. The second or additional IP or IV dose is particularly administered at a higher dose than the first intranasal or inhalation dose. The second or additional IP or IV dose is particularly administered at a dose at least 10 fold higher of amount of antibody than the first intranasal or inhalation dose. The second or additional IP or IV dose may be at least 1 mg/kg, at least 5 mg/kg, at least 10 mg/kg, at least 15 mg/kg, or greater than 10 mg/kg, or greater than 20 mg/kg, or greater than 50 mg/kg.

In a further aspect of the protocol, the first intranasal or inhalation dose may be less than 1 mg/kg and the second IP or IV dose at least 10 fold higher in mg/kg than the first intranasal dose. In a further aspect of the protocol, the first intranasal or inhalation dose may be less than 1 mg/kg and the second IP or IV dose at least 50 fold higher in mg/kg than the first intranasal dose. In an additional aspect, the first intranasal or inhalation dose may be less than 0.5 mg/kg and the second IP or IV dose at least 5 mg/kg.

The first intranasal or inhalation dose may be less than 1 mg/kg and administered within 24 hours after presumed infection, exposure or manifestation of clinical symptoms. The first intranasal or inhalation dose may be less than 1 mg/kg and administered within 48 hours after presumed infection, exposure or manifestation of clinical symptoms. The first intranasal or inhalation dose may be less than 1 mg/kg and administered within 72 hours after presumed infection, exposure or manifestation of clinical symptoms.

Another aspect of the invention is a method for inhibiting transmission of respiratory virus comprising administering intranasally or via inhalation to a subject exposed to, at risk of exposure to or showing clinical signs of infection with a respiratory virus a virus neutralizing antibody in a single unit dose of 1 mg/kg or less. The single unit dose may be less than 10 mg/kg or less than 1 mg/kg. The single unit dose of the method may be less than 0.5 mg/kg or less than 0.1 mg/kg or less than 0.05 mg/kg.

The virus may particularly be influenza virus, may be influenza A or B virus or an unknown or undetermined influenza virus, and the antibody an IgG antibody.

The virus neutralizing antibody of the above method may be administered within 48 hours after presumed infection, exposure or manifestation of clinical symptoms. The virus neutralizing antibody may be administered within 24 hours after presumed infection, exposure or manifestation of clinical symptoms. The virus neutralizing antibody may be administered within 12 hours after presumed infection, exposure or manifestation of clinical symptoms. The virus neutralizing antibody may be administered more than 24 hours and within 72 hours after presumed infection, exposure or manifestation of clinical symptoms. The virus neutralizing antibody may be administered upon or after initial manifestation of clinical symptoms.

In accordance with the method for inhibiting transmission, the antibody may be administered at a dose of less than 0.5 mg/kg, at a dose of less than 0.1 mg/kg, at a dose of less than 0.05 mg/kg.

Other objects and advantages will become apparent to those skilled in the art from a review of the following description which proceeds with reference to the following illustrative drawings.

BRIEF DESCRIPTION OF THE DRAWINGS

FIG. 21 provides studies in mice with influenza B virus (B/Florida) to assess efficacy of a series of antibodies against influenza B. All antibodies were administered at 1 mg/kg IN 24 hpi with 10×LD50 of B virus. Antibodies tested were 43K16, 59G1, 112A22, 11G23, 114O22, CA9114 and 40J7 as indicated. PBS and no virus are shown as controls. Animals were monitored for body weight daily for 14 days post infection and percent body weight of original day 0 weight is plotted.

FIG. 23 provides animal efficacy studies with various influenza B antibodies administered 8 hpi with B/Malaysia virus. All antibodies were administered at 1 mg/kg 8 hpi with 10×LD50 virus. Antibodies tested were CA9114, 54H5, 110C16, 43K16, 59G1, 114G23, 43J23, 112A22, 58O8, 55K6, 114D22 and 40J7. PBS and no virus were controls. Animals were monitored for body weight daily for 14 days post infection and percent body weight of original day 0 weight is plotted.

FIG. 24 depicts animal efficacy studies using an antibody cocktail comprising an H1 antibody, an H3 antibody and an influenza B virus antibody. The cocktail of antibodies uses H1 antibody GG3, H3 antibody CA8020 and B antibody 43J23. In the cocktail, each of the antibodies is administered at 1 mg/kg in a single 50 μl volume dose IN at 24 hpi with 10×LD50 of B/Florida (Yamagata B virus). For comparison B antibody 43J23 was tested alone against B/Florida virus—1 mg/kg 43J23 administered IN 24 hpi. CA9114 antibody was administered IP at 1 mg/kg 24 hpi with B/Florida. PBS and no virus were used as controls. Animals were monitored for body weight daily for 14 days post infection and percent body weight of original day 0 weight is plotted.

FIG. 25 provides animal efficacy studies using an antibody cocktail of H1 antibody GG3, H3 antibody CA8020 and influenza B virus antibody 43J23. 1 mg/kg of each of the antibodies was administered IN 24 hours after infection (24 hpi) with B/Malaysia virus. For comparison, B antibody 43J23 was tested alone against B/Malaysia virus with 1 mg/kg 43J23 administered IN 24 hpi, and CA9114 antibody was administered IP at 1 mg/kg 24 hpi with B/Malaysia. PBS and no virus were used as controls. Animals were monitored for body weight daily for 14 days post infection and percent body weight of original day 0 weight is plotted.

DETAILED DESCRIPTION

Figure 1:
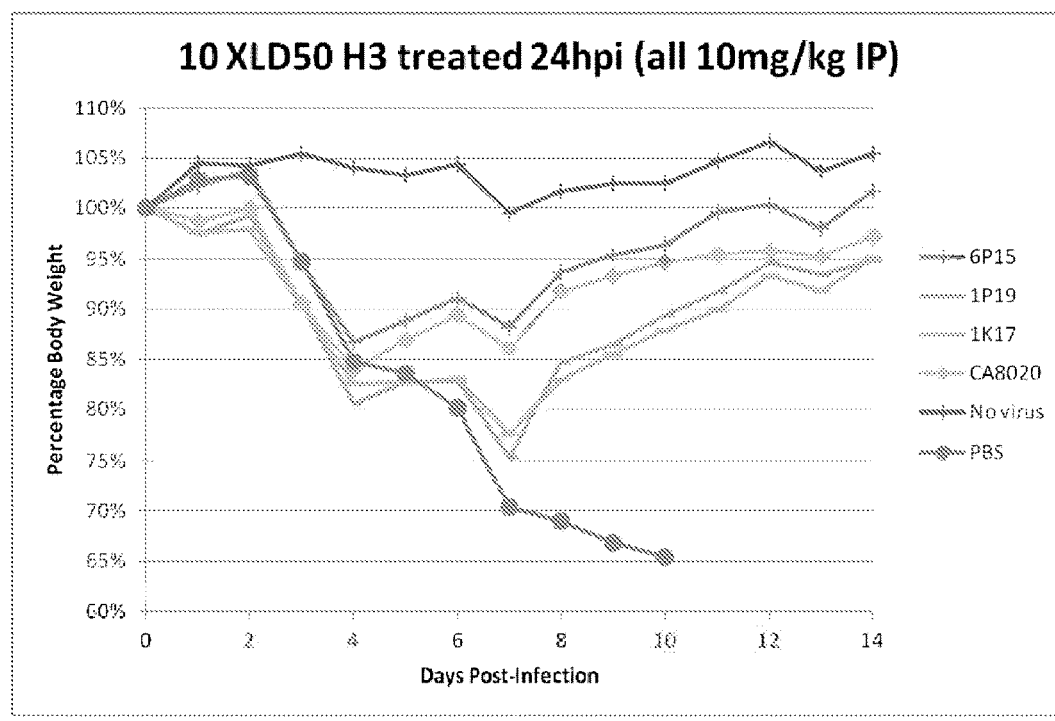
FIG. 1 Neutralizing and non-neutralizing MAbs are effective IP post-infection. Animals were inoculated with 10×LD50 of H3 influenza virus (mouse-adapted A/Victoria/361/2011, hereby referred to as Vic/11 MA) and treated 24 hours post infection (24 hpi) with 10 mg/kg IP of various noted antibodies—6P15, 1P19, 1K17 (all non-neutralizing) and CA8020 (neutralizing)—and PBS or no virus as control. Animals were monitored for body weight each day for 14 days post infection and percent body weight of original day 0 weight is plotted.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The antibodies used and referred to herein include those having the amino acid sequences as reported and publicly known and include antibodies, proteins, polypeptides having modifications to the known or public amino acid sequence and retaining or displaying substantially equivalent activity, including target neutralization or recognition and binding activity. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. The antibodies are intended to include within their scope proteins specifically recited herein as well as all substantially homologous analogs and allelic variations.

The following are examples of various groupings of amino acids: Amino acids with nonpolar R groups: Alanine, Valine, Leucine, Isoleucine, Proline, Phenylalanine, Tryptophan, Methionine; Amino acids with uncharged polar R groups: Glycine, Serine, Threonine, Cysteine, Tyrosine, Asparagine, Glutamine; Amino acids with charged polar R groups (negatively charged at Ph 6.0): Aspartic acid, Glutamic acid; Basic amino acids (positively charged at pH 6.0): Lysine, Arginine, Histidine (at pH 6.0); Another grouping may be those amino acids with phenyl groups: Phenylalanine, Tryptophan, Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces—turns in the protein's structure.

Two amino acid sequences are "substantially homologous" when at least about 70% of the amino acid residues (preferably at least about 80%, and most preferably at least about 90 or 95%) are identical, or represent conservative substitutions.

Nucleic acids encoding antibodies used in accordance with the application and of use in the invention may be used in preparation and/or production of antibodies or active fragments thereof of use in the invention. Vectors comprising such nucleic acids may be used in expression or isolation of antibodies as provided or of use herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease Si), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding antibodies of or of use in the invention which code for an antibody, polypeptide or active fragment thereof having the same amino acid sequence, but which are degenerate to the original or known encoding sequence. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCC or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in antibody or active fragment encoding sequences such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

As mentioned above, a DNA sequence encoding an antibody, polypeptide or active fragment thereof can be prepared synthetically rather than cloned. The DNA sequence can be designed with the appropriate codons for the antibody or fragment amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature,* 292:756 (1981); Nambair et al., *Science,* 223:1299 (1984); Jay et al., *J. Biol. Chem.,* 259: 6311 (1984). Synthetic DNA sequences allow convenient construction of genes which will express analogs or "muteins". Alternatively, DNA encoding muteins can be made by site-directed mutagenesis of native genes or cDNAs, and muteins can be made directly using conventional polypeptide synthesis.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20°C below the predicted or determined $T_m$ with washes of higher stringency, if desired.

In its primary aspect, the present invention concerns the identification of a novel method, protocol and means for effective treatment and prophylaxis of viral infections, particularly including influenza virus, by administration of neutralizing antibody to the airways or respiratory tract, such as by intranasal or inhalation administration of neutralizing antibody(ies). Intranasal or inhalation administration of neutralizing antbody(ies), particularly influenza virus neutralizing antibodies, is more effective to treat or block virus therapeutically or prophylactically than alternative means of administration, such as IP administration. In its primary aspect, the present invention concerns the identification of a novel method and means for effective treatment and prophylaxis of viral infections, particularly including influenza virus, by intranasal administration of neutralizing antibody(ies). Inhalation and/or intranasal delivery and administration is superior, more efficacious and effective at lower doses than systemic administration (IV or IP) of the same antibody in the same amounts. Treatment or prophylaxis with IN delivered antibody before or even after virus exposure or infection is effective.

Methods or protocols combining an intranasal dose of antibody with an IP dose of antibody are particularly effective therapeutically or prophylactically against virus, particularly influenza virus. Such methods or protocols include wherein one or more intranasal or inhalation dose of antibody is combined with one or more IP or IV dose of antibody. The intranasal or inhalation dose may be administered before, after, simultaneously or in sequence with the IP or IV dose. One or more intranasal, inhalation, IP or IV dose(s) may be administered. Intranasal administered antibody may be an antibody fragment lacking Fc or effector function, such as a Fab, whereas IP administered antibody may have effector function or enhanced effector function.

In accordance with the invention, neutralizing antibody is administered to the airways or respiratory tract for enhanced efficacy against virus, particularly influenza virus. Administration to the airways or respiratory tract may be by any recognized or known means and may include inhalation administration or intranasal administration. For enhanced effectiveness, the neutralizing antibody is delivered to one or more of the upper respiratory tract and the lower respiratory tract, and may include the nasal cavity, nose, sinus, throat, pharynx, larynx, trachea, bronchi and the lungs.

Inhalation refers to taking in, particularly in the context of taking in or administering/being administered an agent or compound, including an antibody or active fragment thereof, or a composition comprising such, whereby the agent, compound, antibody, fragment, including as comprised in the composition, is delivered to the respiratory tract. The respiratory tract may include the upper and, or, and/or lower respiratory tract. The upper respiratory tract comprises the nose, nasal cavity, sinuses, larynx, trachea. The lower respiratory tract comprises the lungs, airways (bronchi and bronchioles) and air sacs (alveoli). Inhalation may occur via the nose or via the mouth, or via direct administration to the lower respiratory tract as in intratracheal administration. Thus, inhalation may include nose only or primarily, intranasal, inhaling via the mouth, oral inhalation, intratracheal inhalation, intratracheal instillation. Thus inhalation provides for and contemplates any means of administration whereby drug, agent, composition, antibody, fragment, reaches or is deposited at or in the respiratory tract exclusively, specifically or preferentially, including the upper and/or lower respiratory tract.

The term intranasal as used herein includes, but is not limited to, administering, administration or occurring within or via the nose or nasal structures. The term intranasal as used herein and as exemplified as an embodiment in the examples in not intended to be limited to or to imply limitation to administration directly or specifically or solely via the nose or nasal cavity, particularly in serving to exclude other means of administration whereby drug, agent, antibody, fragment, composition is delivered or otherwise provided to, deposited in or at or otherwise distributed to the respiratory tract.

Devices for administration or delivery to the respiratory tract or airway(s) are known and recognized in the skilled art and in clinical or medical practice and are applicable in the methods, protocols and compositions of the present invention. Devices include the metered dose inhaler, metered spray pumps, hand-bulb atomizer, small or large volume nebulizers, ultrasonic nebulizer and dry powder inhaler.

The present invention has application and use in treatment or prophylaxis particularly of agents or pathogens which target, infect, or affect the respiratory tract. Thus, the present invention has application and use in treatment or prophylaxis of respiratory infections, particularly respiratory viruses, and of agents which are associated with or causally related to respiratory illness. Common viral respiratory diseases are illnesses caused by a variety of viruses that have similar traits and affect the upper respiratory tract. The viruses involved may be the influenza viruses, respiratory syncytial virus (RSV), parainfluenza viruses, and respiratory adenoviruses. Parainfluenza viruses are the major cause of croup in young children and can cause bronchitis, pneumonia, and bronchiolitis. Adenoviruses invade primarily the respiratory and gastrointestinal tracts, and the conjunctiva of the eyes. The adenoviruses can cause a variety of illnesses from pharyngitis to pneumonia, conjunctivitis, and diarrhea. Symptoms can appear from 1-10 days after exposure to the viruses.

Clinical administration of antibodies for treatment or alleviation of conditions (cancer, inflammatory conditions, antivirals, anti-infectives) has used systemic administration exclusively, and generally IV administration, which require large and costly amounts of antibody, assistance of medical personnel, and significant time for administration (typical IV dose is for 2 hours). While other means of administration, such as intranasal, may be mentioned, particularly in patents or applications covering these antibodies, intranasal administration is deemed an equivalent alternative at best, ignored entirely, or not pursued, perhaps because it is less understood, thought to be less attractive or less efficacious, and deemed to invoke the immunological system indirectly or less directly than IP or IV administration routes. However, the present invention and remarkable studies provided herein demonstrate that intranasal administration is indeed a preferred and more efficacious alternative, particularly for neutralizing antibodies. In particular, neutralizing antibodies that can act intranasally at the site or location of initial pathogen insult or exposure are more effective than alternative modes of administration.

Thus in accordance with the present invention, intranasal delivery of antibodies provides a marked and significant improvement in efficacy compared to systemic routes such as IV or IP routes. Furthermore, enhanced intranasal efficacy is demonstrated by antibodies that are neutralizing. Nonneutralizing antibodies, particularly antibodies which do not demonstrate direct inhibition or blocking of respiratory agents or viruses, particularly influenza virus, using accepted or known assays of neutralization or virus blocking, exhibit impaired efficacy when delivered intranasally versus systemic or IP administration. The present studies demonstrate that intranasal (IN) delivery of neutralizing antibodies can dramatically increase therapeutic and prophylactic efficacy by more than 10 fold compared to intraperitoneal (IP) or intravenous (IV) route of delivery, using an accepted and known influenza mouse model. Comparable efficacy can be achieved using less than one tenth of the same dose when given IN instead of by IV or IP routes. Neutralizing antibodies administered intranasally can dramatically increase therapeutic efficacy by orders of magnitude. Neutralizing antibodies administered intranasally can dramatically increase therapeutic efficacy by minimally 10 to 100 fold. Neutralizing antibodies administered intranasally can dramatically increase therapeutic efficacy by at least 10 fold, at least 50 fold, more than 10 fold, more than 50 fold, more than 100 fold, up to 100 fold, compared to intraperitoneal (IP) administration of the same antibody under similar conditions. Intranasal administration of neutralizing antibodies provides a novel and unexpected approach to prophylaxis and treatment of infection, particularly including influenza infection. IN administration can now be implemented effectively and combined with other forms of administration to provide more effective and less costly approaches to treatment and prophylaxis.

Antibody mediated neutralization of virus as defined or accepted in the art and as referred to and utilized herein can be tested in various assays. Examples of neutralization assays include conventional neutralization assays based on the inhibition of a virus cytopathic effect (CPE) on cells in culture. For example, influenza neutralization may be tested by reducing or blocking formation of CPE in MDCK cells infected with influenza. Virus and neutralizing agent may be premixed before addition to cells, followed by measuring blocking of virus entry. Hemagglutinin inhibition (HI) may be tested in vitro and can detect the blocking of a viruses ability to bind to red blood cells. An exemplary known and accepted neutralization assay is provided in the WHO Manual on Animal Influenza (who/cds/csr/ncs/2002.5, pages 48-54). Antibodies that block the sialic acid receptor binding site will neutralize virus binding to cells, thereby blocking infection. Conversely neutralization assays can detect blocking of virus egress, as in the case of neuraminidase inhibitors like Tamiflu. Recently, neutralizing antibodies have been identified that function in a similar manner by preventing viral egress, this example of neutralization includes the CR9114 antibody on influenza B viruses (Dreyfus et al (2012) Science 337:1343-1348). Also, microneutralization assays are utilized wherein virus nucleoprotein (NP) is detected in infected cells using microtiter plates in combination with ELISA. Quantitative PCR assays have been described to measure viral proteins (Dreyfus C et al (2012) Emerging Inf Diseases 19(10:1685-1687).

A nonneutralizing antibody is an antibody that fails to demonstrate any direct interaction or binding with the virus or the target of a virus on the cell it infects may be interpreted as nonneutralizing. Nonneutralizing antibodies may bind to virus but do not neutralize or inhibit the virus or viral replication in any above-noted or recognized neutralizing assay. Nonneutralizing antibodies may bind to conserved proteins or epitopes on proteins in a virus. For example the M2 antibody in clinical trials TCN-032 can bind to a broad range of influenza A viruses, but does not demonstrate neutralization in conventional neutralization assays. Similarly, antibodies that do not neutralize can be identified that bind to HA.

We have identified nonneutralizing, but broadly reactive antibodies to HA. These include antibodies 6P15, 1P19, and 1K17 that were negative in neutralization assays including, CPE inhibition, HI, microneutralization and plaque reduction assay. As demonstrated in the examples herein, these antibodies do not exhibit improved therapeutic efficacy with intranasal administration versus intraperitoneal administration.

In an aspect of the invention, a virus binding antibody or binding fragment thereof, particularly wherein the antibody or fragment is neutralizing, may be combined with agents or drugs to form an antibody-drug or antibody-agent conjugate for respiratory tract or airway administration, including inhalation or intranasal administration, for use in the invention. The drug or agent combined with or conjugated to the antibody or fragment may be a virus neutralizing drug or agent.

In a particular and further aspect, combined or serial administration of neutralizing antibody IN, along with administration of antibody IP or IV, provides an effective and enhanced synergistic means for treatment and/or prophylaxis of virus infection. The antibody administered systemically, including IP or IV, may be neutralizing or non-neutralizing, and thereby may be the same antibody as administered IN, or may be a modified antibody, or a distinct antibody. Thus, the antibody for intranasal delivery, a neutralizing antibody, may be a distinct or different antibody from the antibody used in combination therewith for delivery via another means, particularly systemic delivery including IP or IV delivery.

The present invention demonstrates that Fc function and Fc portions of neutralizing antibodies, thus effector function, is not required for intranasal enhanced efficacy. Thus, antibodies and fragments such as Fab fragments, or antibodies lacking Fc or lacking effector function, are effective intranasally. In contrast, Fab fragments of antibodies (neutralizing or non-neutralizing), or antibodies lacking Fc or lacking effector function, are not effective IP or IV.

Antibodies

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Preferred antibodies are of the IgG class. Also included within the meaning of the term "antibody" are any "antibody fragment".

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. A monoclonal antibody is an antibody having one species of antibody combining site capable of immunoreacting with a particular antigen. A monoclonal antibody thus typically displays a single binding affinity for any antigen with which it immunoreacts. In contrast to polyclonal antibody preparations, which typically include different antibodies directed against different determinants (epitopes), each monoclonal antibody of a monoclonal antibody preparation is directed against a single determinant on an antigen. A monoclonal antibody may be multiply specific if it contains an antibody molecule having a plurality of antibody combining sites, each immunospecific for a different antigen; e.g., a bispecific (chimeric) monoclonal antibody. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "antibody fragment" refers to a molecule other than an intact antibody that comprises a portion of an intact antibody that binds the antigen to which the intact antibody binds. Examples of antibody fragments include but are not limited to Fv, Fab', Fab'-SH, F(ab')$_2$; diabodies; linear antibodies; single-chain antibody molecules (e.g. scFv); and multispecific antibodies formed from antibody fragments. In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies. An "antibody fragment" includes a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); (xii) a minibody, which is a bivalent molecule comprised of scFv fused to constant immunoglobulin domains, CH3 or CH4, wherein the constant CH3 or CH4 domains serve as dimerization domains (Olafsen T et al (2004) Prot Eng Des Sel 17(4): 315-323; Hollinger P and Hudson PJ (2005) Nature Biotech 23(9):1126-1136); and (xiii) other non-full length portions of heavy and/or light chains, or mutants, variants, or derivatives thereof, alone or in any combination. Single chain Fabs (scFAb) are known and described including in US20070274985.

As antibodies can be modified in a number of ways, the term "antibody" should be construed as covering any specific binding member or substance having a binding domain with the required specificity, and neutralization capability where applicable in accordance herewith. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

As used herein, "Fab fragment" refers to an antibody fragment comprising a light chain fragment comprising a VL domain and a constant domain of a light chain (CL), and a VH domain and a first constant domain (CH1) of a heavy chain. Fab and F(ab')$_2$ portions of antibody molecules may be prepared by the proteolytic reaction of papain and pepsin, respectively, on substantially intact antibody molecules by methods that are well-known or may be prepared synthetically or recombinantly. Fab' antibody molecule portions are also well-known and may be produced from F(ab')$_2$ portions followed by reduction of the disulfide bonds linking the two heavy chain portions as with mercaptoethanol, and followed by alkylation of the resulting protein mercaptan with a reagent such as iodoacetamide.

The term "Fc domain" herein is used to define a C-terminal region of an immunoglobulin heavy chain that contains at least a portion of the constant region. For example in natural antibodies, the Fc domain is composed of two identical protein fragments, derived from the second and third constant domains of the antibody's two heavy chains in IgG, IgA and IgD isotypes; IgM and IgE Fc domains contain three heavy chain constant domains (C.sub.H domains 2-4) in each polypeptide chain.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

In certain instances as taught in the present invention, some level or amount of neutralizing activity is required and a necessary feature of an antibody for use, particularly for intranasal or inhalation administration. Therefore, any fragment, variant, derivative, synthetic or antibody portion for use intranasally in accordance with the present invention need retain neutralization capability and activity against target virus or pathogen, in an aspect influenza virus. On the other hand, an antibody that will be administered via alternative systemic routes, including intraperitoneally or intravenously must bind or recognize target virus or pathogen, in an aspect influenza virus, however, neutralization is not required. Thus, as an example, Fab fragments of antibody(ies), which retain neutralization, may be utilized intranasally. Effector functions, mediated via Fc are not required for intranasally efficacy and neutralization. Conversely, systemically delivered antibodies will mediate their efficacy significantly through effector function.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6.sup.th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. Antibodies may be sufficiently defined in amino acid sequence in accordance with their heavy and light chain CDRs, and may particularly be described and characterized in accordance with their heavy chain variable region CDR1, CDR2, and CDR3 sequences and their light chain variable region CDR1, CDR2, and CDR3 sequences. An antibody may be defined or characterized as an antibody or fragment comprising a heavy and light chain, wherein the heavy chain variable region comprises specific CDR1, CDR2, and CDR3 sequences and the light chain variable region comprises specific CDR1, CDR2, and CDR3 sequences. CDR and FR regions of an antibody may be determined in accordance with standard methods and analyses available and known to one of skill in the art. Thus, CDR and FR regions may be determined according to the standard definition of Kabat et al., Sequences of Proteins of Immunological Interest, 5th ed., Public Health Service, National Institutes of Health, Bethesda, Md. (1991), or in accordance with the International ImmunoGeneTics information system (IMGT) (imgt.org; LeFranc, M-P (1999) Nucl Acids Res 27:209-212; LeFranc, M-P (2005) Nucl Acids Res 33:D539-D579).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

Methods and methodology for making monoclonal antibodies by hybridomas or other means and approaches is well known. Panels of monoclonal antibodies produced against pathogen, viral or influenza peptides can be screened for various properties; i.e., neutralization, isotype, epitope, affinity, etc. Of particular interest are monoclonal antibodies that neutralize the activity of the virus or its subunits. Such monoclonals can be readily identified in neutralization activity assays. High affinity antibodies are also useful for effective binding and/or neutralization or when immunoaffinity purification of native or recombinant virus is desired or of interest.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-viral antibodies are also well-known in the art. See Niman et al., *Proc. Natl. Acad. Sci. USA,* 80:4949-4953 (1983). Typically, the virus, viral protein, or a peptide analog is used either alone or conjugated to an immunogenic carrier, as the immunogen for producing monoclonal antibodies. The hybridomas are screened for the ability to produce an antibody that immunoreacts with the virus, protein or peptide analog.

Antibodies may also be bispecific, for example wherein one binding domain of the antibody is a viral neutralizing antibody of use the invention, and the other binding domain has a different specificity, e.g. to bind or associate with apical surface of cells, to bind airway epithelial cells etc. Bispecific antibodies of the present invention include wherein one binding domain of the antibody is a neutralizer of use in the present invention, including a fragment thereof, and the other binding domain is a distinct antibody or fragment thereof, including that of a distinct anti-viral specific antibody, including an alternative neutralizing antibody or a non-neutralizing antibody. The other binding domain may be an antibody that recognizes or targets a particular cell type, as in a lung epithelial, alveolar macrophage, neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine or a toxin (e.g., ricin) or anti-mitotic or apoptotic agent or factor. Thus, the antibodies of the invention may be utilized to direct or target agents, labels, other molecules or compounds or antibodies in indications such as infection, inflammation, etc.

Bispecific antibodies of use in the invention may comprise at least two Fab fragments, in one example wherein either the variable regions or the constant regions of the heavy and light chain of the second Fab fragment are exchanged. Due to the exchange of either the variable regions or the constant regions, said second Fab fragment is also referred to as "cross-Fab fragment" or "xFab fragment" or "crossover Fab fragment". Such bispecifics are described in US2013006011.

Immunoconjugates or antibody fusion proteins of the present invention, wherein the antibodies, antibody molecules, or fragments thereof, of use in the present invention are conjugated or attached to other molecules or agents further include, but are not limited to such antibodies, molecules, or fragments conjugated to a chemical ablation agent, toxin, immunomodulator, cytokine, cytotoxic agent, chemotherapeutic agent, antiviral agent, antimicrobial agent or peptide, cell wall and/or cell membrane disrupter, or drug. In an aspect, the immunoconjugates or antibody fusions may include antibodies, molecules, or fragments conjugated to an antiviral agent, particularly and anti-influenza agent. An anti-influenza agent may be a neuraminidase inhibitor. The anti-influenza agent may be selected from Tamiflu and Relenza. An anti-influenza agent may be an M2 inhibitor, such as amantadine or rimantadine. An anti-influenza agent may be a viral replication inhibitor.

Any such anti-influenza agents may also be compounded or combined as part of the compositions provided herein or administered in conjunction with or separately to the antibodies or active fragments hereof. The anti-influenza agents may be administered via the same or alternative means (such as via inhalation or via oral (e.g. pills) means) as the antibodies or fragments thereof or the inhalation or intranasal compositions of the invention. Thus, the antibodies of the present invention and the inhalation or intranasal compositions of the invention may further comprise or may be administered in combination with or sequentially to or before an anti-influenza agent or antiviral agent, such as for instance a neuraminidase inhibitor, including an agent selected from Tamiflu and Relenza. Numerous antibodies have been characterized and are in development as therapeutic antibodies for influenza, including based on conserved epitopes of the virus. Some cross-reactive antibodies target the hemagglutinin (HA) glycoprotein, which elicits the most robust neutralizing antibodies during vaccination or natural infection. HA is composed of two subunits HA1 and HA2 which are critical components in virus infection. MAb CR6261 is a well characterized antibody that binds to H1 viruses and other subtypes (H5) within group 1 and binds on the HA2 subunit (Throsby M et al (2008) PL0S ONE 3:e3942; Eckert D C et al (2009) Science 324:246-251; Friesen R H E et al (2010) PLoS ONE 5(2):e1906; U.S. Pat. No. 8,192,927). MAb CR8020 binds to the membrane-proximal region of HA2 on both H3 and another subtype (H7) viruses which are group 2 viruses (Eckert D C et al (2011) Science 333:843-850). The antibody FI6v3 from researchers in Switzerland can bind to an epitope present on both group 1 (H1) and 2 (H3) viruses, however FI6 has shown limited efficacy in mice (Corti D et al (2011) Science 333:850-856). Palese and colleagues have reported broadly protective monoclonal antibodies against H3 influenza viruses using sequential immunization in mice with different hemagglutinins (Wang T T et al (2010) PLoS Pathog 6(2): e1000796; US Application 20110027270). Using this approach, a broadly reactive H1 antibody was isolated (Tan G S et al (2012) J Virol 86(11):6179-6188).

A listing of various known influenza antibodies is provided in TABLE 1 below. Exemplary studies evaluating various antibodies in TABLE I in the methods and compositions of the invention, particularly for enhanced efficacy via intranasal or inhalation administration, are provided herein. Known antibodies, including as listed in TABLE 1, are suitable for evaluation and application in the methods and compositions of the present invention. Where neutralization is not known or evaluated, it can be assessed using methods known and available to the skilled artisan, including as described and referenced herein.

TABLE 2 provides an illustrative tabulation of exemplary antibody sequences, providing heavy and light chain CDR sequences for some antibodies demonstrated as applicable in the present invention herein. The CDR sequences are based on and derived from published or available sequences, including in publications as noted in TABLE 1.

The present invention demonstrates intranasal efficacy at low doses for numerous distinct neutralizing antibodies, including known antibodies and newly isolated antibodies. In particular, exemplary intranasal efficacy is provided for numerous distinct and known antibodies as exemplary antibodies, including antibodies CR6261, CR8020, CR9114, 6F12, GG3, 5A7, mAb53 and mAb579. Such activity and efficacy has not been demonstrated for these particular antibodies, this despite numerous studies for example of CR6261 and CR8020, including preclinical trials. Numerous distinct antibodies, including known and newly isolated antibodies, are assessed herein and are similarly efficacious. The antibodies active and effective in accordance with the present invention are directed to varying epitopes and recognize distinct subtypes, including subtypes H1, H3, H5 of influenza A virus and also influenza B. Thus, the invention provides a generally applicable phenomenon, wherein an antibody capable of neutralizing virus can be utilized in methods and compositions for intranasal administration and treatment or prevention of virus, infection and/or transmission by intranasally administering one or more antibody directed against the virus, particularly one or more monoclonal antibody, particularly against influenza virus. Provided the antibody is capable of neutralization, its target or epitope and its isotype (IgG isotype) do not appear relevant. Additional antibodies having similar or comparable capabilities and neutralizing ability are therefore of use in the invention. Antibody fragments, derivatives or variants are contemplated. Antibody fragments, including Fabs, are demonstrated herein to be effective in accordance with the invention. In one aspect of the invention, antibody Fab fragments are active and efficacious when administered intranasally or via inhalation, and are ineffective when administered IP or IV.

TABLE 1

| Mab Name | origin | Subtype | Target Epitope | sub-class | Publication | therapeutic breadth shown | therapeutic dose* |
|---|---|---|---|---|---|---|---|
| C179 | mouse | H1 and H2 | stalk | IgG2a | Okuno et al (1993) J Virol 67: 2552-2558<br>Okuno et al (1994) J Virol 68: 517-520 | | i.p. ~10 mg/kg |
| F49 | mouse | H3 | | | | | |
| VN04-2 | mouse | H5 (and H1) | stalk | IgG1 | Hanson et al (2006) Resp Res 7: 1465<br>Lim et al (2008) Virology 5: 1743<br>Prabhu et al (2009) Antiviral Ther 14: 911-921 | | |
| FLA3.14 | human | H5 only | unknown | IgG1 | Simmons et al (2007) PLoS Med 4: e178 | H5 | i.p/50 mg/kg |
| mAb1 (aka A06) | human | H5 (and H1) | stalk | | Kashyap et al (2008) PNAS 105: 5986-5991<br>Kashyap et al (2010) PLoS Path 6: e1000990 | VN/04(H5) and CA09 2:6(H1) | i.p. 15 mg/kg [2dpi] |
| CR6261 | human | Group 1 | stalk | IgG1 | Throsby et al (2008) PLoS One 3: e3942<br>Ekiert et al (2009) Science 324: 246-251<br>Koudstaal et al (2009) JID 200: 1870-1873<br>Friesen et al (2010) PLoS One 5: e9106 | H5 and WSN<br>H5 and WSN<br>H5 | i.v. 15 mg/kg [4dpi]<br>i.v. 15 mg/kg [4dpi] |
| CR8020 | human | Group 2 | stalk | | Ekiert et al (2011) Science 333: 843-850 | | i.v. 15 mg/kg [2dpi] |
| CR9114 | human | Type A and reacts w/ B | stalk | | Dreyfus et al (2012) Science 337: 1343-1348 | none shown | |
| CR8033 | human | B | head | | Dreyfus et al (2012) Science 337: 1343-1348 | none shown | |
| CR8071 | human | B | head | | Dreyfus et al (2012) Science 337: 1343-1348 | none shown | |
| F10 | human | Group 1 | stalk | IgG1 | Sui et al (2009) Nat Struct Mol Bio 16: 26-273<br>Hashem et al (2010) Biochem and Biophy 403: 247-251 | H5 | i.p. 15 mg/kg |
| S139/1 | mouse | H1, 2, 3, 5, 9, 13 | head | | Yoshida et al (2009) PLoS Path 5: e1000350 | none shown | |
| FE17 or FE41 | human | H5 (and H1) | head | | Corti et al (2010) JCI 120: 1663-1673 | | |
| 12D1 | mouse | H3 | stalk | | Wang et al (2010) PLoS Path 6: e1000796 | | |
| 6F12 | mouse | H1 | stalk | | Tan et al (2012) J Virology 86, 6179-6188 | H1 Neth/09 | i.p. 30 mg/kg (4dpi) |
| GG3 | mouse | H1 | stalk | | | | |
| Multiple | human | H1 and H5 | stalk | | Wrammert et al (2011) JEM 208: 181-193 | | |
| FI6v3 | human | Type A | stalk | | Corti et al (2011) Science333: 850-856 | | i.v. 15 mg/kg [2dpi] |
| PN-SIA28 | human | H1 | unknown | Fab | Burioni et al (2009) New Microbiologica 32: 319-324<br>Burioni et al (2010) Virology 399: 144-152 | none shown | |
| PN-SIA49 | | Group 1 | | | Burioni et al (2010) Virology 399: 144-152 | | |
| CH65 | human | most H1s | head | IgG1 | Whittle et al (2011) PNAS 108: 14216-14221 | none shown | |
| mAb 486 | human | Type A | stalk | | WO2013/086052 | | |
| maAb 53 | human | Group 1 | stalk | | WO2011/160083 | | |
| mAb 579 | human | Group 2 | stalk | | WO2013/086052 | | |
| TCN-032 (anti-M2) | | Type A only | n/a | | Grandea et al (2010) PNAS 107(28): 12658-12663 | | |
| VIS410 | | Type A | stalk | | US2013/0302349 | | |
| 5A7 | human | Type B | stalk | | Yasugi et al (2013) PLoS Pathogens 9(2): e1003150;<br>WO2013/114885 | | |

*indicates the minimum dose required to achieve 100% survival in mice at the latest time post infection.

TABLE 2

| | | HEAVY CHAIN | | | | LIGHT CHAIN | | | |
|---|---|---|---|---|---|---|---|---|---|
| mAb Name | Specificity | Heavy Chain Gene | IMGT CDR1 | IMGT CDR2 | IMGT CDR3 | Light Chain Gene | IMGT CDR1 | IMGT CDR2 | IMGT CDR3 |
| CR6261 | A Group 1 | IGHV1-69*12 | GGPFRSYA | IIPIFGTT | AKHMGYQVRETMDV | IGLV1-51*01 | SSNIGNDY | DNN | ATWDRRPTAYVV |
| GG3 | A Group 1 | IGHV9-1*02 | GYTFTNYG | INIYSGES | ARSGDTMITAGRSFFAMDY | IGLV9-124*01 | QEISGY | AAS | LQYANYPWS |
| TRL053 | A Group 1 | IGHV1-69*12 | GGIIRKYA | IIAIFNTA | ARGMNYYSDYFDY | IGLV3-20*01 | QSVRSNN | GAS | QQYGSSPALT |

TABLE 2-continued

| | | HEAVY CHAIN | | | | LIGHT CHAIN | | | |
|---|---|---|---|---|---|---|---|---|---|
| mAb Name | Specificity | Heavy Chain Gene | IMGT CDR1 | IMGT CDR2 | IMGT CDR3 | Light Chain Gene | IMGT CDR1 | IMGT CDR2 | IMGT CDR3 |
| CR8020 | A Group 2 | IGHV1-18*01 | GYTFTSFG | ISAYNGDT | AREPPLFYSSWSLDN | IGLV3-20*01 | QSVSMNY | GAS | QQYGTSPRT |
| TRL579 | A Group 2 | IGHV1-3*01 | GYTFTAYT | INAGNGHT | ARGPETYYYDKTNWLNSHPDEYFQH | IGLV1-5*03 | QTINNY | KAS | QEYNNDSPLT |
| 5A7 | B | IGHV3-33*01 | GFTFNNYG | VWYDGLIK | ARDLQPPHSPYGMDV | IGLV1-47*02 | SSNIGSND | NNN | AAWDDSLTVS |
| CR8033 | B | IGHV3-9*01 | GFSFDEYT | INWKGNFM | AKDRLESSAMDILEGGTFDI | IGLV3-20*01 | QSVSSSY | GAS | QQYGSSPWT |
| CR8071 | B | IGHV1-18*01 | GYIFTESG | ISGYSGDT | ARDVQYSGSYLGAYY | IGLV1-47*01 | SSNIGTNY | RSY | ATWDDSLDGWV |
| CR9114 | A and B | IGHV1-69*06 | GGTSNNYA | ISPIFGST | ARHGNYYYYSGMDV | IGLV1-44*01 | DSNIGRRS | SND | AAWDDSLKGAV |

The neutralizing antibodies useful for IN delivery and administration may be combined with non-neutralizing antibodies. The present application demonstrates that IN administration can be combined with alternative routes of administration, including IP or IV administration, to give overall and combination enhanced efficacy. As provided herein, combined IN and IP administration of an antibody gives enhanced synergistic activity and efficacy versus either IN or IP alone. In addition to providing a replacement or alternative administration or treatment method, the invention provides an enhanced combination approach to antibody-mediated therapy and prophylaxis wherein IN administration is combined with systemic administration, including IP administration, for superlative efficacy.

Alternative means of dosing, lower dosing, lower dose formulations and novel methods of administration are provided by the present invention.

Compositions

In accordance with the present invention, compositions are provided for use and administration intranasally. The compositions particularly comprise neutralizing antibody, particularly monoclonal antibody or an active fragment thereof, particularly antiviral antibody, particularly influenza antibody. The compositions may comprise one or more neutralizing antibody, particularly one or more monoclonal antibody or an active fragment thereof, particularly antiviral antibody, particularly influenza antibody. The compositions particularly comprise more than one neutralizing antibody, particularly monoclonal antibody or an active fragment thereof, particularly antiviral antibody, particularly influenza antibody. The neutralizing antibody may neutralize more than one type or subtype of influenza or may be combined with antibodies neutralizing distinct types or Groups of influenza. A composition of the invention particularly comprises a combination of influenza neutralizing antibodies directed against circulating influenza virus strains. Composition(s) particularly may comprise a combination of influenza neutralizing antibodies directed against circulating influenza virus strains, particularly an anti-influenza A and an anti-influenza B antibody. Composition(s) particularly may comprise a combination of influenza neutralizing antibodies directed against circulating influenza virus strains, particularly one or more anti-influenza A virus and one or more anti-influenza B antibody. Composition(s) particularly may comprise a combination of influenza neutralizing antibodies which combination is collectively directed against the appropriate and relevant circulating influenza virus strains, particularly directed collectively against influenza A H1 and H3 subtypes and against influenza B of the Yamagata and Victoris lineages. The composition(s) may comprise one, two, three or more neutralizing antibodies, provided that influenza viruses A and B are neutralized by the combination or antibodies.

Composition(s) particularly may comprise a combination of influenza neutralizing antibodies directed against circulating influenza virus strains, particularly an influenza A anti-H1 antibody, an influenza A anti-H3 antibody and an anti-influenza B antibody. Composition(s) may include influenza A antibody effective against or further effective against influenza H5 and H7 strains. The influenza antibody may be strain specific or non specific or pan-specific and may neutralize influenza A, including H1 subtype and/or H3 subtype and/or H5 and/or H7 or other influenza A strains or subtypes, and/or may neutralize influenza B, including Yamagata and/or Victoria lineages. The compositions may have identical components or distinct or additive components as alternative administration compositions, such as IV or IP, of the antibody.

The invention provides intranasal antibody combination compositions, or compositions of a combination of antibodies, particularly influenza antibodies and particularly monoclonal influenza antibodies, suitable or selected for intranasal administration wherein the combination of antibodies comprises, includes or consists of antibodies directed against the circulating virus strains. Thus, in as much as influenza circulating strains are currently influenza B (Yamagata), influenza B (Victoria), influenza A H1 subtype and influenza A H3 subtype, a combination composition of the invention is provided having or comprising antibody(ies) directed against each of Influenza B (Yamagata), influenza B (Victoria), influenza A H1 subtype and influenza A H3 subtype.

It is notable that antibodies in the combination may be directed against more than one influenza strain or subtype, such as indicated in Table 1 and demonstrated herein. Thus, as demonstrated herein antibody CR9114 or CA9114 as herein utilized, is effective against influenza A and influenza B strains. Antibody CR6261 or CA6261 as utilized herein, is effective against various Group 1 influenza A subtypes, including H1, H5 etc. Antibody CR8020 or CA8020 as herein utilized, is effective against various Group 2 influenza A subtypes including H3 and H7. Antibody Mab53 is effective against influenza A H1, H9, H7 and H5 subtypes of Group 1 and 2. Antibody Mab579 is effective against H3 and H7 subtypes. Thus, while the presently circulating influenza strains are H1, H3 and B types, combinations having efficacy against additional strains and subtypes, including subtypes which may arise and emerge in a new or single flu season, can be generated and are herein provided.

The compositions may particularly be formulated or contain lower doses or amounts of antibody than any alternative dosage or administration form, such as IP or IV. Thus, compositions of use in the present invention may comprise a 5 fold, 10 fold, 20 fold, 50 fold, 100 fold, greater than 10 fold, greater than 100 fold reduced amount of neutralizing antibody versus or in comparison to compositions thereof for alternative administration, particularly IP or IV administration.

Compositions of the present invention may particularly comprise a dose of antibody that is intended for administration, particularly intranasally, in an amount less than 1 mg/kg on the basis of the body weight of a mammal. In a particular aspect compositions thereof comprise antibody amounting to administration of less than 1 mg/kg on the basis of the body weight of a human. Compositions of the present invention may particularly comprise a dose of antibody that is intended for administration, particularly intranasally, in an amount less than 1 mg/kg, less than 0.5 mg/kg, less than 0.1 mg/kg, less than 0.05 mg/kg, less than 0.01 mg/kg, less than 0.005 mg/kg, less than 0.0025 mg/kg, less than 0.001 mg/kg on the basis of the body weight of a mammal, including a clinically relevant mammal, such as a mouse, dog, horse, cat or a human.

One of skill in the art can determine, including on the basis of efficacy in animal models and in consideration of clinical and physiological response, viral load and viral transmission rates, the appropriate and efficacious dose in a mammal, including a human. Thus, the invention and dosing parameters are not limited by the examples provided herein or the specific doses exemplified. The present invention demonstrates that inhalation or intranasal dosing is a preferred alternative in terms of efficacy and in reducing, limiting or blocking the clinically manifested effects of a virus infection, including influenza virus infection. Inhalation or intranasal administration of neutralizing antibodies provides improved and enhanced efficacy versus other routes of administration, including IP or IV, which would not have been expected or predicted. The amounts and timing of dosing via IN or inhalation routes can be further assessed and determined by one of skill in the art. The studies provided herein demonstrate that IN or inhalation administration is more efficacious at lower doses versus IP or IV and that administration can occur days following infection and still retain efficacy.

Doses and dose ranges applied and demonstrated herein in mouse models may be converted or applied as appropriate and using parameters known in the art by the skilled artisan or clinical or medical professional. Thus, mg/kg dosing in a mouse can be extrapolated to comparable or reasonably equivalent dosing to a human or other animal. For example, the average weight of a laboratory mouse is 20 g whereas the average weight of a human is 70 kg.

It is routine practice in clinical research to convert animal doses into human doses, and that the skilled person would have a strong expectation that such converted dose(s) would be successful in humans. Interspecies scaling and predicting pharmacokinetic parameters in humans have been described (for example, Mahmood et al. (2003) J Clin Pharmacol 43: 692-697; Mordenti (1986) Journal of Pharmaceutical Sciences, 75:1028-1040). For example, therapeutic levels are often assumed to parallel toxicity, and so the conversion factors applied to converting animal toxicity to human toxicity are commonly used to convert minimum effective doses in animals to minimum effective doses in humans. Further, the FDA provides a "Guidance for Industry" which provides conversion factors for estimating the maximum safe starting dose in clinical trials for therapeutics, including factors used to convert animal (mouse) doses to human doses (such as in one instance multiply the mouse dose by 0.08).

The phrase "pharmaceutically acceptable" refers to molecular entities and compositions that are physiologically tolerable and do not typically produce an allergic or similar untoward reaction, such as gastric upset, dizziness and the like, when administered to a human.

'Therapeutically effective amount' means that amount of a drug, compound, antimicrobial, antibody, or pharmaceutical agent that will elicit the biological or medical response of a subject that is being sought by a medical doctor or other clinician. In particular, with regard to viral infections and proliferation of virus, the term "effective amount" is intended to include an effective amount of a compound or agent that will bring about a biologically meaningful decrease in the amount of or extent of virus replication or pathogenesis and or decrease in length of illness (fever, joint pains, discomfort) in a subject, or a reduction in loss of body weight in an infected individual. The phrase "therapeutically effective amount" is used herein to mean an amount sufficient to prevent, and preferably reduce by at least about 30 percent, more preferably by at least 50 percent, most preferably by at least 90 percent, a clinically significant change in the body weight, virus load, virus replication, virus transmission, or other feature of pathology such as for example, fever or white cell count as may attend its presence and activity.

In certain embodiments, an "effective amount" in the context of administration of a therapy to a subject refers to the amount of a therapy which is sufficient to achieve one, two, three, four, or more of the following effects: (i) reduction or amelioration the severity of an Influenza virus infection, an Influenza virus disease or a symptom associated therewith; (ii) reduction in the duration of an Influenza virus infection, an Influenza virus disease or a symptom associated therewith; (iii) prevention of the progression of an Influenza virus infection, an Influenza virus disease or a symptom associated therewith; (iv) regression of an Influenza virus infection, an Influenza virus disease or a symptom associated therewith; (v) prevention of the development or onset of an Influenza virus infection, an Influenza virus disease or a symptom associated therewith; (vi) prevention of the recurrence of an Influenza virus infection, an Influenza virus disease or a symptom associated therewith; (vii) reduction or prevention of the spread of an Influenza virus from one cell to another cell, one tissue to another tissue, or one organ to another organ; (viii) prevention or reduction of the spread/transmission of an Influenza virus from one subject to another subject; (ix) reduction in organ failure associated with an Influenza virus infection or Influenza virus disease; (x) reduction in the hospitalization of a subject; (xi) reduction in the hospitalization length; (xii) an increase in the survival of a subject with an Influenza virus infection or a disease associated therewith; (xiii) elimination of an Influenza virus infection or a disease associated therewith; (xiv) inhibition or reduction in Influenza virus replication; (xv) inhibition or reduction in the binding or fusion of Influenza virus to a host cell(s); (xvi) inhibition or reduction in the entry of an Influenza virus into a host cell(s); (xvii) inhibition or reduction of replication of the Influenza virus genome; (xviii) inhibition or reduction in the synthesis of Influenza virus proteins; (xix) inhibition or reduction in the assembly of Influenza virus particles; (xx) inhibition or reduction in the release of Influenza virus particles from a host cell(s); (xxi) reduction in Influenza virus titer; (xxii) the reduction in the number of symptoms associated with an Influenza virus infection or an Influenza virus disease; (xxiii) enhancement, improvement, supplementation, complementation, or augmentation of the prophylactic or therapeutic effect(s) of another therapy; (xxiv) prevention of the onset or progression of a secondary infection associated with an Influenza virus infection; and/or (xxv) prevention of the onset or diminution of disease severity of bacterial pneumonias occurring secondary to Influenza virus infections. In some embodiments, the "effective amount" of a therapy has a beneficial effect but does not cure an Influenza virus infection or a disease associated therewith. In certain embodiments, the "effective amount" of a therapy may encompass the administration of multiple doses of a therapy at a certain frequency to achieve an amount of the therapy that has a prophylactic and/or therapeutic effect. In other situations, the "effective amount" of a therapy may encompass the administration of a single dose of a therapy at a certain amount.

A symptom or symptoms associated with virus infection, including particularly influenza infection, disease or exposure, may include, but not be limited to fever of 100° F. or higher, feeling feverish, cough and/or sore thropat, runny or stuffy nose, headache and/or body aches, chills, fatigue, generalized weakness, nausea, vomiting and/or diarrhea, aches and pains in the joints and muscles and/or around the eyes.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of anti-infectives or of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term 'treating' or 'treatment' of any disease or infection refers, in one embodiment, to ameliorating the disease or infection (i.e., arresting the disease or growth of the infectious agent or virus or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease, transmission of disease, or reducing an infection.

As used herein, "pg" means picogram, "ng" means nanogram, "ug" or "μg" mean microgram, "mg" means milligram, "ul" or "μl" mean microliter, "ml" means milliliter, "l" means liter.

The present invention further contemplates therapeutic compositions useful in practicing the therapeutic methods of this invention. A subject therapeutic composition includes, in admixture, a pharmaceutically acceptable excipient (carrier) and one or more of an antibody or active fragment thereof, particularly a neutralizing antibody, polypeptide analog thereof or fragment thereof, as described herein as an active ingredient. In a preferred embodiment, the composition comprises an antibody or fragment capable of neutralizing virus, particularly influenza virus, within a target cell or in a subject or patient.

The preparation of therapeutic compositions which contain antibodies, polypeptides, analogs or active fragments as active ingredients is well understood in the art. Typically, such compositions are prepared for administration either as liquid solutions or suspensions, however, solid forms suitable for solution in, or suspension in, liquid prior to administration can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An antibody, polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody-, polypeptide-, analog- or active fragment-containing compositions are conventionally administered, as by administration of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

As provided herein, the unit dose of neutralizing antibody for intranasal administration effective and useful for treatment or prophylaxis of virus, particularly influenza virus, is comparatively reduced versus that indicated or required for alternative administration, such as that required for IP or IV administration. Thus in an aspect hereof is provided an antibody composition for administration, particularly intranasal administration, wherein the unit dose is reduced by orders of magnitude, particularly several or multiple orders of magnitude versus that indicated or required for alternative administration, such as that required for IP or IV administration. Thus in an aspect hereof is provided an antibody composition for administration, particularly intranasal administration, wherein the unit dose is at least 10 fold, 10 fold, 20 fold, 25 fold, 50 fold, at least 100 fold, 100 fold, 500 fold, up to 1000 fold reduced. In particular the composition is thus reduced in comparison to an equivalent unit dose for IP or IV administration, particularly for the same or comparable indication or effect and/or activity. The IN unit dose may be combined with IP or IV dose for improved efficacy.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of virus desired. Precise amounts of active ingredient required to be administered depend on the judgment of the practitioner and are peculiar to each individual. However, suitable dosages may range from about 0.001 to 10, preferably about 0.005 to about 1, less than 1, less than 0.5, less than 0.1, less than 0.05, less than 0.01, and more preferably below one, below 0.5, blow 0.1, milligrams of active ingredient per kilogram body weight of individual per dose for intranasal administration. Suitable regimes for initial administration and follow-on administration are also variable. In one regime there is an initial administration followed by repeated subsequent dose(s), a single or multiple subsequent doses, at one or more hour intervals by a subsequent injection or other administration.

Initial administration IN may be followed by administration of higher doses of antibody IP or IV or by other suitable route. In an aspect of the invention a novel dosing approach or parameter is provided wherein a patient or subject is administered neutralizing antibody intranasally, and either concomitantly, subsequently or later administered a neutralizing or non-neutralizing antibody by IP or IV administration.

The therapeutic compositions, particularly intranasal compositions, may further include an effective amount of the neutralizing antibody or fragment thereof, and one or more of the following active ingredients: an antibiotic, an antiviral agent, a steroid, an anti-inflammatory. In a particular aspect, the compositions include an antiviral agent. The compositions may include an anti-influenza agent. The anti-influenza agent may be a neuraminidase inhibitor, including an agent selected from Tamiflu and Relenza.

As used herein, "pg" means picogram, "ng" means nanogram, "ug" or "pg" mean microgram, "mg" means milligram, "ul" or "µl" mean microliter, "ml" means milliliter, "l" means liter.

Compositions may be formulated in nasal sprays or inhalation solutions or suspensions using approaches known and acceptable in the art and in the medical field and clinical practice. The FDA provides guideline and guidance with regard to such sprays, solutions and suspensions and spray drug products, including in Guidance for Industry documents available at fda.gov. An exemplary July 2002 Guidance for Industry document entitled Nasal Spray and Inhalation Solution, Suspension and Spray Drug Products—Chemistry, Manufacturing and Controls Documentation includes details regarding formulation components and compositions, specifications therefore, manufacturing, and closed container systems.

Nasal Spray are drug products that contain active ingredients dissolved or suspended in a formulation, typically aqueous-based, which can contain other excipients and are intended for use by nasal inhalation. Container closure systems for nasal sprays include the container and all components that are responsible for metering, atomization, and delivery of the formulation to the patient. Nasal spray drug products contain therapeutically active ingredients (drug substances) dissolved or suspended in solutions or mixtures of excipients (e.g., preservatives, viscosity modifiers, emulsifiers, buffering agents) in nonpressurized dispensers that deliver a spray containing a metered dose of the active ingredient. The dose can be metered by the spray pump or could have been premetered during manufacture. A nasal spray unit can be designed for unit dosing or can discharge numerous metered sprays of formulation containing the drug substance. Nasal sprays are applied to the nasal cavity for local and/or systemic effects.

Inhalation solution and suspension drug products are typically aqueous-based formulations that contain therapeutically active ingredients and can also contain additional excipients. Aqueous-based oral inhalation solutions and suspension must be sterile (21 CFR 200.51). Inhalation solutions and suspensions are intended for delivery to the lungs by oral inhalation for local and/or systemic effects and are to be used with a specified nebulizer. An inhalation spray drug product consists of the formulation and the container closure system. The formulations are typically aqueous based and do not contain any propellant.

Current container closure system designs for inhalation spray drug products include both premetered and device-metered presentations using mechanical or power assistance and/or energy from patient inspiration for production of the spray plume. Premetered presentations contain previously measured doses or a dose fraction in some type of units (e.g., single or multiple blisters or other cavities) that are subsequently inserted into the device during manufacture or by the patient before use. Typical device-metered units have a reservoir containing formulation sufficient for multiple doses that are delivered as metered sprays by the device itself when activated by the patient.

A prolonged residence time in the nasal cavity may also be achieved by using bioadhesive polymers, microspheres, chitosan or by increasing the viscosity of the formulation. Nasal mucociliary clearance can also be stimulated or inhibited by drugs, excipients, preservatives and/or absorption enhancers and thus affect drug delivery to the absorption site.

Microsphere technology is one of the specialized systems being utilized for designing nasal products. Microspheres may provide more prolonged contact with the nasal mucosa and thus enhance absorption or efficacy. Microspheres for nasal applications have been prepared using biocompatible materials, such as starch, albumin, dextran and gelatin (Bjork E, Edman P (1990) Int J Pharm 62:187-192).

The pH of a nasal formulation is important to avoid irritation of nasal mucosa, to allow the drug to be available in unionized form for absorption, to prevent growth of pathogenic bacteria in the nasal passage, to maintain functionality of excipients such as preservatives, and to sustain normal physiological ciliary movement. It is preferable to keep the formulation at a pH of 4.5 to 6.5 keeping in mind the physicochemical properties of the drug or active ingredient. Nasal formulations are generally administered in small volumes ranging from 25 to 200 µL with 100 µL being the most common dose volume.

Aqueous solubility of drug may be a relevant parameter limitation for nasal drug delivery in solution. Conventional solvents or co-solvents such as glycols, small quantities of alcohol, Transcutol (diethylene glycol monoethyl ether), medium chain glycerides and Labrasol (saturated polyglycolyzed $C_8$-$C_{10}$ glyceride) can be used to enhance the solubility of drugs. Other options include the use of surfactants or cyclodextrins such as HP-β-Cyclodextrin that serve as a biocompatible solubilizer and stabilizer in combination with lipophilic absorption enhancers. In such cases, their impact on nasal irritancy should be considered.

Most nasal formulations are aqueous based and need preservatives to prevent microbial growth. Parabens, benzalkonium chloride, phenyl ethyl alcohol, EDTA and benzoyl alcohol are some of the commonly used preservatives in nasal formulations. Mercury-containing preservatives have a fast and irreversible effect on ciliary movement and are not recommended for use in nasal systems.

A small quantity of antioxidants may be required to prevent drug oxidation. Commonly used antioxidants are sodium metabisulfite, sodium bisulfate, butylated hydroxytoluene and tocopherol. Usually, antioxidants do not affect drug absorption or cause nasal irritation. Chemical/physical interaction of antioxidants and preservatives with drugs, excipients, manufacturing equipment and packaging components should be considered as part of the formulation development program.

Many allergic and chronic diseases are often connected with crusts and drying of mucous membrane. Certain preservatives/antioxidants among other excipients are also likely to cause nasal irritation especially when used in higher quantities. Adequate intranasal moisture is essential for preventing dehydration. Therefore, humectants can be added especially in gel-based nasal products. Humectants avoid nasal irritation and are not likely to affect drug absorption. Common examples include glycerin, sorbitol and mannitol.

The selection of delivery system depends upon the drug being used, proposed indication, patient population and last but not least, marketing preferences. Some of these delivery systems include nasal drops, nasal sprays, nasal gels, and nasal powders.

Administration

It is again noted that normal and reasonably expected antibody therapy doses are well-established to be IV or IP doses in the mg range. This is based on research and clinical experience to date with numerous recombinant antibodies. To date, over twenty (20) monoclonal antibodies have been clinically approved in the United States (see e.g Newsome B W and Ernstoff M S (2008) Br J Clin Pharmacol 66(1): 6-19). Clinically approved antibodies presently in use are all utilized and administered IP or IV in the mg/kg range.

No influenza monoclonal antibody has been clinically approved to date. All trials in progress or reported currently utilize intravenous delivery as the standard. In particular, TheraClone Sciences antibody TCN-023 was assessed in a single dose-escalation ranging from 1-40 mg/kg (NCT01390025, clinical trails.gov). The TCN-032 antibody is a human antibody that binds to a conserved epitope of the amino-terminal extracellular domain (M2e) of the influenza matrix protein (M2) (Grandea A G et al (2010) PNAS USA 107(28):12658-12663; Epub 2010 Jul. 1). The antibodies CR6261 and CR8020 are being similarly assessed in safety and tolerability studies using escalating doses from 2 mg/kg to 50 mg/kg administered IV over 2 hours (Crucell Holland BV clinical trials NCT01406418 and NCT01756950 respectively).

Influenza vaccines are administered by injection. One exception in influenza vaccines is the FluMist live influenza vaccine (MedImmune) which is administered intranasally. FluMist is a combination of three live flu strains—an A/H1N1 strain, an A/H3N2 strain, and a B strain, and is administered in a 0.2 ml dose using a suspension supplied in a single dose pre-filled intranasal sprayer. In addition to the virus strains, each dose also contains monosodium glutamate, hydrolyzed porcine gelatin, arginine, sucrose, dibasic potassium phosphate and monobasic potassium phosphate, with no preservatives (FluMist Highlights of Prescribing Information, 2012-2013 Formula, MedImmune, RAL-FLUV12, Component No.: 11294).

The invention provides a novel and efficacious mode of administration of antibody(ies) and antibody administration protocol for treatment and prophylaxis of viral infection, particularly viruses which infect or transmit via the respiratory route, including particularly influenza virus. Thus the invention provides for treatment, prophylaxis or alleviation of virus infection, particularly influenza virus, by intranasal administration of antibody capable of neutralizing virus. One or more neutralizing antibody may be administered intranasally, including at the same time, in combination, or sequentially or separately. An antibody may be administered by a single IN dose or may be given in multiple individual doses. Individual doses may be administered one after another, each administration separated by minutes, hours, or days.

In a particular aspect, the invention provides for treatment, prophylaxis or alleviation of virus infection, particularly influenza virus, by intranasal administration of a combination of antibodies directed against circulating strains of influenza. Thus, treatment, prophylaxis or alleviation of virus infection, particularly influenza virus, is provided and achieved in accordance with the invention by intranasal administration of a combination of antibodies directed against influenza B and circulating influenza A viruses, particularly in an aspect thereof a combination of anti-influenza B antibody, anti-Group 1 influenza A antibody, such as anti-H1 antibody, and anti-Group 2 influenza A antibody, such as anti-H3 antibody. In accordance with the present invention, intranasal administration of a combination of anti-influenza B antibody, anti-Group 1 influenza A antibody, such as anti-H1 antibody, and anti-Group 2 influenza A antibody, such as anti-H3 antibody, is effective in preventing infection or treating influenza infection by an influenza B or influenza A virus. To the extent that antibodies are available, and herein tested and demonstrated, to be effective and directed against more than one subtype or strain of virus, the combinations provided and contemplated herein serve as a universal cocktail or combination effective against numerous strains and/or subtypes of virus, particularly influenza virus, including known and circulating strains or subtypes, emerging strains or subtypes and unknown, unanticipated and variant strains or subtypes.

Antibody of use in the invention may be administered intranasally or by inhalation, followed by or along with, including at the same time, in combination, or sequentially or separately, systemic administration of another or the same antibody, particularly IP or IV administration. Thus, a combination administration protocol or method is contemplated and provided herein, wherein intranasal and IP (or IV) administration is combined for enhanced efficacy against an agent, particularly virus, particularly influenza virus. Indeed, the studies provided herein demonstrate that using combined dosing of intranasal with alternative administration (IP or IV) the combined efficacy is synergistic and low doses both IN and IP as an example can be utilized.

The invention provides a method for treatment or prophylaxis of viral infection in a mammal exposed to, at risk of exposure, having contracted, clinically presenting symptoms or suffering from a respiratory virus comprising administering intranasally (IN) or via inhalation to said mammal a monoclonal antibody capable of neutralizing the respiratory virus. The monoclonal antibody may particularly be an IgG antibody. The respiratory virus may be influenza virus or suspected influenza virus, or an unknown respiratory virus.

Antibody can be administered post infection or after presumed infection. In an aspect thereof, the antibody can be administered in a time period up to 8 hours post infection (hpi), including 2 hpi, 4 hpi, 6 hpi, 8 hpi. Alternatively, the antibody is administered in a time period up to 24 hours post infection, including 4 hpi, 8 hpi, 12 hpi, 18 hpi, 24 hpi. In a further alternative, the antibody is administered in a time period up to 48 hours post infection, including 12 hpi, 24 hpi, 36 hpi, 48 hpi. In a still further alternative, the antibody is administered in a time period up to 72 hours post infection, including 24 hpi, 36 hpi, 48 hpi, 60 hpi, 72 hpi. Antibody may be administered days post infection, or after presumed infection, or after presentation of clinical symptoms, such as fever, aches, joint pain, lethargy. Antibody may be administered 1 day post infection, 2 days post infection, 3 days post infection, 4 days post infection, 5 days post infection, 6 days post infection, 7 days post infection, 10 days post infection, 12 days post infection, 14 days post infection. Antibody may be administered weeks after infection or presumed infection, including 1 week after, 2 weeks after, 3 weeks after, 4 weeks after, a month after.

Antibody can be administered before infection or in order to reduce or prevent transmission, or before any clinical indication of illness, disease or infection. In an aspect thereof, the antibody can be administered in a time period days before infection or before possible or presumed exposure or risk of exposure as a prophylactic. Antibody may be administered a day prior or before, 2 days before or prior, 3 days prior or before, 4 days prior or before, 5 days prior or before, 6 days prior or before, 7 days prior or before, a week prior or before, more than 7 days prior or before, more than a week prior or before, up to 9 days prior or before, up to 10 days prior or before. Antibody may be administered one or more times prior or before in one or more doses, separated by hours, days or weeks.

The antibody may be administered in a single dose or in multiple doses. Each dose may be identical in unit or mg/kg amount or may be different in amount. For example an initial dose may be a higher relative dose, such as for example but not by limitation about 1 mg/kg, greater than 1 mg/kg, less than 1 mg/kg, or about the maximum or near maximum tolerated dose, or one half maximum tolerated dose for the mammal being administered. Subsequent doses may be the same as the initial dose or may be less than or greater than the initial dose, and may depend on the reaction or response in the subject or patient or the alleviation or degree of clinical symptoms.

The multiple doses, of the same or different amounts each or any dose, may be administered hours, minutes, days or weeks apart. The timing may vary and may be shortened or lengthened depending on response and symptoms. Doses, for example and not by limitation, may be at least 2 hours apart, at least 4 hours apart, at least 6 hours apart, at least 8 hours apart, at least 24 hours apart, at least 48 hours apart, at least 72 hours apart. The antibody dose or doses may be administered post infection or post presumed infection and up to 2, 4, 6, 8, 12, 24, 36, 48, 72 hours after, up to 1 day, 2 days, 3 days, 4 days, 5 days, 6 days, 7 days, a week, 2 weeks, 3 weeks, 4 weeks, a month or longer.

The method may comprise additional administration IP or IV of a virus specific monoclonal antibody wherein the antibody additionally administered is a neutralizing or non-neutralizing antibody. The antibody additionally administered IP or IV may be the same antibody as administered IN or via inhalation. The antibody additionally administered IP or IV may be administered simultaneously, sequentially, or subsequently to the IN or inhalation administered antibody. Any such subsequent administration may be hours later and may be 2, 4, 6, 8, 12, 24, 36, 48, 72 or more hours later. Subsequent administration may be days later and may be 1 day, 2 days, 3 days, 4 days, 5 days, 6 days 7 days later. Subsequent administration may be weeks later and may be 1, 2, 3, 4 or 5 weeks later.

An inhalation or intransal dose may be used to boost response or efficacy in a patient or subject that is particularly ill or continuing to demonstrate symptoms of infection or illness after an initial IN or IP or IV or combined dose.

In a further aspect, the invention provides a protocol for administration of monoclonal antibody against respiratory virus comprising administering a first intranasal or inhalation dose of neutralizing antibody and subsequently or simultaneously administering a second dose of antibody intraperitoneally or intravenously, or again intranasally or by inhalation, wherein the antibody of the second dose is the same or a different antibody as antibody of the first dose. The antibody of the second dose, or any additional dose, may be a neutralizing or a non-neutralizing antibody.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Therapeutic treatment of influenza with monoclonal antibodies to HA is dose dependent, and also requires higher doses at later times post infection. Typical therapeutic doses given IP or IV of broadly-reactive HA specific antibodies require doses ranging from 2 mg/kg to 50 mg/kg in order to see protection from lethal challenges. At later times post infection the same effect requires dosing in ranges that are above >10 mg/kg. An average adult weighs in North America is approximately 80.7 kg and would require 807 mgs of antibody if given 10 mg/kg. Two current phase 1 studies of influenza monoclonal antibodies CR6261 and CR8020 by Crucell Holland BV are assessing safety and tolerability in single doses escalating from 1 mg/kg to 50 mg/kg (trials NCT01406418 and NCT01756950 respectively; clinical trials.gov). In mice, these antibodies required 15 mg/kg to protect mice from death (Friesen, R H E et al (2010) PLoS ONE 5(2):e1906); Ekiert D C et al (2011) Science 333:843-850). As such, using the present applicable approaches, near or at gram amounts of antibody per patient will be required based on the weight of a human (about 70 kg). This is compounded by the need, in any therapy directed at multiple influenza subtypes, for more than one antibody to treat the three different subtypes of influenza that are in circulation (influenza A H3, influenza A H1 and influenza B) and may thus require a total of on the order of 3 grams of antibody, assuming about a gram of each antibody. This large amount of antibody becomes cost prohibitive and presents a major hurdle in the development of therapeutic antibodies for influenza.

We have identified a solution to reduce the amount of antibody significantly, by more than 10 fold, while remarkably retaining and even improving efficacy. We have found that intranasal delivery of antibodies provides a marked and significant improvement in efficacy compared to IV or IP route. Furthermore, this intranasal efficacy phenomenon is specific for antibodies that are neutralizing, as non-neutralizing antibodies exhibit impaired efficacy when delivered by this route.

Our studies demonstrate that intranasal (IN) delivery of neutralizing antibodies can dramatically increase therapeutic efficacy by more than 10 fold compared to intraperitoneal (IP) or intravenous (IV) route of delivery, using an accepted and known influenza mouse model. Comparable efficacy can be achieved using less than one tenth of the same dose when given IN instead of by IV or IP routes. Current therapeutic designs for treating influenza utilize intravenous delivery as the standard (ClinicalTrials.gov Identifier: NCT01390025, NCT01756950, NCT01406418). This delivery approach is the standard in the field as the ability to capitalize on the neutralization characteristics of an antibody are not known. The vast majority of research on antibody therapeutics utilizes IV or IP delivery, and fails to recognize that IN delivery of neutralizing antibodies to respiratory pathogens will improve the efficacy compared to IV or IP delivery. Conversely, the field fails to recognize that neutralization may not be necessary for systemically delivered antibodies, as non-neutralizing antibodies against HA are similarly effective as neutralizing antibodies. In this regard, an antibody that is capable of being more broadly-reactive will be more clinically relevant than an antibody's neutralization capability.

Previous reports of IN delivery have evaluated polyclonal sera gamma globulin IVIG or the IgA class of antibodies (IgA antibodies are inherently common for the lung) (Akerfeldt S et al (1973) Biochem Pharmacol 22:2911-2917; Ramisse F et al (1998) Clin Exp Immmunol 111:583-587; Ye J et al (2010) Clin Vaccine Immunol 17(9):1363). One group tested an ascites fluid preparation of an antibody (C179) by IN route and described that protective IN delivery (pre-challenge) was comparable to IP (Sakabe S et al (2010) Antiviral Res 88(3):249-255). C179 exhibits low neutralizing activity against the 2009 pandemic H1N1 virus, but could protect the mice from infection.

Contrary to this, we have found that importantly the increased efficacy does not occur simply for cross-reactive anti-influenza antibodies, such as cross-reactive anti-HA antibodies, in fact antibodies that do not neutralize when given IN do not exhibit efficacy against influenza. The prior art and earlier studies have failed to recognize that this effect can be applied more broadly to antibodies that exhibit in vitro neutralization activity, irrespective of their viral epitope or protein target. Furthermore, antibodies do not need to be cross-reactive against HA, as strain specific antibodies that can neutralize will exhibit increased efficacy when given IN. We have found that neutralizing antibodies (and not simply cross-reactive anti-HA antibodies) are essential for significantly reducing the amount of antibody needed to achieve comparable efficacy depending on the route of administration. In fact we have found that the inverse occurs when using cross-reactive anti-HA antibodies that are not neutralizing. Therapeutic use of these cross-reactive non-neutralizing anti-HA antibodies results in a marked reduction in therapeutic efficacy when treating mice intranasally despite exhibiting similar efficacy when comparing these antibodies using IP or IV routes of delivery.

Figure 12:
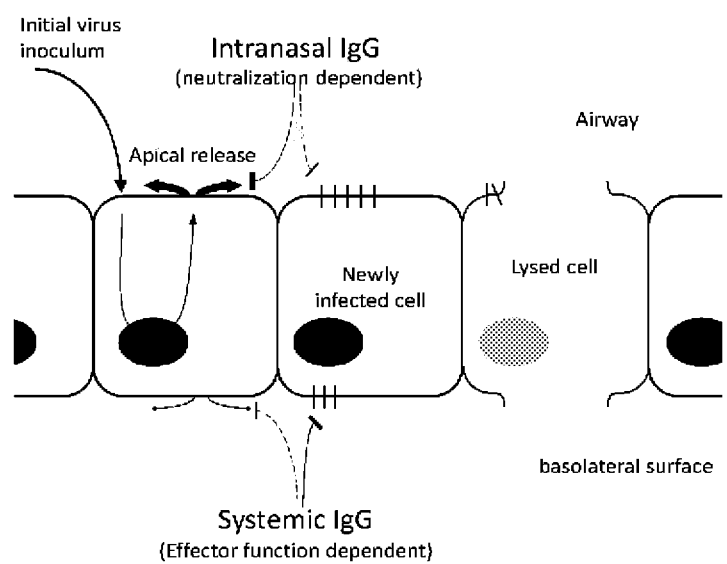
FIG. 12 depicts model of intranasal versus systemic administration avenues. Virus clearance is mediated primarily through effector function (EF) on the basolateral side in the case of systemic administration (including IP and IV administration), and by neutralization on the apical side exposed to the airway in the case of administration to the airway (including intranasal and inhalation administration).
Figure 13A:
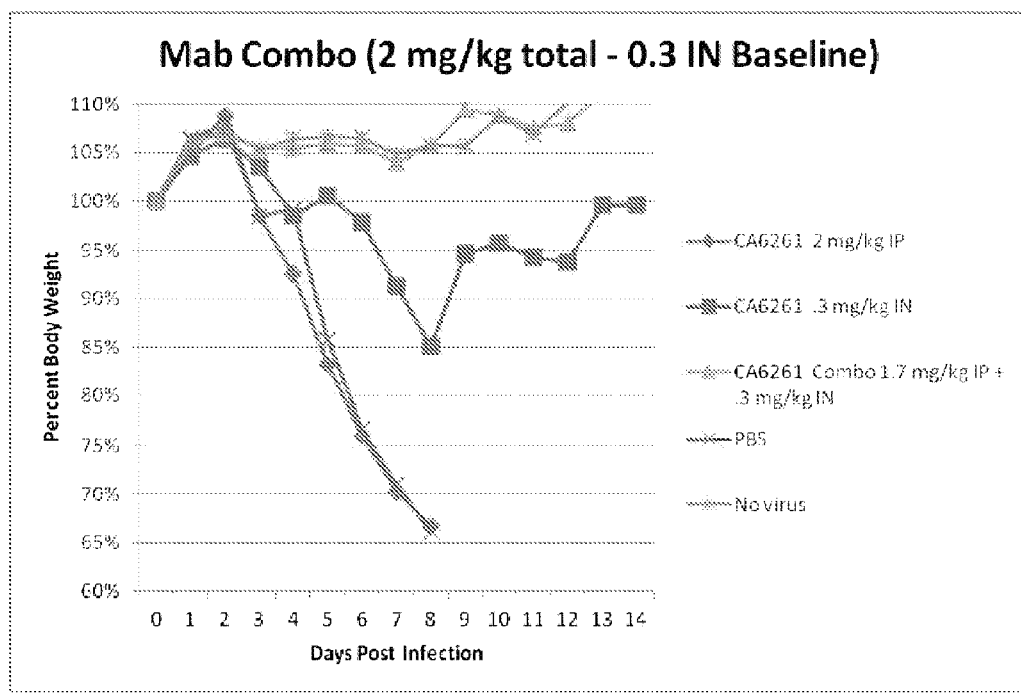
FIG. 13A-13D depicts antibody administration studies of IN or IP administration alone versus combination administration by IN and IP routes, using exemplary antibody CA6261. Total antibody administration dose of 2 mg/kg is depicted in A and B, with IN baseline of 0.3 mg/kg in A and IN administration of 0.1 mg/kg in B. Total administration of 5 mg/kg is depicted in C and D, with IN baseline of 0.3 mg/kg in C and IN administration of 0.1 mg/kg in D. In all cases, IN plus IP administration was far superior to IP alone and improved versus IN alone. Administration of 0.3 mg/kg CA6261 IN with 1.7 mg/kg IP, or of 0.3 mg/kg CA6261 with 4.7 mg/kg IP showed essentially no virus infection effects and was equivalent to no virus.
Figure 13B:
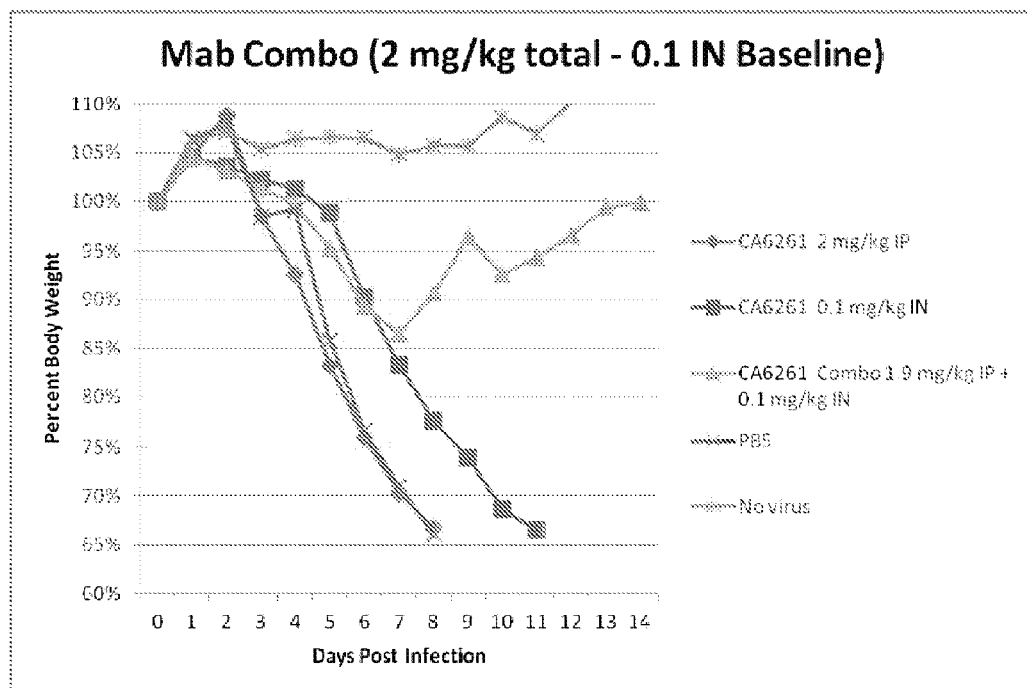
Figure 13C:
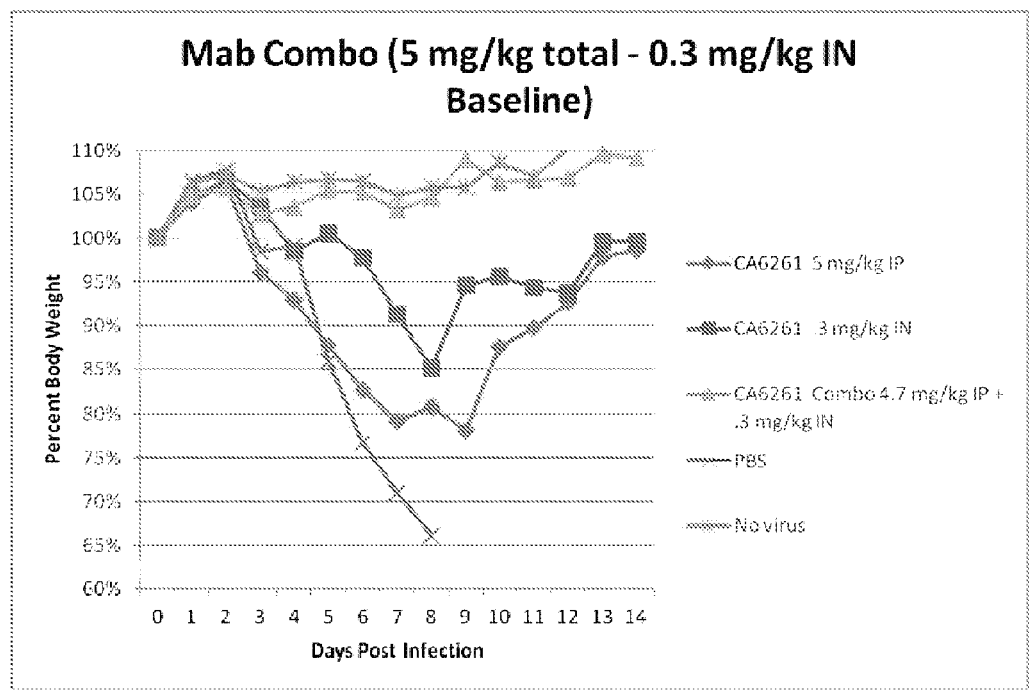
Figure 13D:
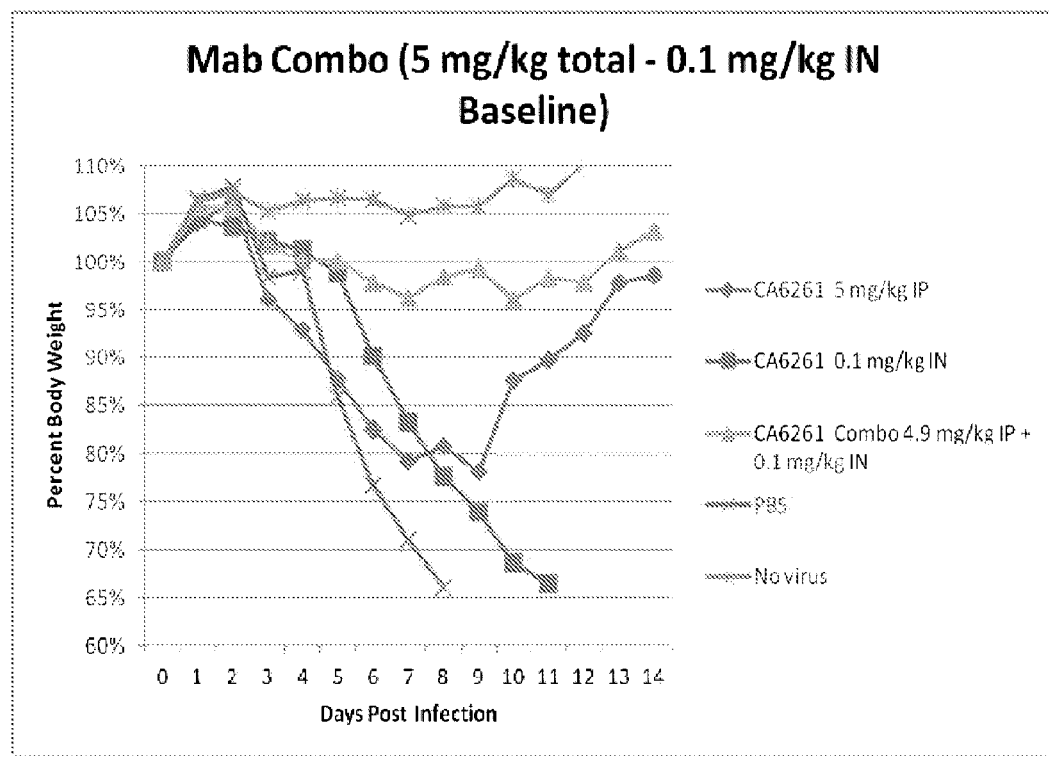

We conclude that the mechanism behind this phenomenon resides in the fact that intranasal delivery achieves a level of IgG antibody in the airway that can utilize the neutralizing capabilities of an antibody, whereas IV or IP delivery of the antibody is Fc dependent. An illustration is shown in FIG. 12. In the airway the inhibitory mechanism relies on the neutralizing characteristics of the antibody and that the Fc dependent effect is severely limited. When giving IgG antibody by IP or IV, the amount of antibody that reaches this space in the airway is too low to capitalize on the neutralizing effect the antibody. For example, when neutralizing antibodies are administered by IP or IV the therapeutic effect that is observed primarily comes from the antibody effector function. We have found comparable levels of efficacy of neutralizing or non-neutralizing antibodies when given IP or IV, but not by IN. To further illustrate that this effect is dependent on neutralization, antibodies against the M2 protein do not exhibit in vitro neutralization and are only capable of exhibiting Fc mediated effects. Previous work using antibodies directed to the M2 ion channel (a more genetically conserved molecule than HA) has shown promise in preclinical models, and has completed phase I studies (TN-032 from Theraclone; NCT01390025, NCT01719874; Grandea A G et al (2010) Proc Natl Acad Sci USA 107(28): 12658-12663). Antibodies against M2 protein cannot neutralize the virus, but can have well documented therapeutic efficacy mediated through effector function (Wang, R. et al. (2008) Antiviral research 80:168-177; Grandea, A. G., 3rd et al. (2010) Proc Natl Acad Sci USA 107(28):12658-12663). We believe that both neutralizing and non-neutralizing antibodies when given IP or IV function primarily through effector function similar to M2 targeted antibodies. We note that it is known that the M2 protein is significantly less abundant than HA, and also does not protrude from the surface. Antibodies against HA can neutralize the virus offering the potential for further improved efficacy. As such, typically antibodies to HA are more therapeutically effective than anti-M2 antibodies. Nonetheless antibodies that are not neutralizers and still target HA can exhibit comparable levels of efficacy as neutralizing antibodies when given IP, suggesting that this route of delivery fails to capitalize on the potent effect that can be harnessed when given IN. Furthermore, delivery of neutralizing Fabs through IN but not IP result in therapeutic efficacy. Non-neutralizing Fabs given IN do not exhibit therapeutic efficacy. All together, only neutralizing antibodies given IN exhibit this increased efficacy. Extending this observation, this phenomenon will occur for neutralizing antibodies that target other proteins (eg neuraminidase) and to neutralizing antibodies against other respiratory pathogens (eg palivizumab for RSV). As delivery of antibodies both by the IN and IP/IV routes can be effective in different ways on their own, we believe that the use of both routes in combination will harness the maximum therapeutic potential of a neutralizing antibody. This approach will allow maximal efficacy by utilizing the increased neutralization activity through the IN route, and increased Fc dependent activity by IP/IV route.

Materials and Methods

The following provides Materials and Methods for the Examples provided herein.

Antibodies:

Mabs 6P15, 1P19, and 1K17 were isolated using phage display as described below and are broadly-reactive anti-H3 antibodies and do not neutralize virus by microneutralization assay, plaque reduction assay, or HI. Mabs CR8020 and CR6261 are well characterized broadly-reactive antibodies against group 2 and group 1 viruses, respectively (Throsby M et al (2008) PL0S ONE 3:e3942; Eckert D C et al (2009) Science 324:246-251; Friesen R H E et al (2010) PLoS ONE 5(2):e1906; U.S. Pat. No. 8,192,927; Eckert D C et al (2011) Science 333:843-850). Antibody CR9114 binds a conserved epitope in the HA stem and protects against lethal challenge with influenza A and B viruses when administered IV (Dreyfus C et al (2012) Science Express 9 Aug. 2012 10.1126/science.1222908). These neutralizing antibodies were cloned in our hands by synthesizing the variable region and subcloned into mouse IgG2a expression vectors. The variable region of CR8020 was cloned using the published heavy chain GI: 339779688 and light chain GI: 339832448. The variable region of CR6261 was cloned using the published heavy chain GI: 313742594 and light chain GI: 313742595. The variable region of CR9114 was cloned using the Genbank sequence heavy chain accession JX213639 and light chain accession JX213640. All Mabs utilized in these studies are cloned into IgG expression vectors containing the human variable regions fused to mouse IgG2a. The chimeric antibodies for mouse antibodies CR6261, CR8020 and CR9114 are referenced as CA6261, CA8020 and CA9114 herein respectively. Mabs 6F12 and GG3 are from mouse hybridomas that bind to and neutralize group 1 and anti-H1 viruses (Wang T T et al (2010) PLoS Pathog 6(2):e1000796; Tan G S et al (2012) J Virol 86(11): 6179-6188; US Application 20110027270). Mab 5A7 binds to a common epitope on B virus HA and neutralizes virus, and protects mice from lethal challenge when given IP (Yasugi M et al (2013) PLoS Pathog 9(2): e1003150, doi: 10.1371/journal.ppat.1003150). Human antibody Mab53 (also denoted TRL53) is described in US2012/0020971 and WO2011/160083 and is effective in neutralizing Group 1 and 2 H1, H9, H7 and H5 subtypes. The antibody Mab579 (also denoted TRL579) is described in WO2013/086052 and is effective in neutralizing H3 and H7. Published sequences including antibody heavy and light chain variable regions sequences, and particularly heavy and light chain CDR domain (CDR1, CDR2 and CDR3) sequences of above noted and exemplified antibodies herein, particularly including CR6261, CR8020, CR9114, 5A7, Mab53 and Mab579, are known and publicly available, including in references noted above and incorporated herein by reference.

Phage Display:

Antibody fragments were selected by multiple rounds of panning against recombinant hemagglutinin (HA) (Immune Technologies Corp, New York) of influenza or sucrose cushion purified influenza virus. In brief, antigen was diluted in PBS and incubated overnight at 4° C. on MaxiSorp Nunc-Immuno plates (Nunc). Plates were washed twice with PBS. Plates were incubated with 5% milk in PBS for 2 hrs at room temperature with constant shaking. Phage library was blocked in 2.5% Milk in PBS with 2.5% fetal bovine serum and 0.005% tween. The blocked phage was added to the blocked plates for 2 hrs at room temperature on a shaking platform at approximately 400 rpm. Plates were washed with PBST and bound phage were eluted in DTT elution buffer. Eluted phage were incubated with TG1 cells for 45 min at 37° C. Cells were plated onto 15 cm culture plates containing LB, chloramphenicol (Cam), and glucose (Glc) and incubated overnight at 30° C. Colonies were scraped from plates and precipitated with polyethylene glycol for subsequent rounds of panning. Three or four rounds of panning were performed using either an HA antigen from the same strain or on an HA of a different strain. The final round of panning was plated onto larger Q trays for Q-pix colony picking into 384 well plates.

Fab Validation:

Fab encoding phage lysates were screened by ELISA against recombinant HA. Single colonies picked into 384 well plates containing 2 XYT/Cam/Glc media were grown overnight at 30° C. TG1 cells in 384 well plates were replicated into 384 well expression plates containing 2 XYT/Cam with low glucose using Qpix. Plates were grown for 2-4 hrs at 30° C. and 400 rpm. Fab expression was induced with 0.5 mM IPTG and grown overnight at 22° C. and 400 rpm. Fab-containing cells were lysed with BEL buffer containing Benzonase at 22° C. and 400 rpm for 1 hr. Fab-containing lysates were blocked with 12.5% MPBST for 30 min at 400 rmp and 22° C. Lysates were added to HA-coated ELISA plates for 1 hr at RT. Plates were washed five times with PBST and then incubated with anti-Fab IgG conjugated to alkaline phosphatase for 1 hr at RT. Plates were washed five times with TBST and developed with AutoPhos (Roche, N.J.). Plates were read using an Infinite Pro F200. Positive phage lysates were sequenced and the unique Fabs were subcloned into Fab expression constructs containing a c-myc and his tag for further characterization.

Fab Expression:

Fab expression plasmids were electroporated into TG1 F-cells and plated onto LB/Cam agar plates. Plates were incubated at 37° C. overnight. 5 ml of 2 XYT/Cam/Glc were inoculated with a single colony and grown overnight at 30° C. and 350 rpm. 500 ml of 2 XYT/Cam/low Glc were inoculated with 2 ml of overnight culture and shaken at 30° C. and 180 rpm until an OD600 nm of 0.5 was reached. Fab expression as induced by addition of IPTG at a final concentration of 0.75 mM. Cultures were shaken at 30° C. and 160 rpm overnight. Cultures were centrifuged for 30 min at 5,000 g and 4° C. Bacterial pellets were frozen at −80° C. for least 2 hrs. Cells were lysed and filtered on 0.22 um filter and subjected to IMAC purification and a size exclusion step.

Cloning and Expression of Antibodies:

Fab encoding phage were sequenced and subcloned into IgG expression plasmids for the respective heavy and light chains. IgGs were produced in Invitrogen 293F or Invitrogen 293Expi cells in shaker flasks. Cells were transfected with expression plasmids for the heavy and light chains. Culture supernatants were harvested six days post-transfection and purified using Protein A affinity chromatography and a buffer exchange step.

Therapeutic Efficacy Studies in Mice:

Female 6-7 weeks old BALB/c mice were used in all experiments. All mice were acclimated and maintained for a period of at least three days prior to the start of the experiment. Mice were weighed on the day of virus challenge and then daily for 2 weeks. A clinical scoring system was used as criteria for clinical endpoint and removal from the study. Clinical signs were scored as follows: hunched posture=3, piloerrection=3, no eating or drinking=2, weight loss≥30%=10, neurological symptoms=10. Mice were removed from the study and euthanized when reaching a score of 16 or more. Animal studies were conducted per approved Institutional Animal Care and Use Committee protocols. Therapeutic treatment of mice was performed on indicated days post infection. Mice were first anesthetized with a ketamine/xylazine mixture prior to intranasal administration of virus, Mab, or Fab in 50 ul of volume per mouse. Peritoneal administration of Mab or Fab was given in 100 ul volume. Mean body weight was determined for each day during the 14 day study period and shown relative to the mean body weight on day 0.

Viruses:

Strains of influenza virus (including A/California/7/09, A/Victoria/11) were mouse-adapted according to Cottey, Rowe, and Bender (Current Protocols in Immunology, 2001). Three rounds of mouse adaptation were performed followed by one round of propagation of virus in embryonated eggs. In brief, three 6-8 week old mice were anesthetized and infected intranasally with 20 ul of virus. Three days post infection, mice were euthanized and lungs were removed. Lungs were mechanically homogenized, clarified, and centrifuged to remove large pieces of debris. Additional passaging into naïve mice of 20 ul of lung homogenate were performed for three rounds.

REFERENCES

Huber V C, Lynch J M, Bucher D J, Le J, Metzger D W: Fc receptor-mediated phagocytosis makes a significant contribution to clearance of influenza virus infections. J Immunol 2001, 166:7381-7388.

Jegerlehner A, Schmitz N, Storni T, Bachmann M F: Influenza A vaccine based on the extracellular domain of M2: weak protection mediated via antibody-dependent NK cell activity. J Immunol 2004, 172: 5598-5605.

Feng J, Mozdzanowska K, Gerhard W: Complement component C1q enhances the biological activity of influenza virus hemagglutinin-specific antibodies depending on their fine antigen specificity and heavy chain isotype. J Virol 2002, 76:1369-1378.

Mozdzanowska K, Feng J, Eid M, Zharikova D, Gerhard W: Enhancement of neutralizing activity of influenza virus-specific antibodies by serum components. Virology 2006, 352:418-426.

EXAMPLE 2

Neutralizing Antibodies are Effective Intranasally Experimental Studies

Figure 2:
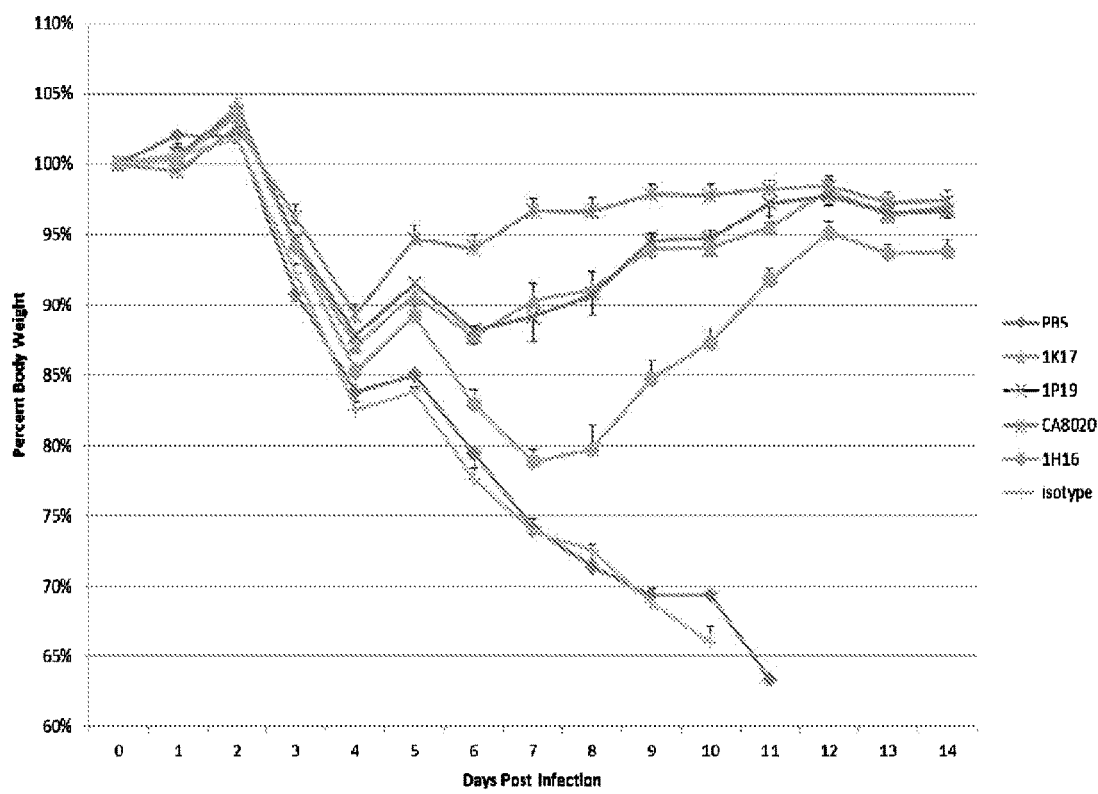
FIG. 2 IP delivery of neutralizing and non-neutralizing MAbs are prophylactically effective. Animals were inoculated with 10×LD50 of H3 influenza virus VIC/11 MA and treated 1 hour before infection (−1 hpi) with 10 mg/kg IP of various noted antibodies—1K17, 1P19, 1H16 (all non-neutralizing) and CA8020 (neutralizing)—and PBS or isotype control antibody control. Animals (10 animals in each group) were monitored for body weight each day for 14 days post infection and percent body weight of original day 0 weight is plotted.
Figure 3:
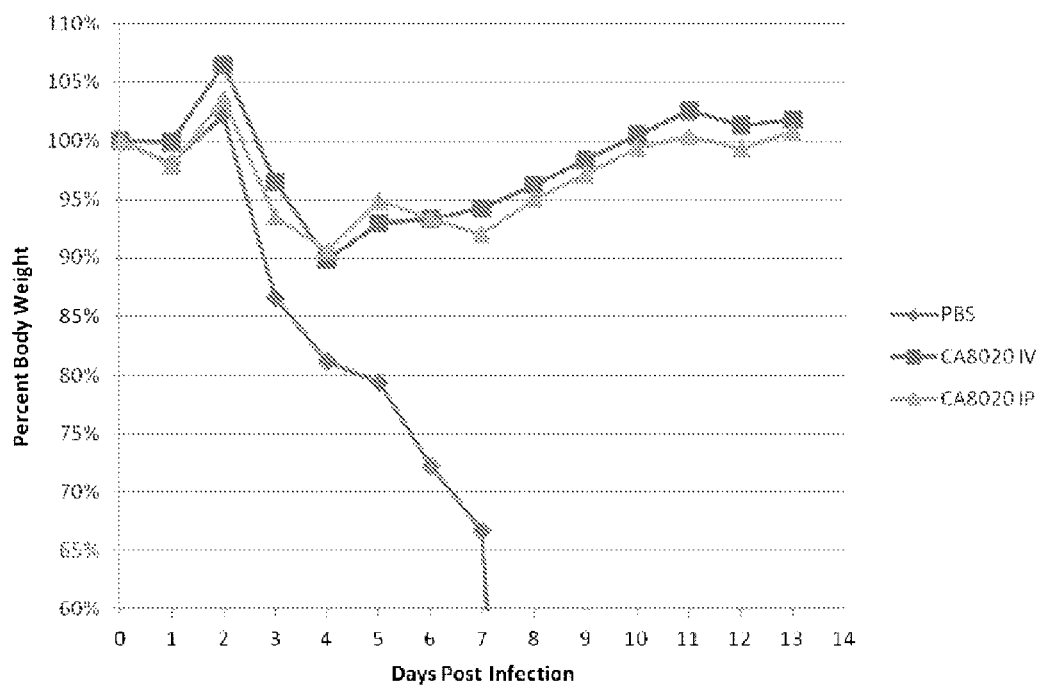
FIG. 3 Antibody given IV or IP showed similar efficacy. Animals were inoculated with 10×LD50 of H3 influenza virus VIC/11 MA and treated 1 hour post infection (1 hpi) with 10 mg/kg of antibody CA8020 IP or IV with PBS as control. Animals were monitored for body weight each day for 14 days post infection and percent body weight of original day 0 weight is plotted.

The therapeutic efficacy of systemically delivered antibodies is not solely reliant on neutralization capability, as both neutralizing and non-neutralizing antibodies given by IP route exhibit similar effects in treating and preventing lethal infection. Neutralizing and non-neutralizing antibodies were similarly effective when administered IP 10 mg/kg 24 hours post infection (24 hpi) (FIG. 1). The results shown in FIG. 1 demonstrate that systemically delivered antibodies against HA can exert robust therapeutic efficacy through effector function, as several non-neutralizing antibodies (6P15, 1P19 and 1K17) protect mice from lethal challenge to a similar degree as the neutralizing antibody CA8020. Neutralizing and non-neutralizing antibodies are similarly prophylactically effective given IP 1 hour prior to infection −1 hpi) with virus (FIG. 2). Similar results were seen at 1 hpi and using different viruses (data not shown). These results bring into question whether neutralization contributes significantly to therapeutic efficacy during systemic delivery. Delivery of antibodies by IV or IP route did not result in significant efficacy differences (FIG. 3 and data not shown).

Figure 4:
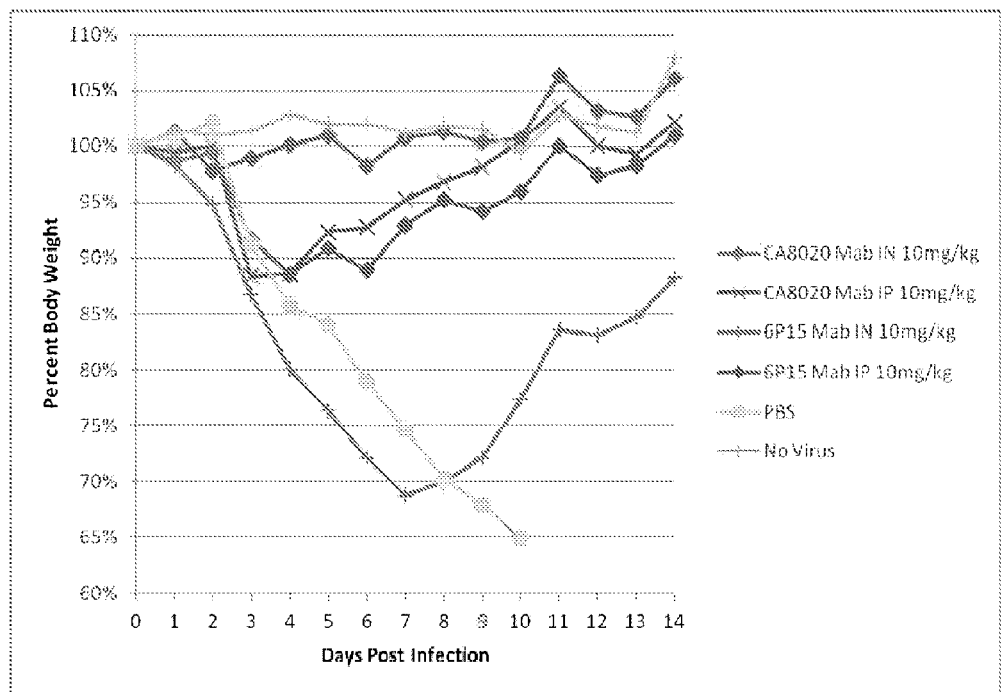
FIG. 4 shows a comparison of neutralizing and non-neutralizing antibodies intranasal (IN) administration versus intraperitoneal (IP) administration. Animals were inoculated with 10×LD50 of H3 influenza virus VIC/11 MA and treated 24 hpi with 10 mg/kg of neutralizing antibody CA8020 IN or IP or with non-neutralizing antibody 6P15 IN or IP, with PBS as control. When giving a neutralizing Mab IN, therapeutic efficacy increased compared to IP administration of the same dose of the same antibody. In contrast, when giving a non-neutralizing Mab IN, therapeutic efficacy is decreased compared to IP at the same dose. Animals were monitored for body weight each day for 14 days post infection and percent body weight of original day 0 weight is plotted.

In contrast, IN delivery of neutralizing antibodies significantly enhanced their therapeutic efficacy compared to systemic delivery (FIG. 4). This boost in therapeutic efficacy is specific to neutralizing antibodies, as non-neutralizing antibodies do not display a similar enhanced therapeutic efficacy. FIG. 4 shows that the ability of a Mab (CA8020) to exhibit enhanced efficacy by IN delivery is dependent on its neutralization ability. Neutralizing Mabs specific for H3 virus exhibit increased efficacy by the IN route but non-neutralizing Mabs do not show such efficacy. Unlike IP delivery seen in FIG. 1, IN delivery of neutralizing antibodies offers significant therapeutic benefit compared to non-neutralizing antibodies. This enhanced efficacy of IN therapy correlates with the ability of an antibody to neutralize, as non-neutralizing antibodies such as 6P15, 1K17, and 1P19 do not exhibit improved therapeutic efficacy IN. Conversely, the non-neutralizing Mabs exhibit a markedly reduced efficacy when administered by IN compared to IP. As seen in FIG. 4, non-neutralizing antibodies (exemplary antibody 6P15) given IP at 10 mg/kg can protect mice from 10×LD50 at 24 hpi similar to neutralizing antibodies at similar doses. However non-neutralizing antibodies do not demonstrate increased therapeutic efficacy when administered by IN route. Representative data of a non-neutralizing antibody 6P15 is shown as an example. Similar results were seen for other non-neutralizing antibodies, including antibodies 1K17 and 1P19 (data not shown).

Figure 14:
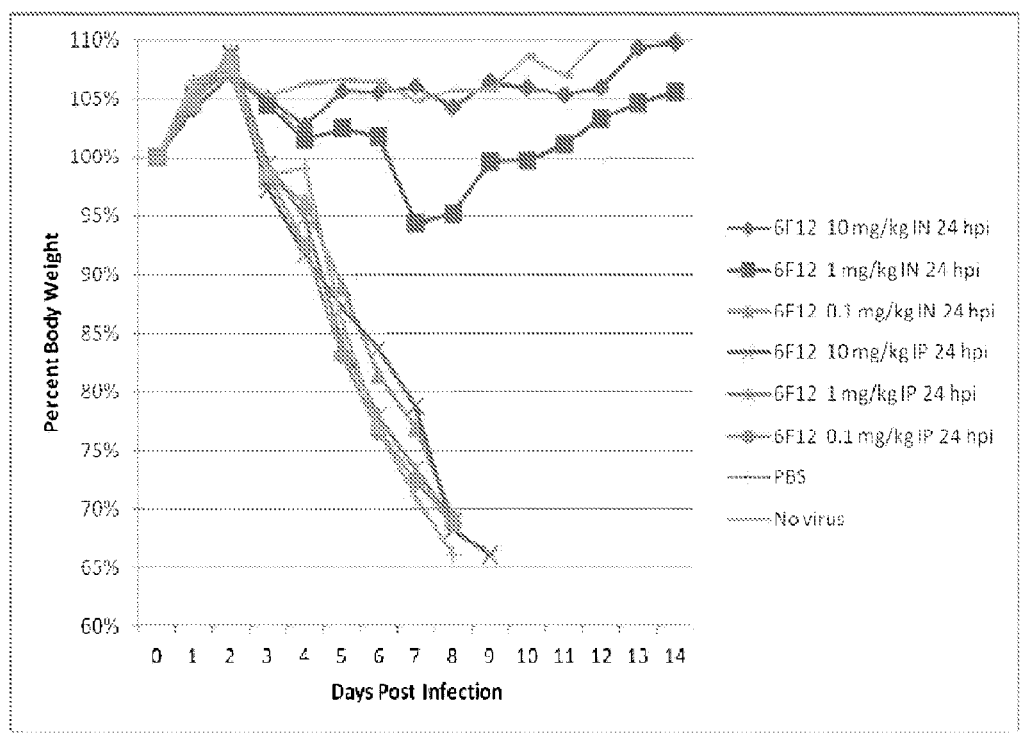
FIG. 14 provides results comparing IN versus IP administration of 6F12 antibody in therapeutic efficacy against H1 virus. Animals were inoculated with 10×LD50 of H1 influenza virus PR8 and treated 24 hpi with 10 mg/kg, 1 mg/kg and 0.1 mg/kg of 6F12 administered IN or IP, with PBS and no virus as controls. Animals were monitored for body weight daily for 14 days post infection and percent body weight of original day 0 weight is plotted. Equivalent doses of Mab 6F12 antibody administered IN demonstrated greater efficacy that comparable IP dose. 6F12 administered IN at doses 1 mg/kg 24 hpi completely protected animals from infection.
Figure 15:
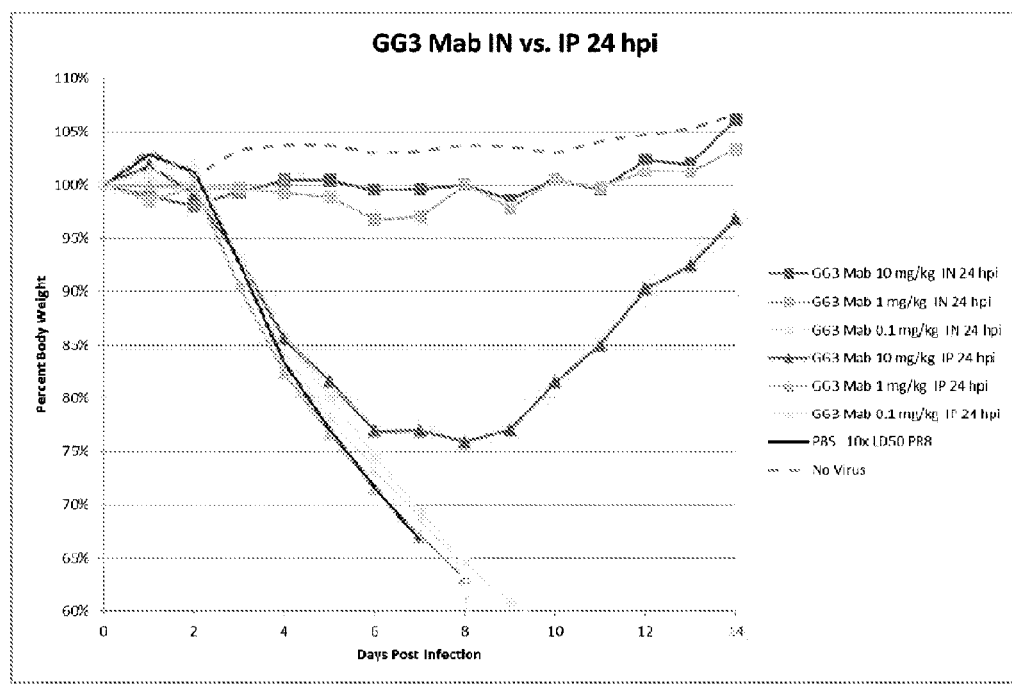
FIG. 15 depicts IN and IP comparison at comparable doses and shows that Mab IN is between 10 and 100 fold more potent than the same Mab administered IP. Animals were inoculated with 10×LD50 of H1 influenza virus (A/Puerto Rico/8/1934) and treated IN or IP 24 hpi with 10 mg/kg, 1 mg/kg and 0.1 mg/kg of neutralizing GG3 Mab, with PBS and no virus as controls. Animals were monitored for body weight daily for 14 days post infection and percent body weight of original day 0 weight is plotted.
Figure 16:
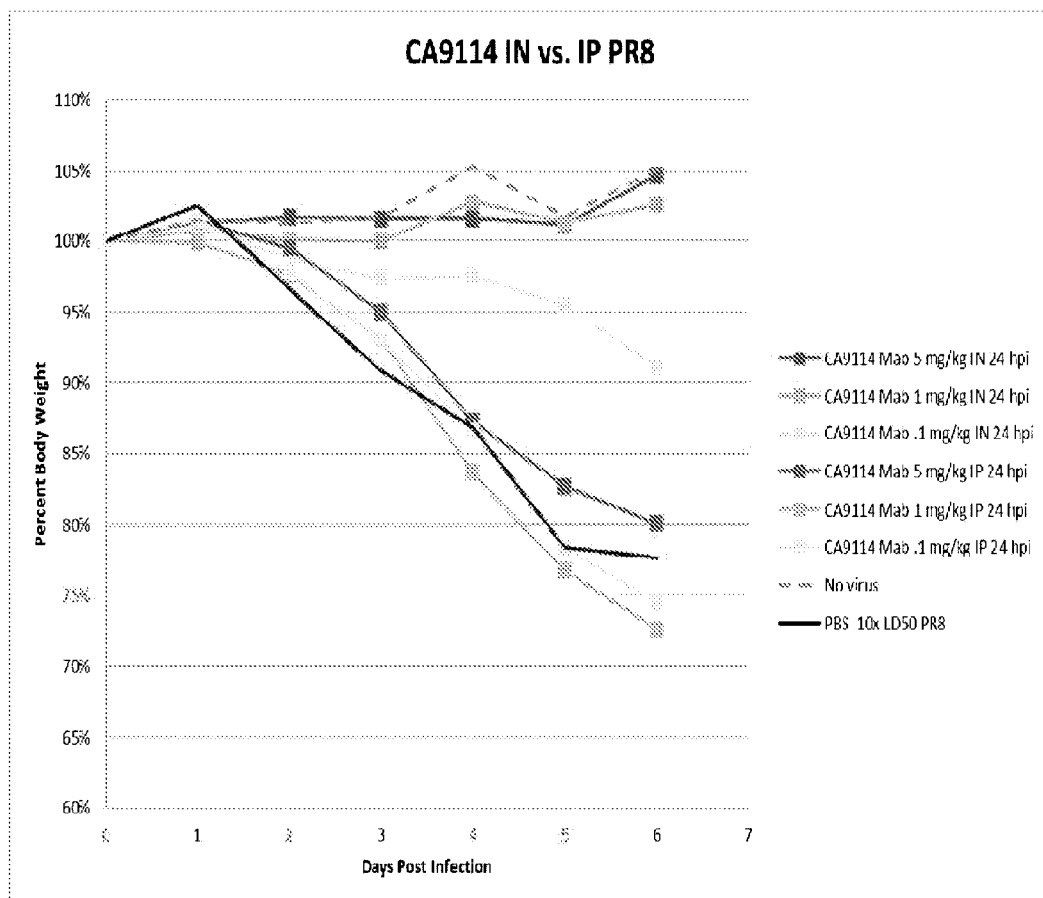
FIG. 16 depicts IN and IP comparison at comparable doses and shows that Mab IN is between 10 and 100 fold more potent than the same Mab administered IP. Animals were inoculated with 10×LD50 of H1 influenza virus (A/Puerto Rico/8/1934) and treated IN or IP 24 hpi with 10 mg/kg, 1 mg/kg and 0.1 mg/kg of neutralizing CA9114 Mab, with PBS and no virus as controls. Animals were monitored for body weight daily for 14 days post infection and percent body weight of original day 0 weight is plotted.

IN enhanced efficacy is also demonstrated by broadly recognizing antibodies against H1 virus CA6261 (an IgG2a antibody binding the short a helix of HA2 subunit) (FIG. 7), by antibodies 6F12 (an IgG2b antibody targeting the stalk region of HA) (FIG. 14) and GG3 antibody (FIG. 15) validating the effect for numerous distinct antibodies and establishing that IN efficacy is consistent across neutralizing antibodies directed against multiple influenza virus targets and subtypes. Further validating the IN efficacy effect, we have evaluated another cross-protective antibody CR9114 and shown it to be highly effective IN (FIG. 16). CR9114 binds a conserved epitope in the HA stem and protects against lethal challenge with influenza A and B viruses when administered IV (Dreyfus C et al (2012) Science Express 9 Aug. 2012 10.1126/science.1222908).

Figure 9:
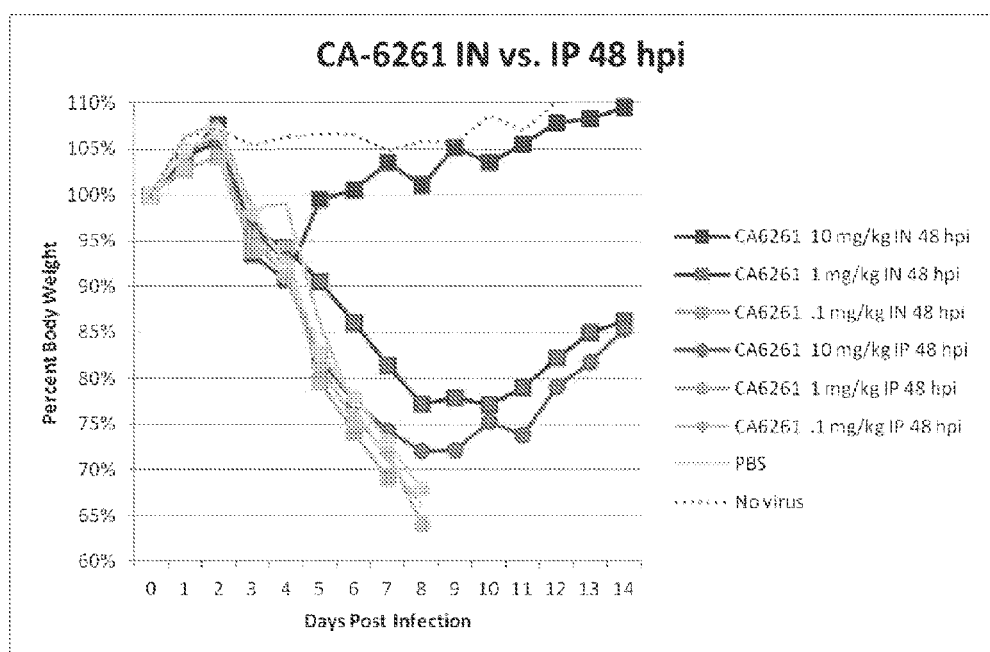
FIG. 9 depicts IN versus IP comparison at comparable doses and shows that Mab IN is still between 10 and 100 fold more potent than the same Mab administered IP when administered 48 hpi. Animals were inoculated with 10×LD50 of H1 influenza virus and treated IN or IP 48 hpi with 10 mg/kg, 1 mg/kg and 0.1 mg/kg of neutralizing CA6261 Mab, with PBS and no virus as controls. Animals were monitored for body weight daily for 14 days post infection and percent body weight of original day 0 weight is plotted.
Figure 17:
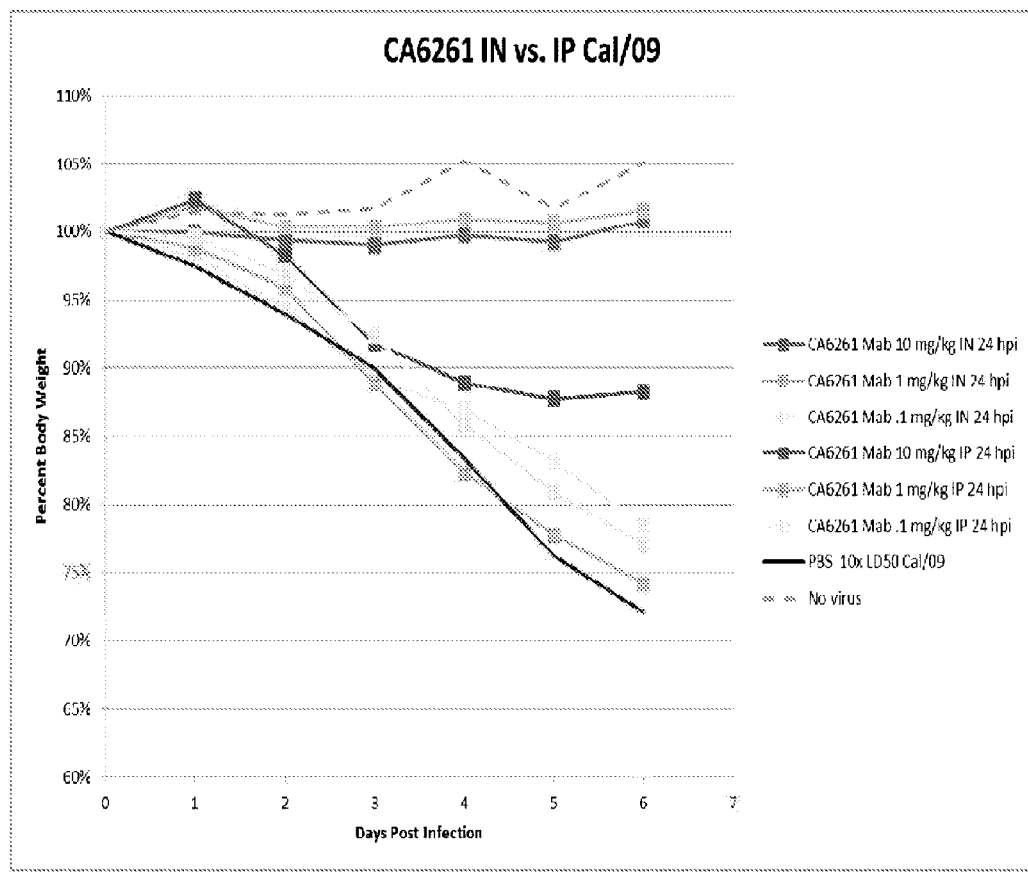
FIG. 17 depicts IN and IP comparison at comparable doses and shows that Mab IN is between 10 and 100 fold more potent than the same Mab administered IP. Animals were inoculated with 10×LD50 of H1 influenza virus (A/California/07/09-mouse adapted) and treated IN or IP 24 hpi with 10 mg/kg, 1 mg/kg and 0.1 mg/kg of neutralizing CA6261 Mab, with PBS and no virus as controls. Animals were monitored for body weight daily for 14 days post infection and percent body weight of original day 0 weight is plotted.

We have not observed a significant difference with regard to antibodies having distinct antibody isotypes as far as intranasal administration. Isotype differences have been observed in IP dosing, suggesting that effector function may be relevant. Also, single neutralizing antibodies were effective in blocking infection against multiple strains of their target H1 or H3 virus, indicating that efficacy is not strain specific or limited. We have demonstrated that neutralizing antibody CR6261 is more than 10 fold more potent by IN than IP against two distinct H1 viruses, specifically PR8 (FIGS. 5, 7 and 9) and mouse adapted Cal/09 (FIG. 17). Thus, IN administration provides a viable and indeed more effective alternative for neutralizing antibodies directed against influenza virus.

EXAMPLE 3

Neutralizing Fabs are Effective Intranasally

Figure 5:
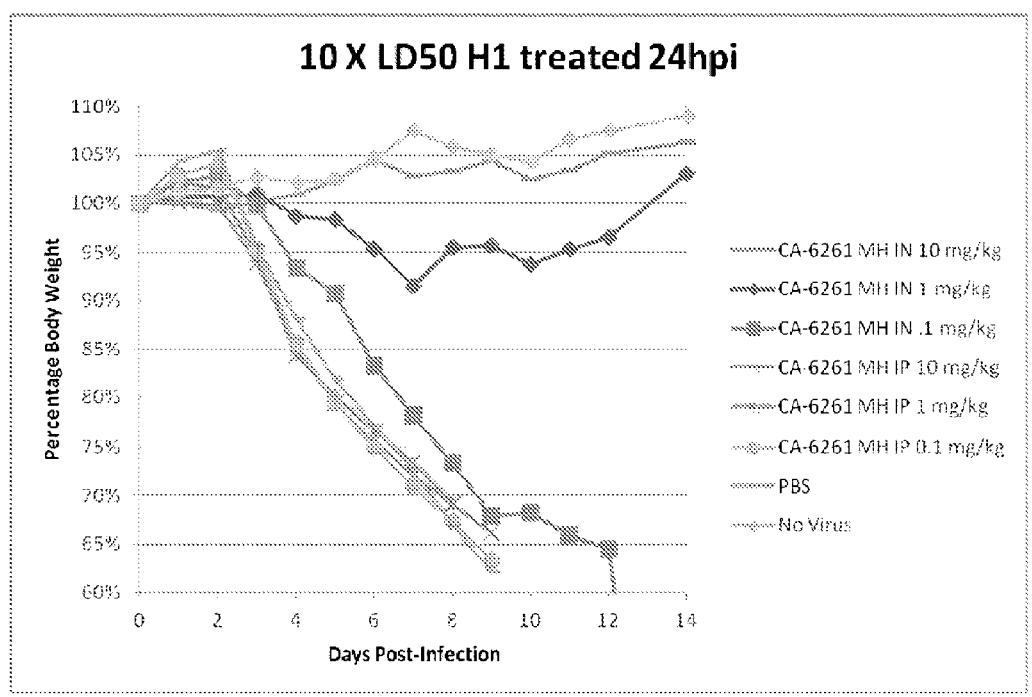
FIG. 5 provides results comparing IN versus IP administration of antibody fragment Fab of CA6261 antibody in therapeutic efficacy against H1 virus. Animals were inoculated with 10×LD50 of H1 influenza virus and treated 24 hpi with 10 mg/kg, 1 mg/kg and 0.1 mg/kg of neutralizing CA6261 Fab administered IN or IP, with PBS treatment and no virus as controls. Animals were monitored for body weight daily for 14 days post infection and percent body weight of original day 0 weight is plotted. All doses of Fab CA6261 antibody administered IN demonstrated greater efficacy that any IP dose. Administration of neutralizing Fab IP did not demonstrate detectable efficacy even at the highest dose, 10 mg/kg.

We next examined whether removal of the Fc will abrogate therapeutic efficacy of IP or IN administered neutralizing and non-neutralizing Fabs. As seen in FIG. 5, IP administered Fab (CA6261 antibody Fab) does not provide therapeutic efficacy against H1 virus at 10 mg/kg or lower. Mice treated with Fab IP all succumbed to infection similar to PBS treated mice. In contrast, mice treated IN with neutralizing Fab at a dose of 10 mg/kg and 1 mg/kg were able to survive lethal infection (FIG. 5). All doses administered IN (even to 0.1 mg/kg) showed greater efficacy than any IP dose administered. Comparable results were observed comparing CA6261 Fab IN versus IP or IV in the same experiment, where Fab CA6261 was not protective or efficacious when administered either IP or IV, but showed significant efficacy (animals retained 95% or greater body weight) when the same dose (5 mg/kg) was administered IN (data not shown). These data demonstrate that Fabs are effective to block or treat viral infection intranasally for neutralizing antibodies. The data further indicate that systemic Mab delivery requires Fc effector function for therapeutic efficacy because Fabs were ineffective.

Figure 6:
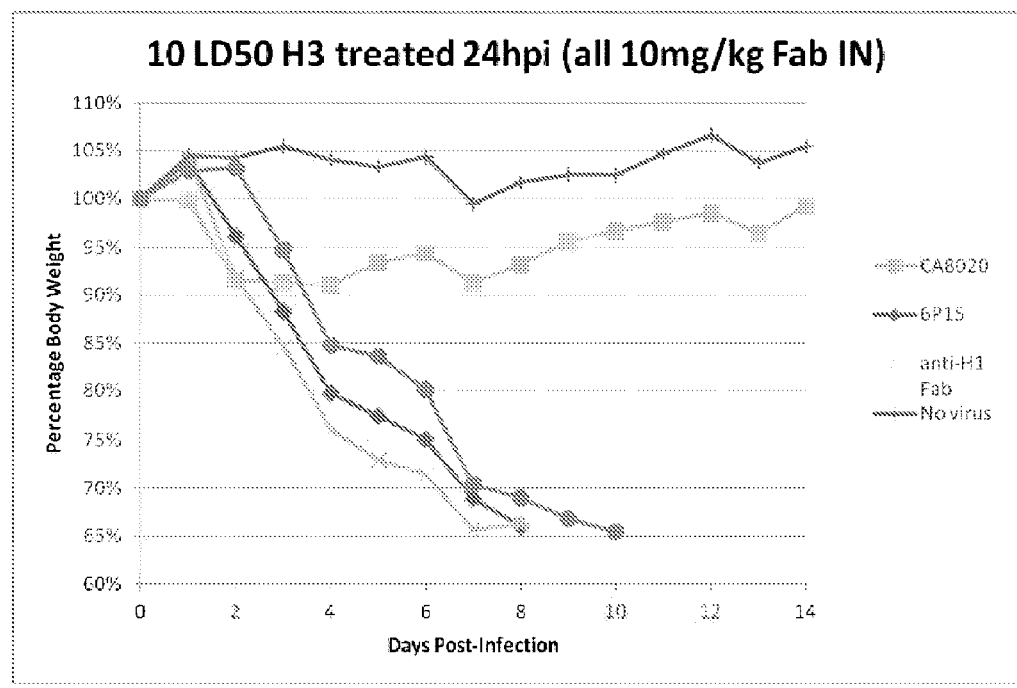
FIG. 6 provides results comparing IN administration of Fab of CA8020 antibody versus Fab of non-neutralizing 6P15 in therapeutic efficacy against H3 virus. Animals were inoculated with 10×LD50 of H3 influenza virus and treated IN 24 hpi with 10 mg/kg of neutralizing CA8020 Fab, non-neutralizing 6P15 Fab, or with a Fab against H1 virus, and no virus as control. Animals were monitored for body weight daily for 14 days post infection and percent body weight of original day 0 weight is plotted. Fab CA8020 antibody administered IN demonstrated efficacy but Fab 6P15 did not.

Fabs from non-neutralizing antibodies do not retain therapeutic efficacy when administered by either IN or IP route. In FIG. 6, mice infected with an H3 virus are treated by IN delivery of purified Fab of exemplary antibodies CA8020 and 6P15. While neutralizing Fabs are able to show therapeutic efficacy, non-neutralizing Fabs are not capable of protecting mice from lethal challenge. These data demonstrate that Fabs from non-neutralizing antibodies do not exhibit therapeutic efficacy when administered IN.

EXAMPLE 4

In Delivery is 10-100 Fold More Potent that IP

Figure 7:
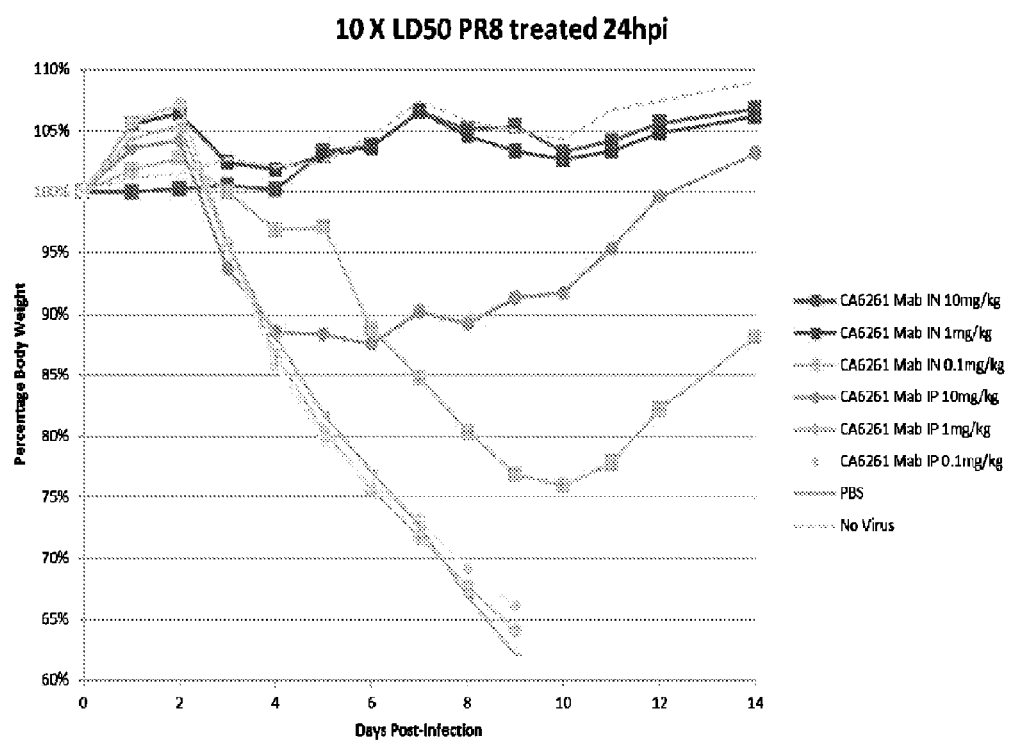
FIG. 7 depicts IN and IP comparison at comparable doses and shows that Mab IN is between 10 and 100 fold more potent than the same Mab administered IP. Animals were inoculated with 10×LD50 of H1 influenza virus (A/Puerto Rico/8/1934) and treated IN or IP 24 hpi with 10 mg/kg, 1 mg/kg and 0.1 mg/kg of neutralizing CA6261 Mab, with PBS and no virus as controls. Animals were monitored for body weight daily for 14 days post infection and percent body weight of original day 0 weight is plotted.

We have discovered that, remarkably, intranasal (IN) delivery of neutralizing antibodies is between 10-100 fold more potent than intraperitoneal (IP) delivery. Mice were infected with 10×LD50 of PR8 virus (H1 virus) and at 24 hpi were treated with antibody (FIG. 7). Neutralizing antibody CA6261 was ten-fold serially diluted and administered either by IN or IP route (FIG. 7A). Mice treated by IN route exhibited less disease severity as indicated by weight loss and were 100% protected from lethal infection at all dilutions. In comparison, only mice treated IP at the highest dose (10 mg/kg) exhibited transient weight loss and protection from lethal infection. All lower dilutions did not protect mice when administered IP. In contrast, IN treatment with a dose of 0.1 mg/kg resulted in transient weight loss and survival of all mice. Mice treated by IN delivery with a dose of 10 mg/kg and 1 mg/kg were protected from detectable weight loss at all times post infection. Antibodies given by IP route at all doses exhibited some degree of weight loss, and only mice treated at the highest dose of 10 mg/kg survived infection.

Figure 8:
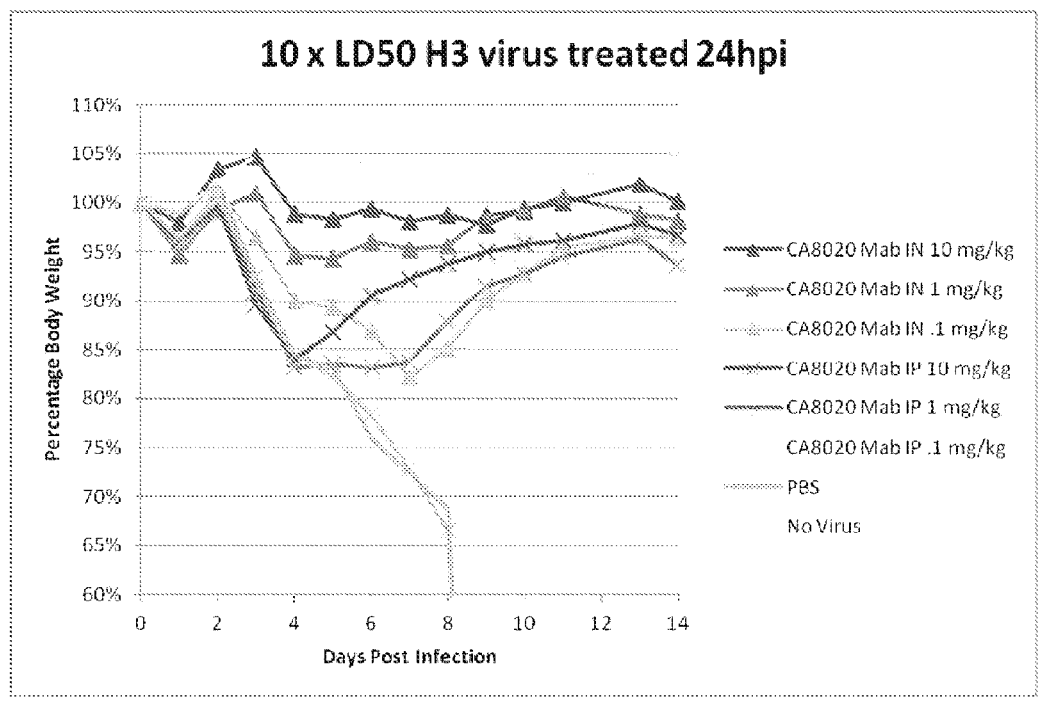
FIG. 8 depicts IN and IP comparison at comparable doses and shows that Mab IN is between 10 and 100 fold more potent than the same Mab administered IP. Animals were inoculated with 10×LD50 of H3 influenza virus and treated IN or IP 24 hpi with 10 mg/kg, 1 mg/kg and 0.1 mg/kg of neutralizing CA8020 Mab, with PBS and no virus as controls. Animals were monitored for body weight daily for 14 days post infection and percent body weight of original day 0 weight is plotted.

We confirmed that intranasal delivery of neutralizing antibodies similarly results in enhanced therapeutic efficacy against H3 viruses. Mice were infected with an H3 virus and treated 24 hpi (FIG. 8). Neutralizing antibody CA8020 was ten-fold serially diluted and administered by IN or IP. As observed in our studies with H1 virus, antibody administered by the IN route provided 100% survival at all dilutions against H3 virus, and exhibited less weight loss than antibodies administered by IP route.

Together these data demonstrate that neutralization is essential for enhanced therapeutic efficacy when delivered IN. Furthermore, therapeutic efficacy of systemically delivered antibodies is not dependent on neutralization, as similar levels of efficacy can be observed for both neutralizing and non-neutralizing antibodies. Supporting this observation, the therapeutic efficacy of a neutralizing Fab is abolished when administered IP, but neutralizing Fab display efficacy when delivered IN. Neutralizing Fabs administered IN display similar improved efficacy compared to IP administration as IN delivery of their full Mab counterpart.

EXAMPLE 5

Intranasal Efficacy Maintained Post-Infection

Figure 18:
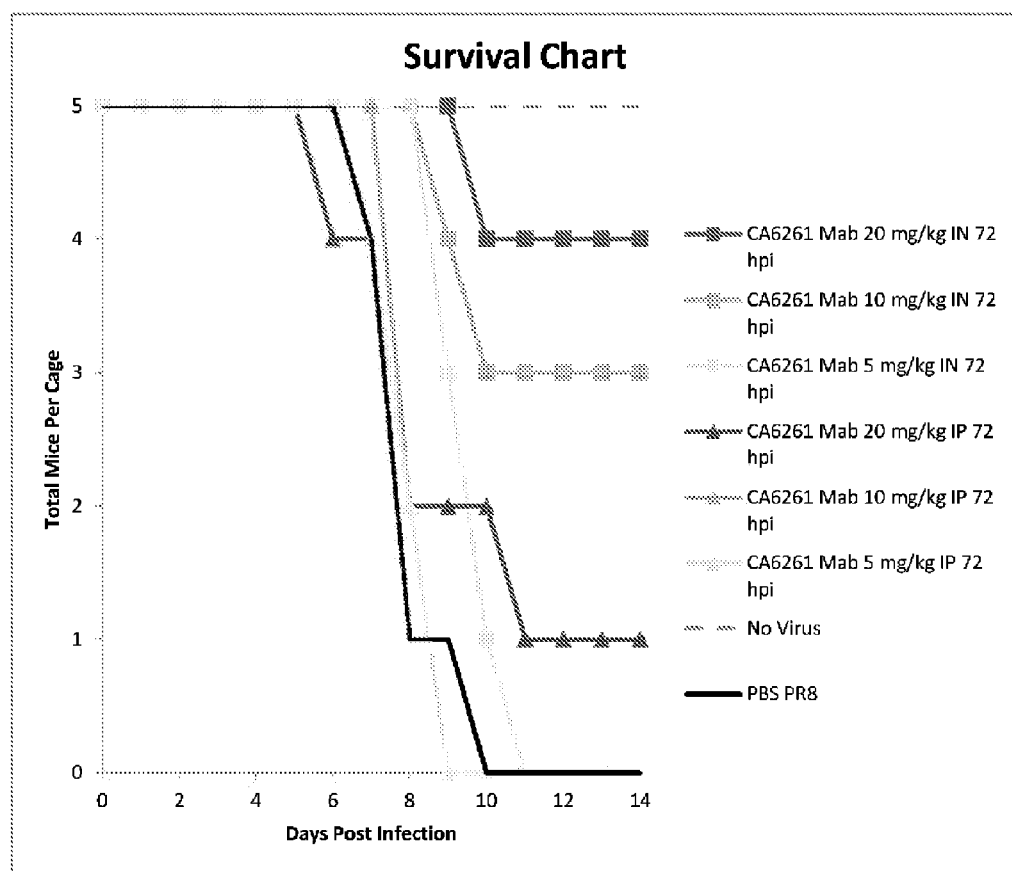
FIG. 18 depicts IN and IP comparison at comparable doses and shows that Mab IN is between 10 and 100 fold more potent than the same Mab administered IP. Animals were inoculated with 10×LD50 of H1 influenza virus (A/Puerto Rico/8/1934) and treated IN or IP 72 hpi with 20 mg/kg, 10 mg/kg and 5 mg/kg of neutralizing CA6261 Mab, with PBS and no virus as controls. Animals were monitored for body weight daily for 14 days post infection and percent body weight of original day 0 weight is plotted.

The enhanced efficacy of IN delivered neutralizing antibody is maintained at later times post infection. In FIG. 8, mice are treated at 48 hpi by either IN or IP. IN delivery of neutralizing antibodies are again more therapeutically effective than IP delivery. Complete protection from lethal challenge is achieved at 1 mg/kg when administered by IN route, whereas IP delivery provides complete protection against lethal challenge at doses of 10 mg/kg. IN dosing showed comparatively reduced efficacy at 72 hpi but remained significantly improved versus IP dosing of the same amount at 72 hpi. A survival chart demonstrating efficacy of CA6261 when administered IN 72 hpi, and very significantly enhanced survival compared to IP at the same doses, is provided in FIG. 18.

EXAMPLE 6

IN Administration Effective at Low Doses

Figure 10:
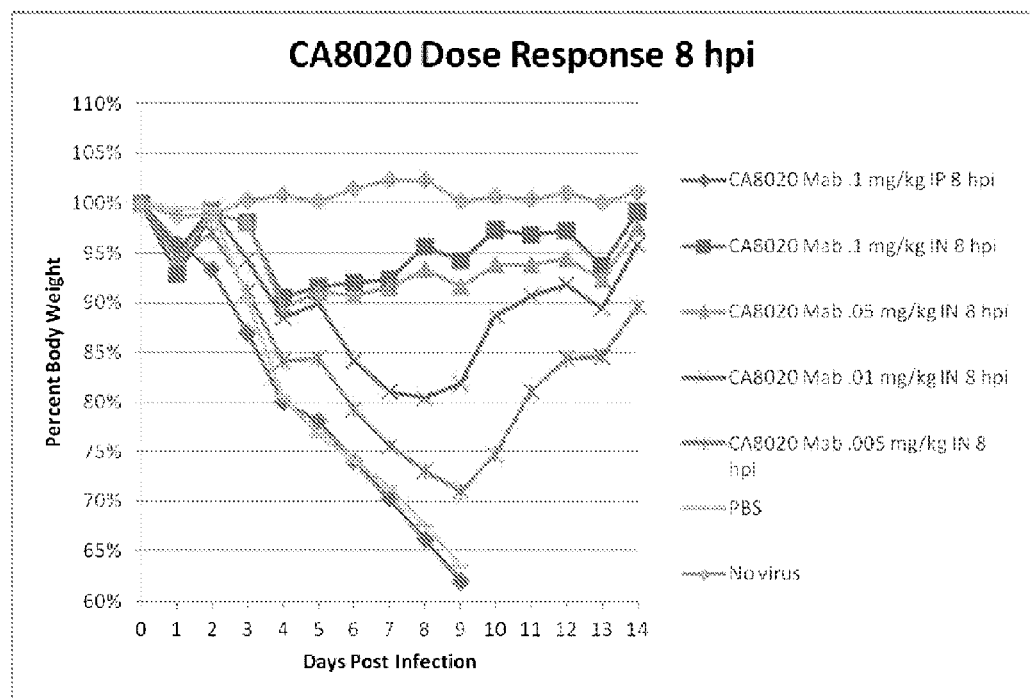
FIG. 10 shows that ultra-low doses are capable of providing protection IN. CA8020 antibody given IN 8 hpi is protective against 10LD50 of H3 virus at doses as low as 0.005 mg/kg. Animals were inoculated with 10×LD50 of H3 influenza virus and treated IN 8 hpi with 0.1 mg/kg, 0.05 mg/kg, 0.01 mg/kg and 0.005 mg/kg of neutralizing CA8020 Mab, IP 8 hpi with 0.1 mg/kg CA8020 Mab, with PBS and no virus as controls. IP dosing at 0.1 mg/kg was equivalent to PBS, showing no effect. All doses IN showed efficacy. Animals were monitored for body weight daily for 14 days post infection and percent body weight of original day 0 weight is plotted.

Intranasal delivery of neutralizing antibodies can provide complete protection against lethal challenge at very low doses when administered after infection. As demonstrated in FIG. 10, IN doses as low as 0.005 mg/kg of CA8020 antibody given 8 hpi result in 100% survival against 10×LD50 of virus. These doses are a thousand fold lower than standard doses for IV or IP treatment post infection. These results indicate that surprisingly low doses when given IN can achieve therapeutic efficacy.

Figure 11:
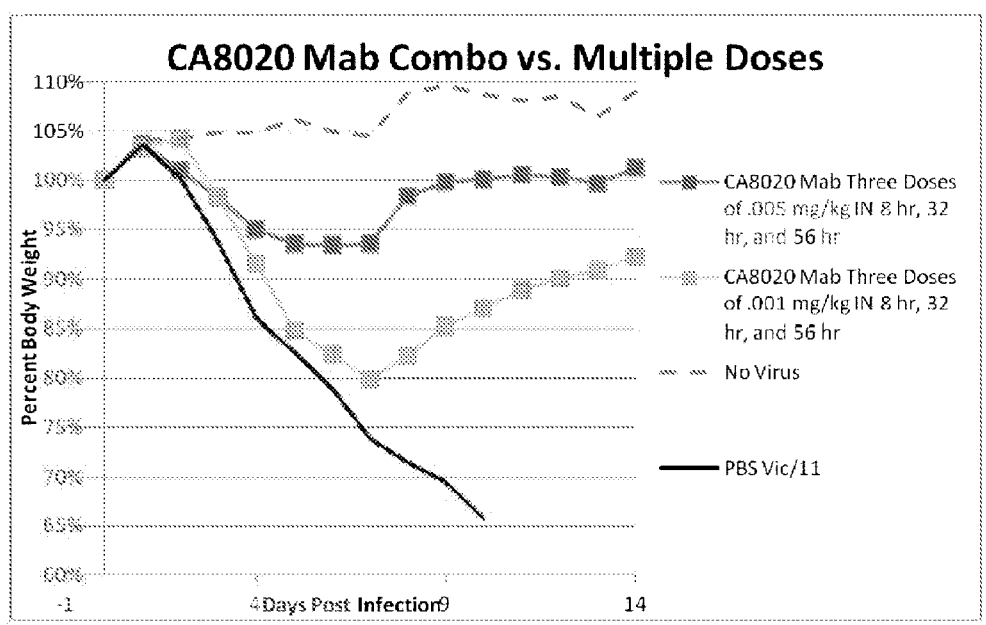
FIG. 11 shows efficacy study of repeated ultralow dosing of neutralizing antibody. Animals were inoculated with 10×LD50 of H3 influenza virus and treated with repeated IN dosing of CA8020 Mab at 8 hpi, 32 hpi and again at 56 hpi. Repeated dosing was conducted at 0.005 mg/kg per dose and at 0.001 mg/kg of neutralizing CA8020 Mab, with PBS and no virus as controls. Both repeated dosing regimens showed efficacy. Animals were monitored for body weight daily for 14 days post infection and percent body weight of original day 0 weight is plotted.

The efficacy of repeated IN dosing was evaluated. Repeated IN dosing of CA8020 Mab at 8 hpi, 32 hpi and again at 56 hpi provided efficacy using low repeated dosing at 0.005 mg/kg per dose and also at repeated dosing of 0.001 mg/kg (FIG. 11). The efficacy was somewhat improved versus a single 8 hpi dosing. Additional studies show protection using antibody CA6261 given 8 hpi are protective at 0.045 mg/kg and lower doses are being evaluated (data not shown).

Together these results show that neutralization is essential for increased IN efficacy, as non-neutralizers do not exhibit the enhanced efficacy. As such, Fabs of neutralizing antibodies when administered via the IN route retain enhanced efficacy whereas Fabs from non-neutralizing antibodies do not exhibit noticeable efficacy. Conversely, neither neutralizing nor non-neutralizing Fabs exhibit efficacy when administered by IP, suggesting that both neutralizing and non-neutralizing Mabs depend on Fc region effector functions when administered IP. An infection model shown in FIG. 12 depicts that enhanced efficacy by IN administration is antibody neutralization dependent whereas systemic delivery relies distinctly on effector function.

EXAMPLE 7

A Combination IN/IP Protocol Provides Enhanced Efficacy

Figure 19:
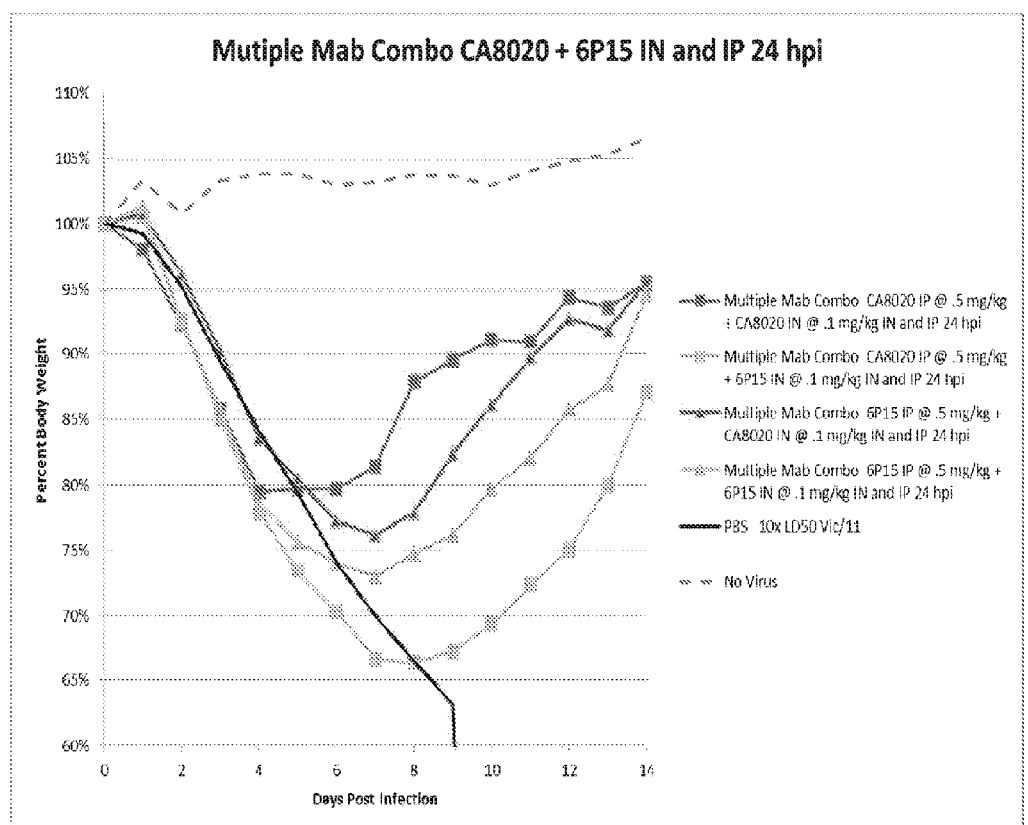
FIG. 19 depicts combination administration studies of IN or IP administration alone versus combination administration of antibody CA8020 or 6P15 by IN and IP routes at 24 hpi with 10×LD50 of H3 virus (Victoria/11). A total administration dose of 0.6 mg/kg is administered, with 0.5 mg/kg IP and 0.1 mg/kg IN. In both cases, IN administration with a neutralizing antibody was superior to IN administration of a non-neutralizing antibody.

Based upon the model, as depicted in FIG. 12, we investigated the hypothesis that IN and IP delivered antibodies display separate, non-redundant functions. If correct, antibodies administered by combined IN and IP routes would exhibit increased efficacy compared to single routes of administration alone. In FIG. 13A through 13D, we show that combined IN and IP delivery is more effective than IP delivery alone, under various combined dosing regimens (total antibody doses in these studies were 5 mg/kg or 2 mg/kg). The improved efficacy provided using combination IN and IP administration compared to the IP or IN groups verifies that the mechanism of action and requirements of Mab administered by IN and IP are distinct and may be non-redundant. Enhanced antiviral efficacy is provided using a combined regimen of IN and IP administration, using a neutralizing antibody for IN and a neutralizing or non-neutralizing antibody for the combined IP administration mode. Further studies demonstrate that IN administration of neutralizing antibody (exemplary CA8020 antibody), combined with IP administration of the same neutralizing antibody or a distinct non-neutralizing antibody (exemplary 6P15) are similarly efficacious, even using low doses 0.1 mg/kg IN and 0.5 mg/kg IP for a total antibody administered of only 0.6 mg/kg (FIG. 19). Implementing an IN administration can reduce overall antibody required for efficacy, even in combination with comparably low doses of antibody IP. The mechanism of action for IN administered antibody may primarily limit spread of the virus, whereas IP administered antibody may primarily reduce the number of infected cells producing virus through effector function.

The mechanism of action was explored by isotype switching of neutralizing antibodies administered by IN or IP. Mouse IgG1 has reduced effector function compared to mouse IgG2a. IN delivered antibodies exhibited similar levels of efficacy independent of isotype as seen for CA6261 and CA8020. IP administered antibodies exhibited marked differences in therapeutic efficacy dependent on isotype. Antibodies of the IgG2a isotype were significantly more effective than mouse IgG1 antibodies for both CA6261 and CA8020 (data not shown). This suggests that the primary mode of action of systemically delivered antibodies is through effector function. As such, known methods for enhancing effector function through various means (for example but not limited to Fc modification or a-fucosylation) would improve efficacy in systemically delivered antibodies and can be included in antibodies delivered by intranasal or inhalation methods. Antibodies delivered by intranasal or inhalation route may activate compliment, engage alveolar macrophages, and/or have limited spread to the basal lateral surface where engagement of effector function may provide improved efficacy.

EXAMPLE 8

Antibody Efficacy Against Influenza B Virus

Figure 20:
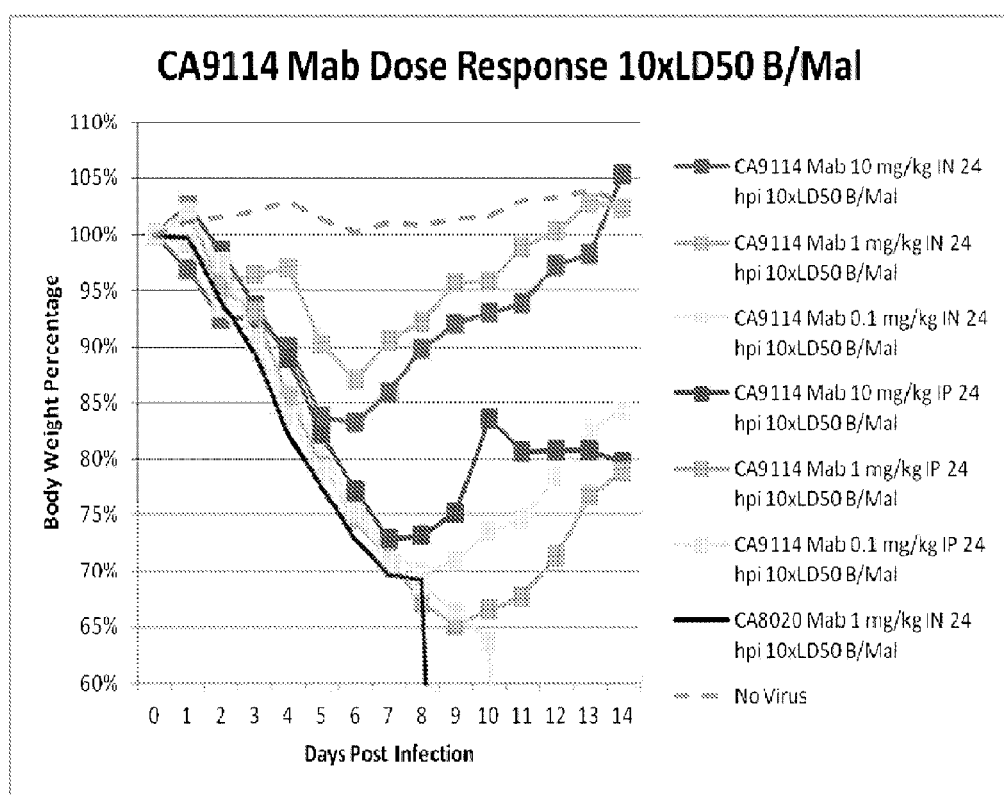
FIG. 20 depicts IN and IP administration of varying doses of CA9114 antibody at 24 hpi with Influenza B virus (B/Malaysia). CA9114 antibody was administered IN or IP at 10 mg/kg, 1 mg/kg or 0.1 mg/kg. Antibody CA8020 and no virus are depicted as controls. Animals were monitored for body weight daily for 14 days post infection and percent body weight of original day 0 weight is plotted.

The antibody CR9114 binds and is effective against influenza type A and also type B viruses, as indicated above and noted in Table 1 and previously reported (Dreyfus C et al (2012) Science 337(6100):1343-1348). Chimeric antibody CA9114 (described above having human variable regions fused to mouse IgG2a) was tested in the mouse model for efficacy against influenza B/Malaysia strain. IN and IP dosing at 10 mg/kg, 1 mg/kg and 0.1 mg/kg was tested 24 hpi for efficacy against 10×LD50 of B/Malaysia (denoted B/Mal). The results are provided in FIG. 20. IN administration was more effective than IP at all doses tested. CA9114 antibody delivered intranasally 1 day post infection with influenza B virus was effective to treat animals and eliminate loss in body weight with influenza virus.

Figure 21:
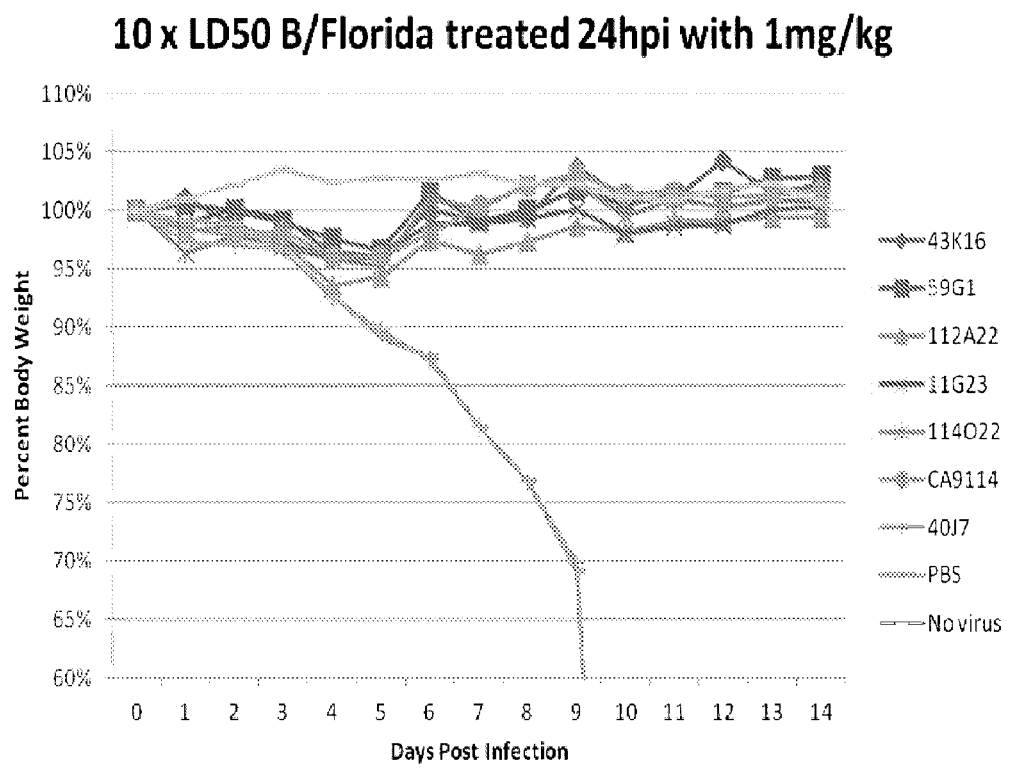
Figure 22:
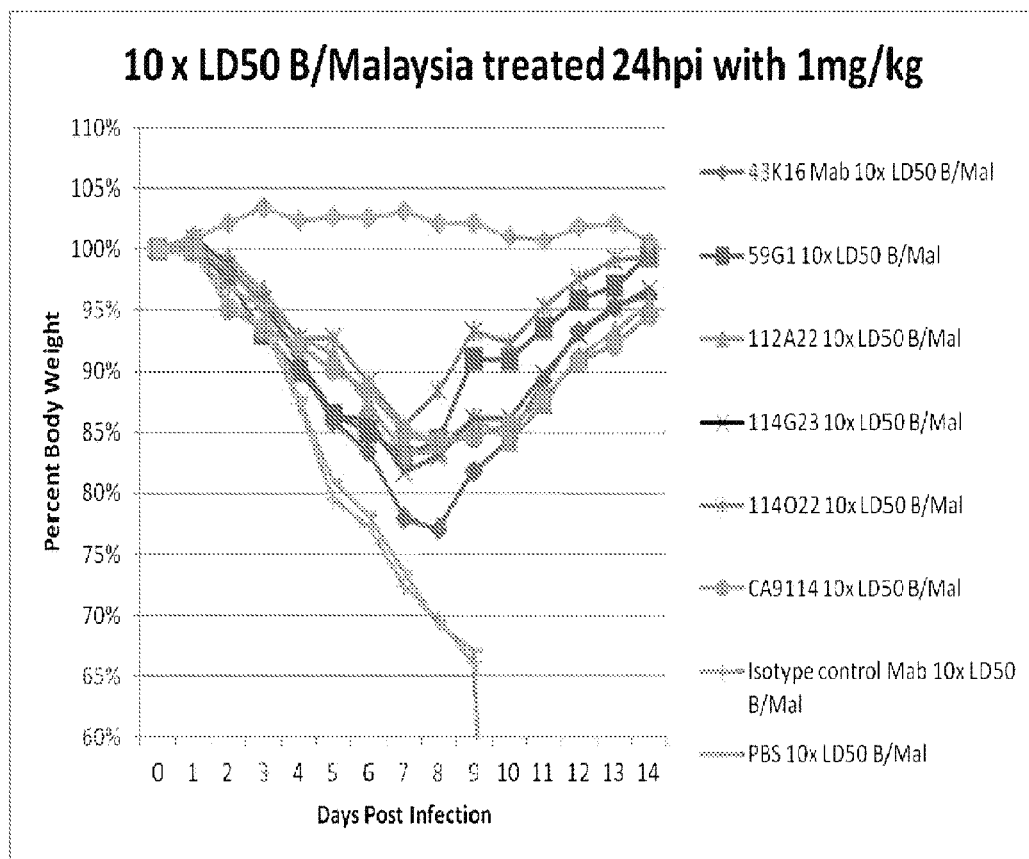
FIG. 22 shows various antibodies against influenza B tested for efficacy against B/Malaysia virus. All antibodies were administered at 1 mg/kg IN 24 hpi with 10×LD50 of B virus. Antibodies tested were 43K16, 59G1, 112A22, 114G23, 114O22 and CA9114. Controls were isotype control Mab, PBS and no virus. Animals were monitored for body weight daily for 14 days post infection and percent body weight of original day 0 weight is plotted.
Figure 23:
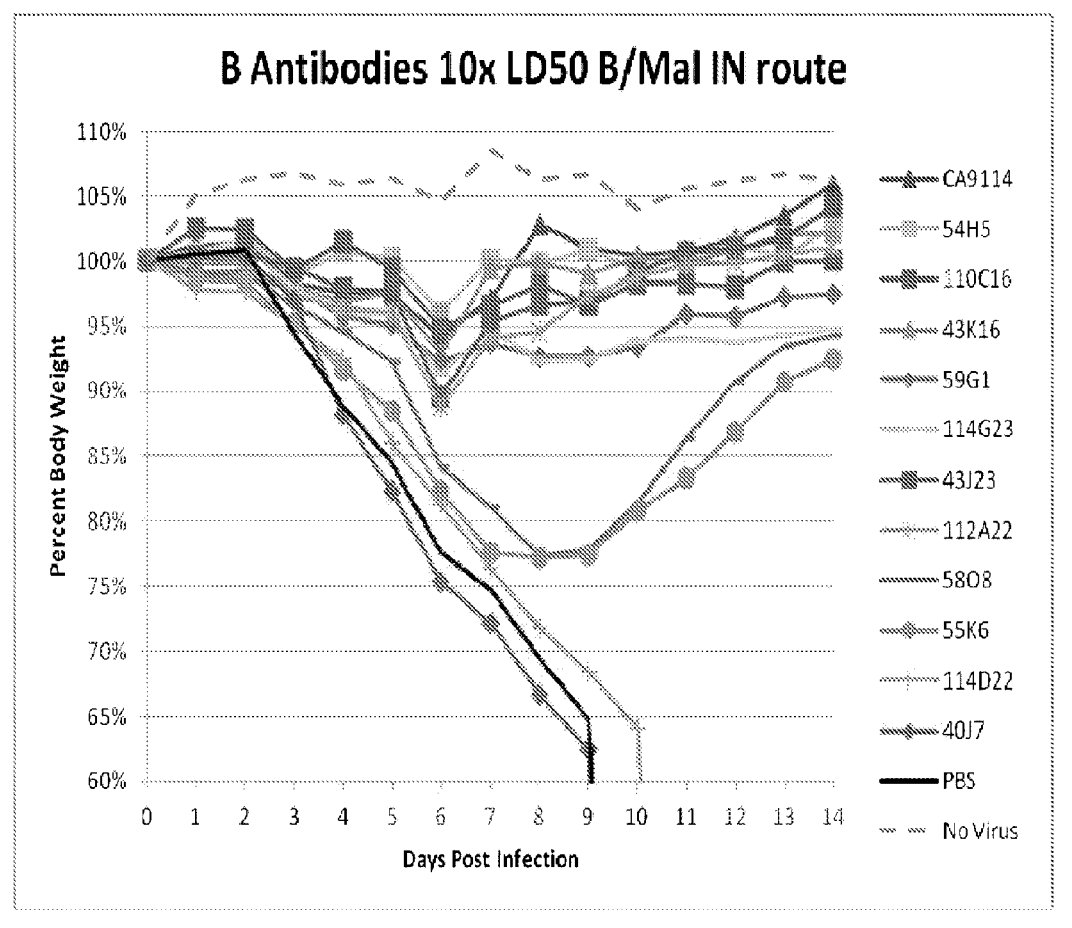

A series of monoclonal antibodies with demonstrated ability to bind and neutralize influenza B type virus in vitro, including numerous B antibodies isolated using phage display as described above and also antibody CA9114, were tested intranasally against B/Florida and B/Malaysia virus. Each antibody was administered IN at 1 mg/kg 24 hpi with 10×LD50 influenza B virus. The results are depicted in FIGS. 21 and 22, showing efficacy of intranasal administration of various monoclonal antibodies against influenza B B/Florida and B/Malaysia in comparison with CA9114 antibody. Similar studies were conducted with CA9114 and various antibodies against B/Mal administered at 1 mg/kg 8 hpi (FIG. 23). All antibodies tested were effective against both B virus types. These studies confirm efficacy of anti-influenza antibodies administered intranasally against influenza B virus, including 8 or 24 hours post infection.

Figure 37:
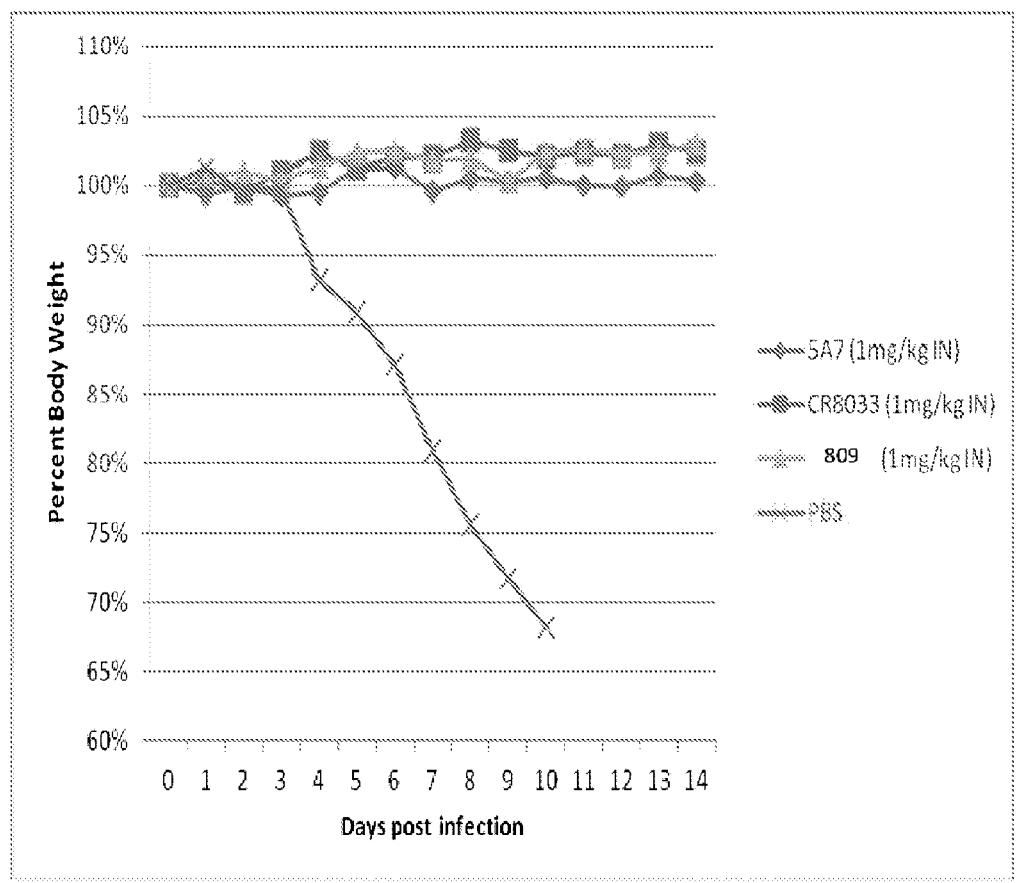
FIG. 37 depicts IN administration of antibodies 5A7, CR8033 and mAb809 at 24 hpi with 10×LD50 Influenza B virus (B/Malaysia/2506/2004). Each influenza B antibody was administered IN at 1 mg/kg. PBS is depicted as a control. Animals were monitored for body weight daily for 14 days post infection and percent body weight of original day 0 weight is plotted.
Figure 38:
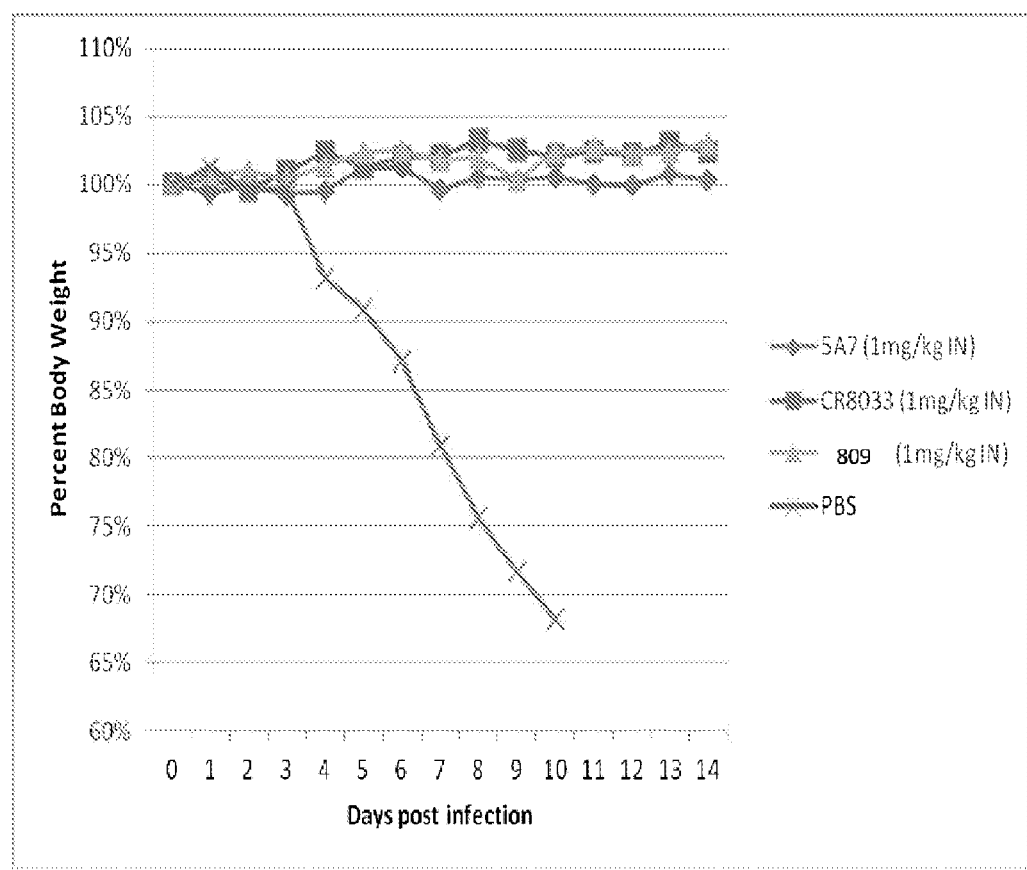
FIG. 38 depicts IN administration of antibodies 5A7, CR8033 and mAb809 at 24 hpi with 10×LD50 Influenza B virus (B/Florida/05/2006). Each influenza B antibody was administered IN at 1 mg/kg. PBS is depicted as a control. Animals were monitored for body weight daily for 7 days post infection and percent body weight of original day 0 weight is plotted.

Additional influenza B antibodies were tested for efficacy in animals infected with B/Florida or B/Malaysia virus. Antibodies 5A7, CR8033 and mAb809 were evaluated by administration IN at 1 mg/kg 24 hpi with 10×LD50 of B virus, either B/Malaysia virus or B/Florida virus (FIG. 37 and FIG. 38, respectively). All IN administered anti-influenza B antibodies were fully efficcious against infection with either B lineage virus at a 10×LD50 dose, with antibody-treated infected animals retaining 100% body weight.

EXAMPLE 9

Combination Antibody Studies

Current influenza vaccines include antigens to induce immunity to circulating influenza virus strains in the human population. Quadrivalent influenza vaccines cover influenza A viruses, particularly subtype H1 virus and H3 virus, and also influenza B virus Yamagata and Victoria lineages. Given the above efficacy demonstrated for intranasally administered antibodies directed against influenza A subtypes and also influenza B, and that multiple antibodies were efficacious in combination, studies were undertaken with antibody combinations. These combinations included combinations which mimic and could compare to the established trivalent and quadrivalent vaccines currently in use. Thus, in an effort to treat influenza, prevent infection, or prevent transmission, combination intranasal antibody compositions were evaluated in vivo in animal models and assessed against influenza A and influenza B viruses.

Figure 24:
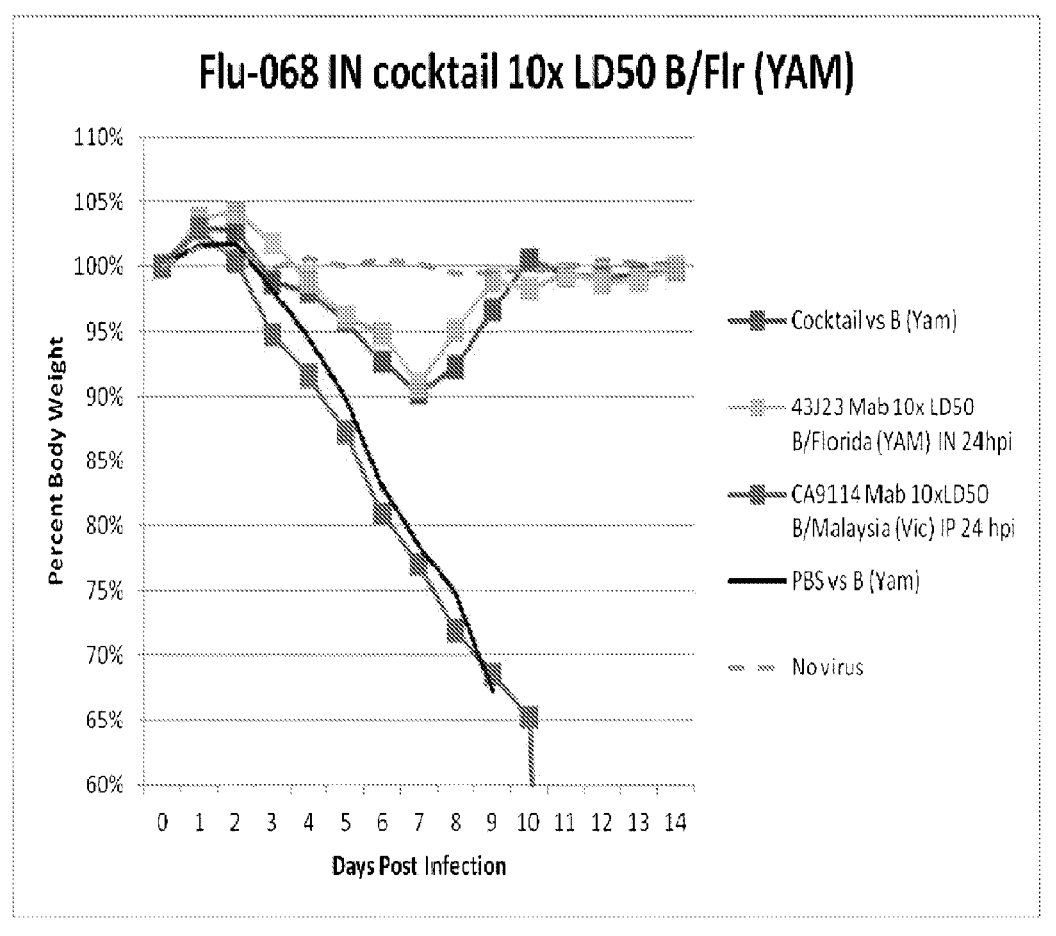
Figure 25:
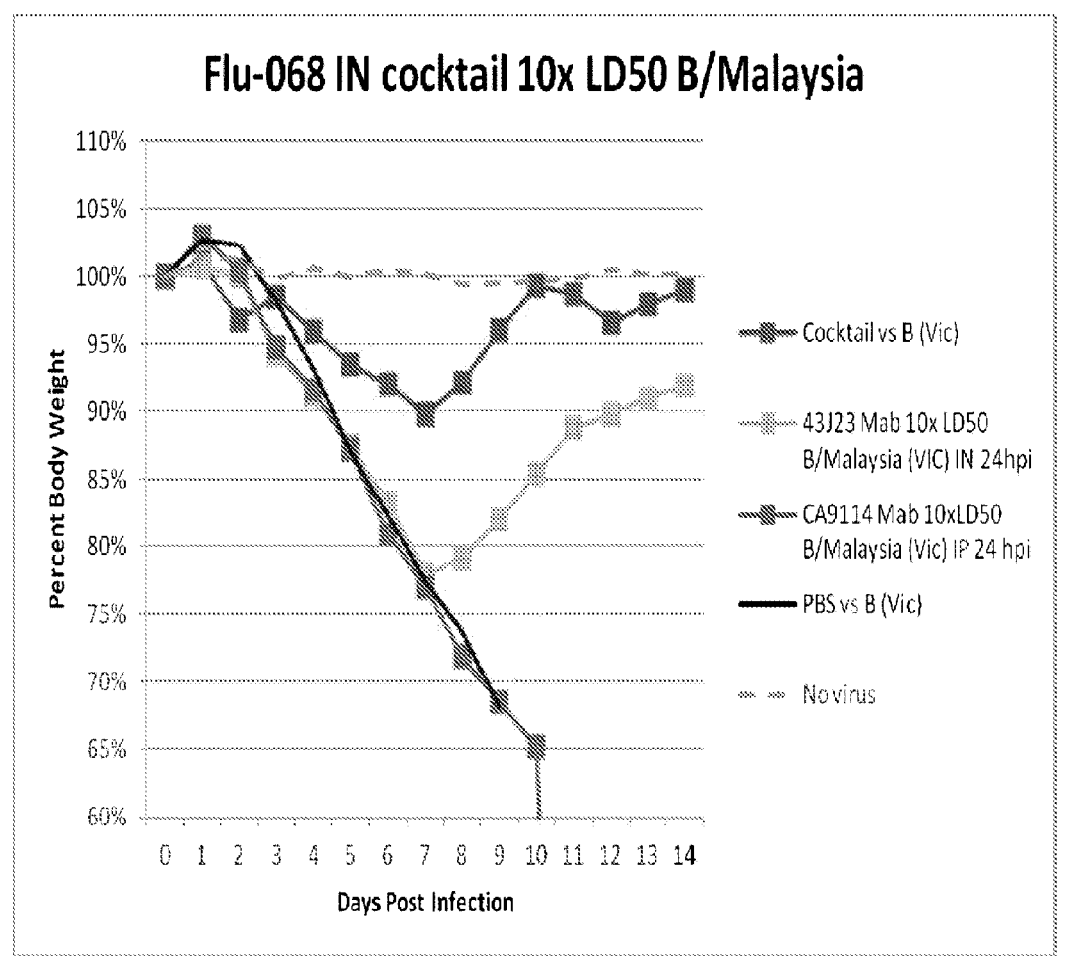
Figure 26:
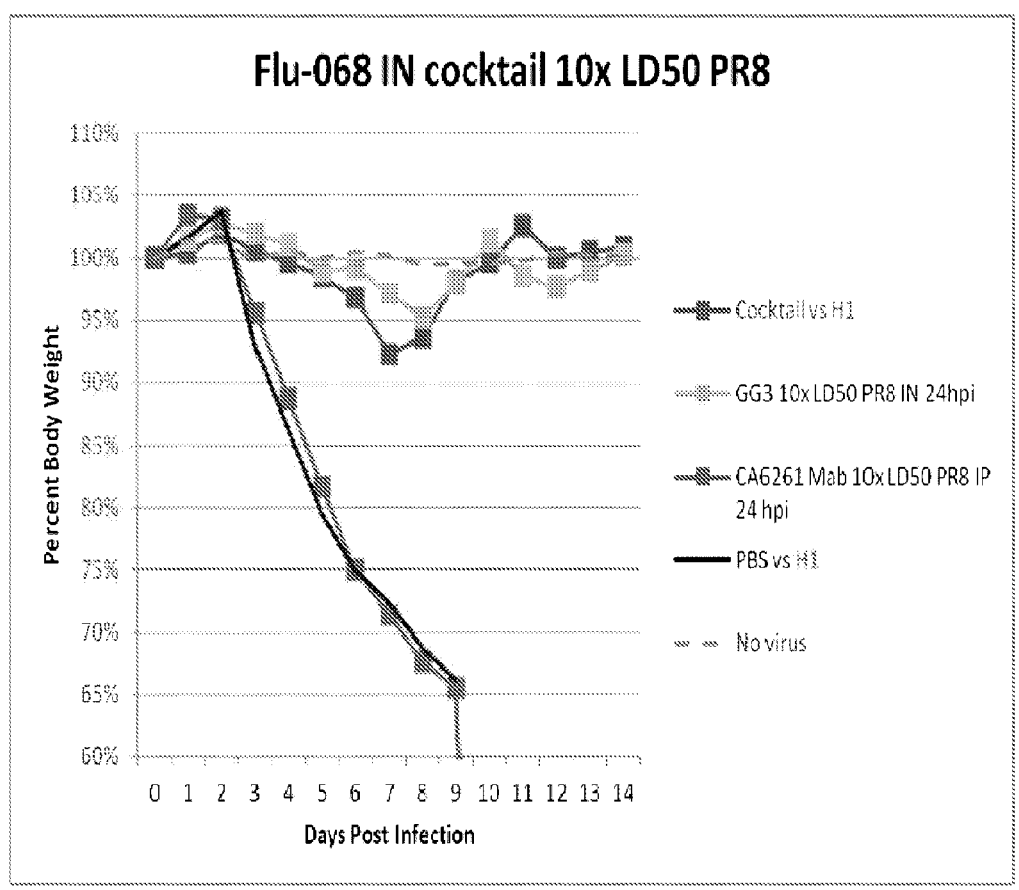
FIG. 26 depicts efficacy of antibody cocktail (H1 antibody GG3, H3 antibody CA8020 and influenza B virus antibody 43J23) administered intranasally in combination each at 1 mg/kg, with total of 3 mg/kg antibody in 50 μl, 24 hpi with influenza A H1 virus PR8. The cocktail is compared to GG3 antibody alone IN, antibody CA6261 administered IP and PBS. Animals were monitored for body weight daily for 14 days post infection and percent body weight of original day 0 weight is plotted.
Figure 27:
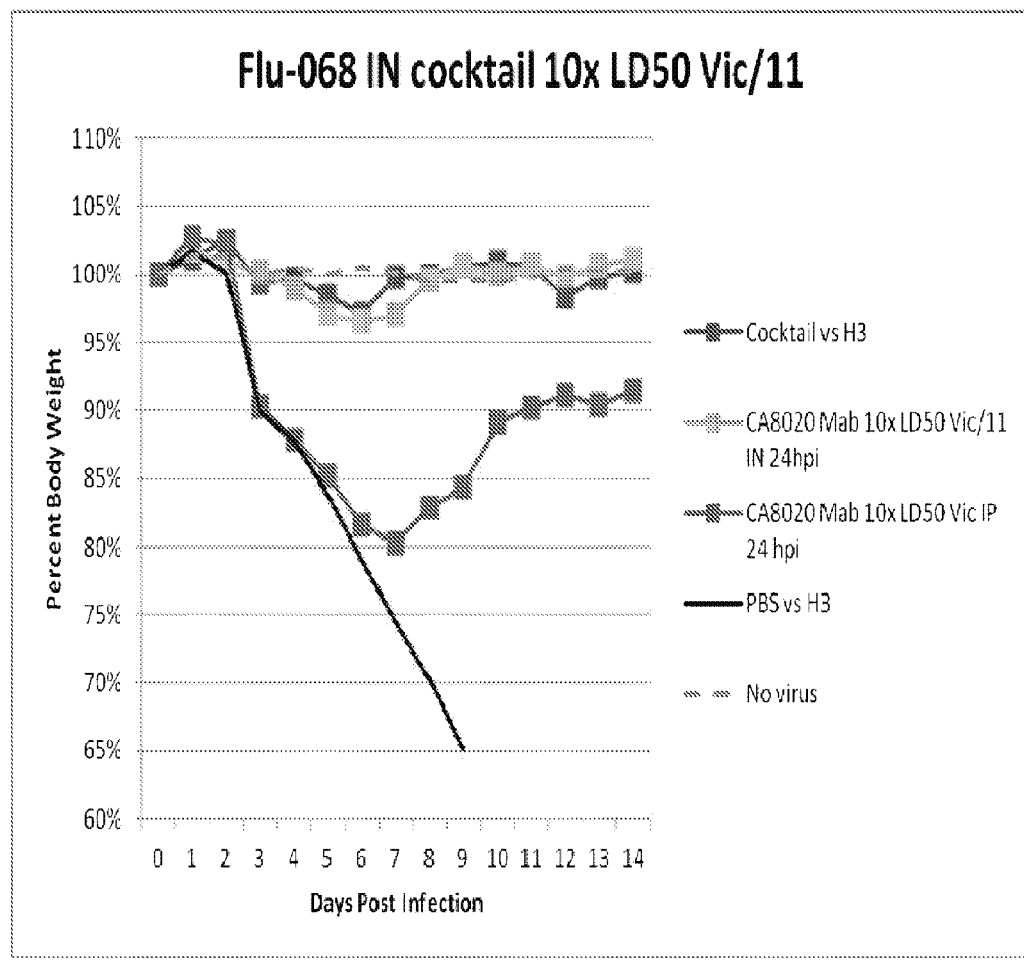
FIG. 27 provides a combination antibody cocktail study against H3 virus Vic/11. The antibodies GG3, CA8020 and 43J23 were administered 24 hpi each at 1 mg/kg in a cocktail. Animals were monitored for body weight daily for 14 days post infection and percent body weight of original day 0 weight is plotted. Antibody CA8020 administered alone at 1 mg/kg either IN or IP and PBS were compared in this study.
Figure 28:
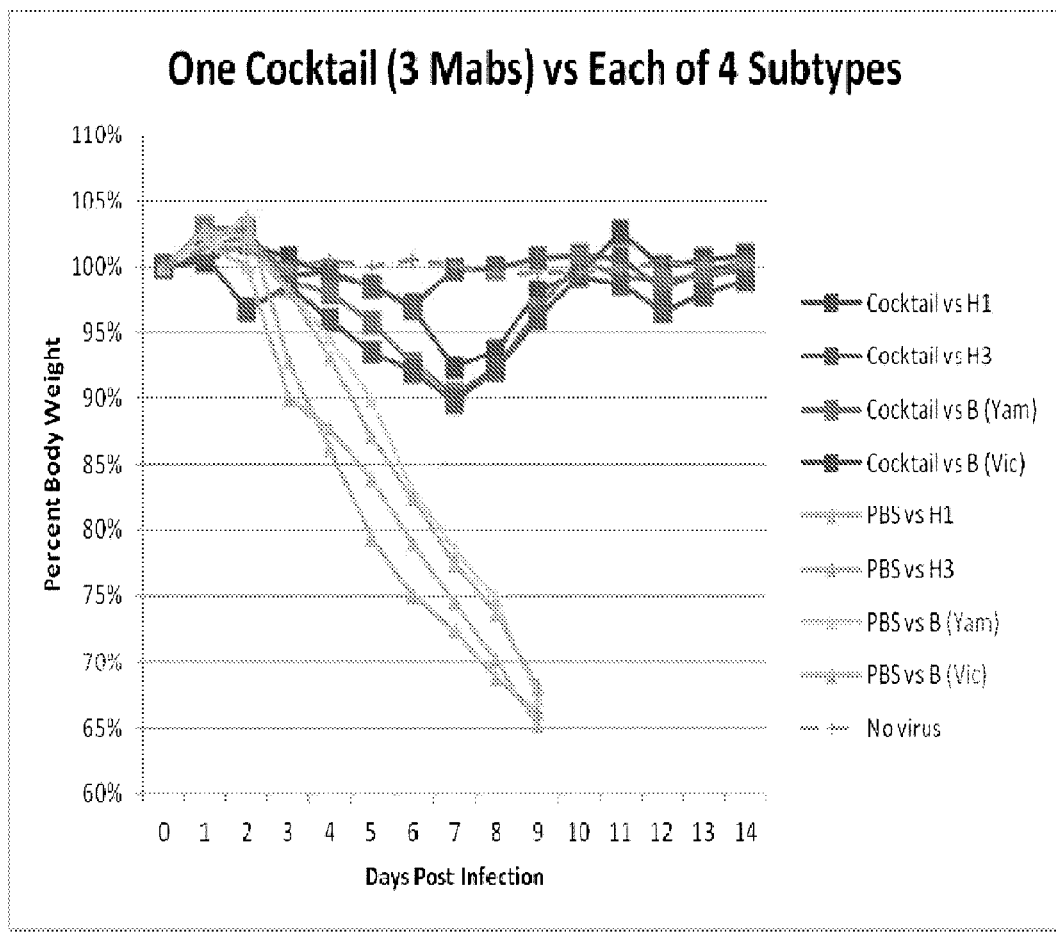
FIG. 28 shows results of a cocktail of influenza antibodies GG3, CA8020 and 43J23 administered 24 hpi (each antibody at 1 mg/kg in a cocktail total of 3 mg/kg total all antibodies) versus PBS after infection with each of an influenza A H1 subtype virus, influenza A H3 subtype virus, B(Yamagata) virus and B(Victoria) virus. Animals were monitored for body weight daily for 14 days post infection and percent body weight of original day 0 weight is plotted. The three antibody cocktail was effective against all viruses tested, particularly against each and all of H1, H3, B(Yam) and B(Vic) viruses.

A cocktail of two influenza A antibodies and an influenza B antibody, particularly antibodies 43J23 (anti-influenza B monoclonal antibody isolated by phage display), antibody GG3 (an influenza A anti-H1 antibody) and CA8020 (an influenza A anti-H3 antibody) were evaluated in combination for efficacy against infection with influenza A H1, H3 and influenza B. A cocktail of 3 mg/kg total antibody, 1 mg/kg of each of antibody 43J23, GG3 and CA8020, was administered intranasally in a 50 µl total volume 24 hours post infection (24 hpi) with influenza virus. In FIG. 24, the results of an efficacy study using the cocktail post infection with influenza B/Florida (Yamagata lineage) virus is shown. Efficacy of the cocktail against the B virus infection was comparable to efficacy of B antibody 43J23 alone at 1 mg/kg. IP administration of antibody CA9114 at 1 mg/kg did not protect the animals from B virus infection, as assessed by percent body weight. It is notable that the above examples demonstrated that the CA9114 antibody is efficacious against B virus when administered at 1 mg/kg intranasally (IN). FIG. 25 depicts the results of a similar study with the cocktail of antibody 43J23, GG3 and CA8020 against B/Malaysia virus. Establishing that the same cocktail is similarly efficacious against influenza A virus, the cocktail retained body weight in animals post infection with H1 virus (FIG. 26). Efficacy of the cocktail in this study (FIG. 26) was similar to that of anti-H1 antibody GG3 administered alone at 1 mg/kg IN. The cocktail of antibodies was similarly effective against influenza A H3 subtype virus (FIG. 27), again as effective in a cocktail versus dosing intranasally with a single anti-H1 antibody (CA8020) alone), under conditions where IP administration of CA8020 was not as effective at the same dose. FIG. 28 depicts a study of intranasal antibody cocktail (anti-B antibody 43J23, anti-A H1 antibody GG3 and anti-influenza A H3 antibody CA8020) against each of 4 subtypes of circulating influenza viruses, showing efficacy against H1, H3, B(Yamagata) and B(Victoria) in a single experiment.

Figure 29:
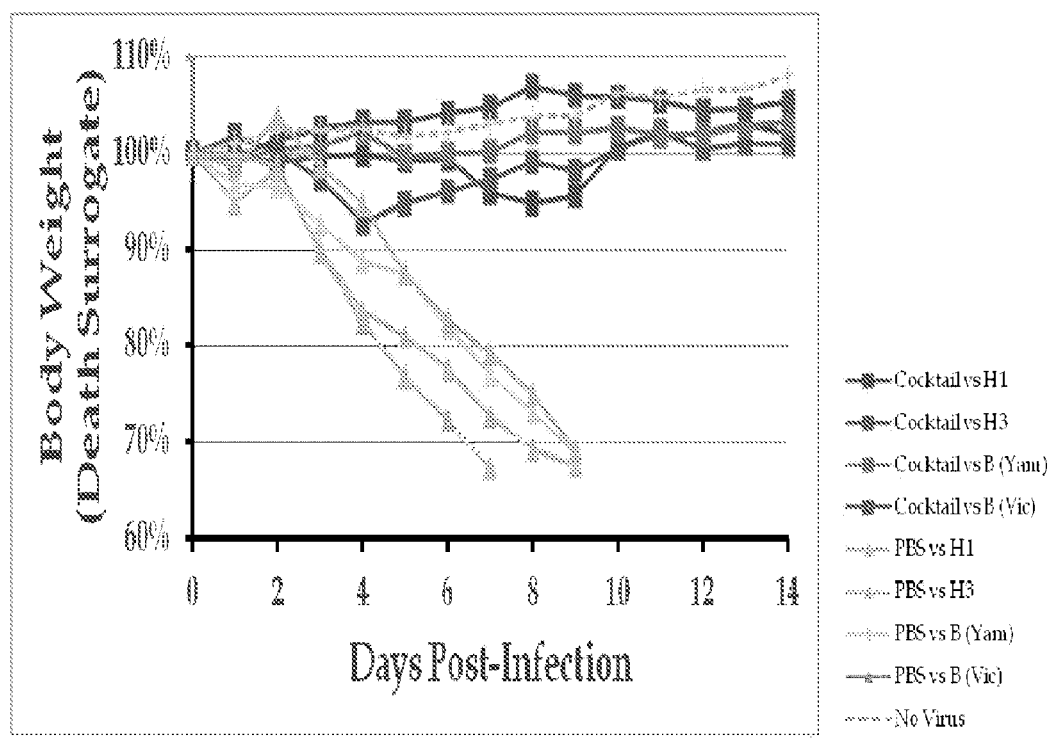
FIG. 29 depicts assessment of a cocktail of three antibodies for protection in mice from flu subtypes, using body weight as a death surrogate. Mice were treated with 10×LD50 of influenza A H1 or H3 subtypes, or influenza B virus from Yamagata or Victoria lineage and treated 24 hours later (24 hpi) with a Universal Influenza Cocktail comprised of three antibodies—antibodies 5A7, CA6261 and CA8020—at 1 mg/kg each. The three antibody cocktail was effective against infection with any viruses tested—H1, H3, B(Yam) and B(Vic) virus infection.

Another intranasal cocktail was evaluated in a comparable study using a different combination of anti-influenza B and anti-influenza A antibodies. In this study, CA8020 anti-H3 antibody was utilized in combination with anti-H1 antibody CA6261 and anti-B antibody 5A7. The 5A7 antibody was recently reported as broadly neutralizing influenza B strains isolated from 1985 to 2006 belonging to both Yamagata and Victoria lineages (Yasugi M et al (2013) PLoS Pathog 9(2): e1003150, doi: 10.1371/journal.ppat.1003150). The antibody heavy and light chain variable region as reported were cloned into IgG expression vector containing the variable regions fused to mouse IgG2a (similarly as described above and in Example 1). 1 mg/kg of each of antibodies 5A7, CA6261 and CA8020 were administered in a total 3 mg/kg antibody dose intranasally to animals 24 hours post infection with influenza virus. This cocktail was tested against H1 virus, H3 virus, B(Yamagata) and B(Victoria) lineage viruses and was efficacious against any and all of the viruses tested (FIG. 29).

EXAMPLE 10

Alternative Antibody Efficacy Against Influenza H1 and H3 Virus

Figure 30:
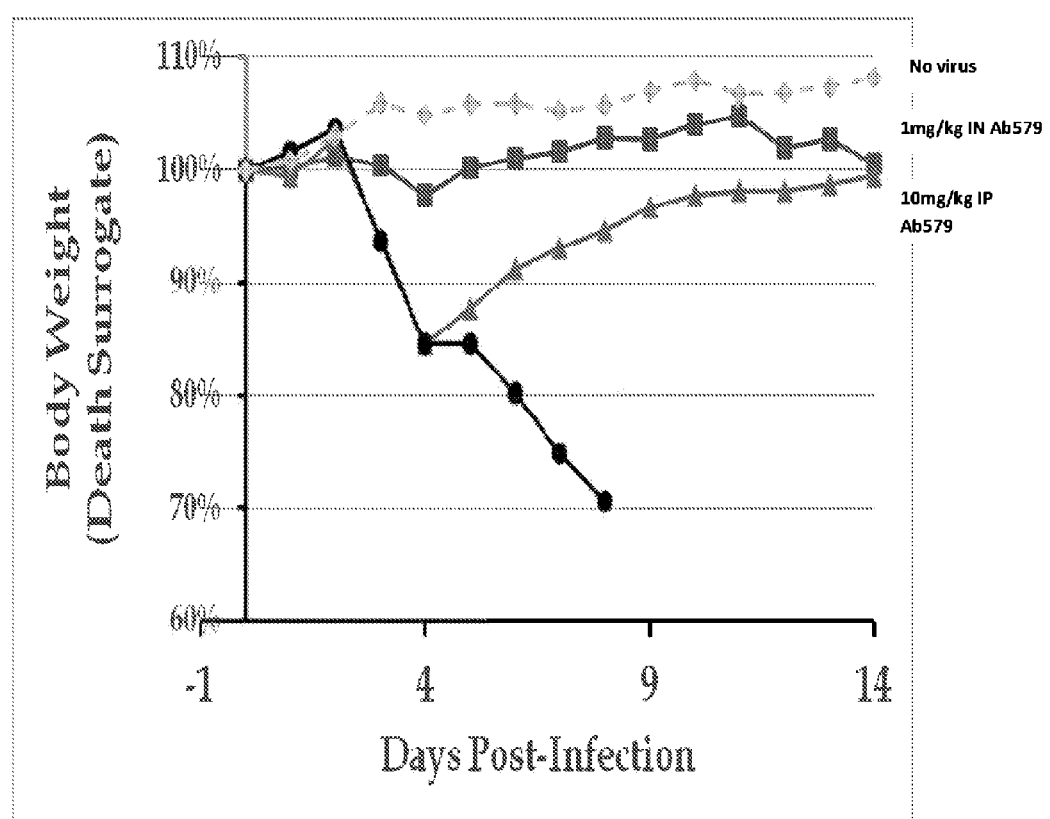
FIG. 30 depicts treatment of H3 subtype influenza virus 24 hours post infection with antibody TRL579 (Mab579). Antibody 579 was administered at 1 mg/kg IN 24 hpi or at 10 mg/kg IP 24 hours post infection with 10×LD50 of H3 Vic11 virus. Controls were PBS and no virus. Animals (5 mice per group) were monitored for body weight daily for 14 days post infection and percent body weight of original day 0 weight is plotted.
Figure 31:
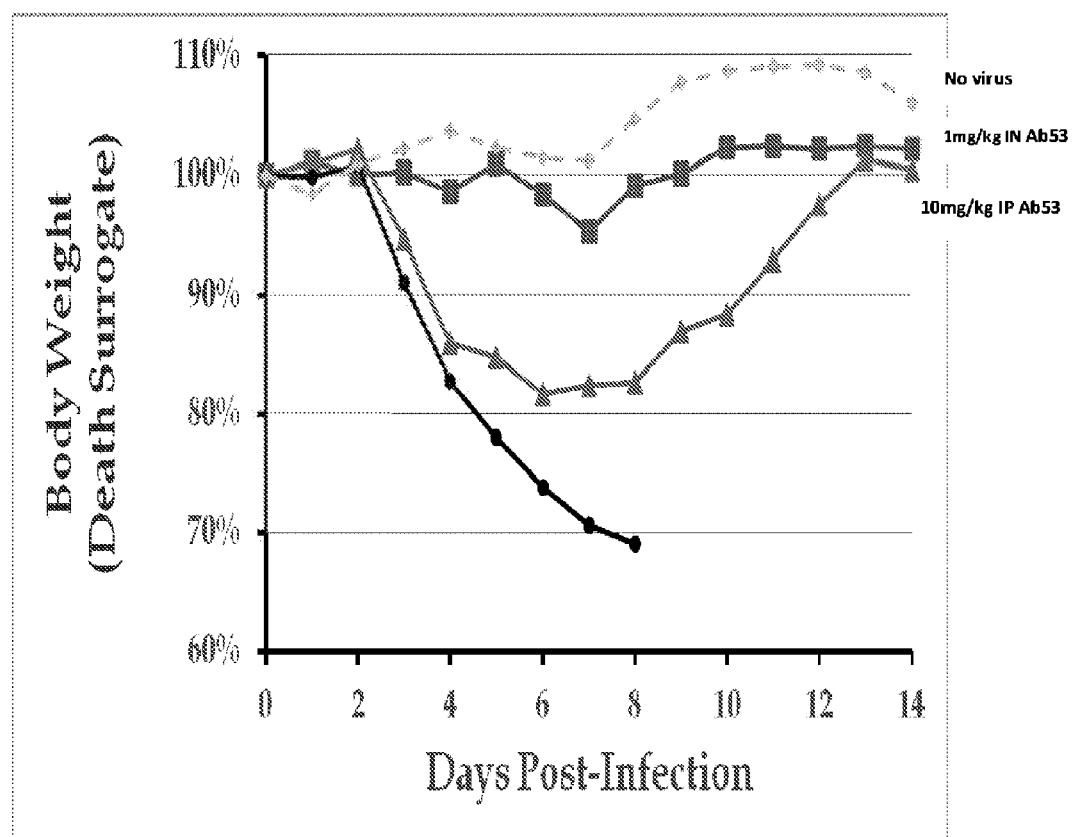
FIG. 31 depicts treatment of H1 influenza virus 24 hours post infection with antibody TRL53 (Mab53). Antibody 53 was administered at 1 mg/kg IN 24 hpi or at 10 mg/kg IP 24 hours post infection with 10×LD50 of H1 Ca109 virus. Controls were PBS and no virus. Animals (5 mice per group) were monitored for body weight daily for 14 days post infection and percent body weight of original day 0 weight is plotted.

Efficacy of administration to the airway, using intranasal administration, was assessed with additional alternative influenza antibodies. Human monoclonal antibodies have been isolated directly from human subjects that neutralize and have efficacy against both Group 1 and Group 2 influenza A viruses. The human antibody Mab53 (also denoted TRL53) is described in US2012/0020971 and WO2011/160083 and is effective in neutralizing Group 1 and 2 H1, H9, H7 and H5 subtypes. The antibody Mab579 (also denoted TRL579) is described in WO2013/086052 and is effective in neutralizing H3 and H7. The Mab579 and 53 antibodies were tested in the mouse model for therapeutic efficacy against influenza A virus infection. Mab579 was tested against H3 influenza and Mab53 was tested against H1 influenza. IN and IP dosing were compared, with IN dosing at 1 mg/kg and IP dosing tenfold higher at 10 mg/kg. Antibody Mab579 was administered 24 hours post infection (24 hpi) for treatment efficacy against 10×LD50 of H3 influenza virus Vic11 (FIG. 30). Antibody Mab53 was administered 24 hours post infection (24 hpi) for treatment efficacy against 10×LD50 of H1 influenza virus Ca109 (FIG. 31). IN administration was more effective than IP administration, even with IP administration at a 10 fold higher dose in the same experiment.

EXAMPLE 11

Prophylaxis Studies with Intranasally Administered Antibodies

Given the remarkable efficacy of intranasal administration of neutralizing antibodies after infection, studies were undertaken to evaluate efficacy of intranasal administration prophylactically and prior to infection with virus. These studies serve to assess and demonstrate the applicability of intranasal administration in instances where an individual is exposed to influenza virus and as an effective approach to prevent or reduce transmission within an exposed or at risk population, or clinically in patients where infection or illness would be an overall greater health risk. The Group 1 (H1) antibody CA6261 was evaluated for administration days prior to influenza virus infection in the mouse animal model. Administration of CA6261 was evaluated 3, 4, 5, 6, and 7 days prior to infection challenge and IN and IP dosing at different doses were directly compared.

Figure 32:
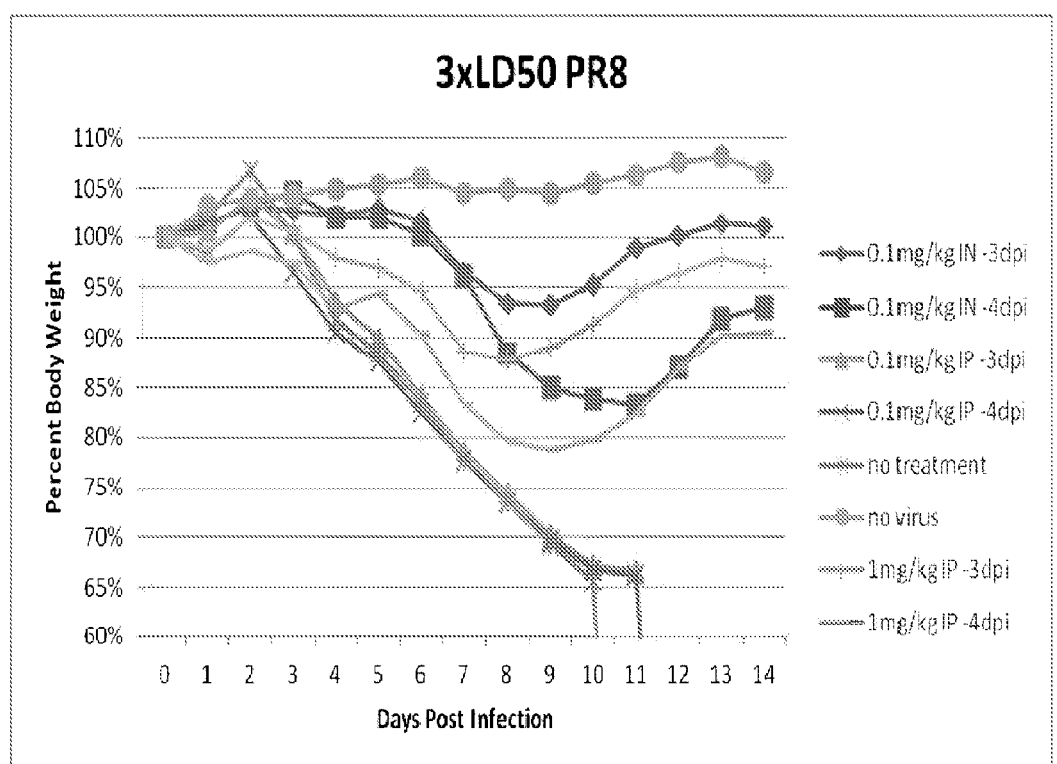
FIG. 32 depicts studies of IN and IP administration prophylactically 3 or 4 days prior to infection with virus. Antibody CA6261 was administered IN or IP 3 or 4 days before challenge with 3×LD50 of H1 influenza virus A/Puerto Rico/8/1934 (denoted PR8). CA6261 antibody was administered IN (0.1 mg/kg) or IP (0.1 mg/kg and 1 mg/kg) 3 days prior to infection (−3 dpi) or 4 days prior to infection (−4 dpi) and challenge with H1 influenza virus. Controls were no virus and no treatment. Animals were monitored for body weight daily for 14 days post infection and percent body weight of original day 0 weight is plotted.

In the first studies, antibody CA6261 was administered IN or IP and the mice were then challenged with 3×LD50 dose of H1 PR8 virus. FIG. 32 depicts studies of IN and IP administration prophylactically 3 or 4 days prior to infection with virus. Antibody CA6261 was administered IN or IP 3 or 4 days before challenge with 3×LD50 PR8. CA6261 antibody was administered IN (0.1 mg/kg) or IP (0.1 mg/kg and 1 mg/kg). IN administration up to 4 days prior to infection (−4 dpi) (assessed at 0.1 mg/kg) protected mice from virus challenge. IP administration 3 or 4 days prior to infection at the same dose (0.1 mg/kg) was completely ineffective. IP administration at 3 or 4 days pre-infection was effective at 1 mg/kg. On comparing the IN (0.1 mg/kg) and IP (1 mg/kg) administrations at −3 dpi and −4 dpi, in both instances, the tenfold lower IN dose was more effective than IP.

Figure 33:
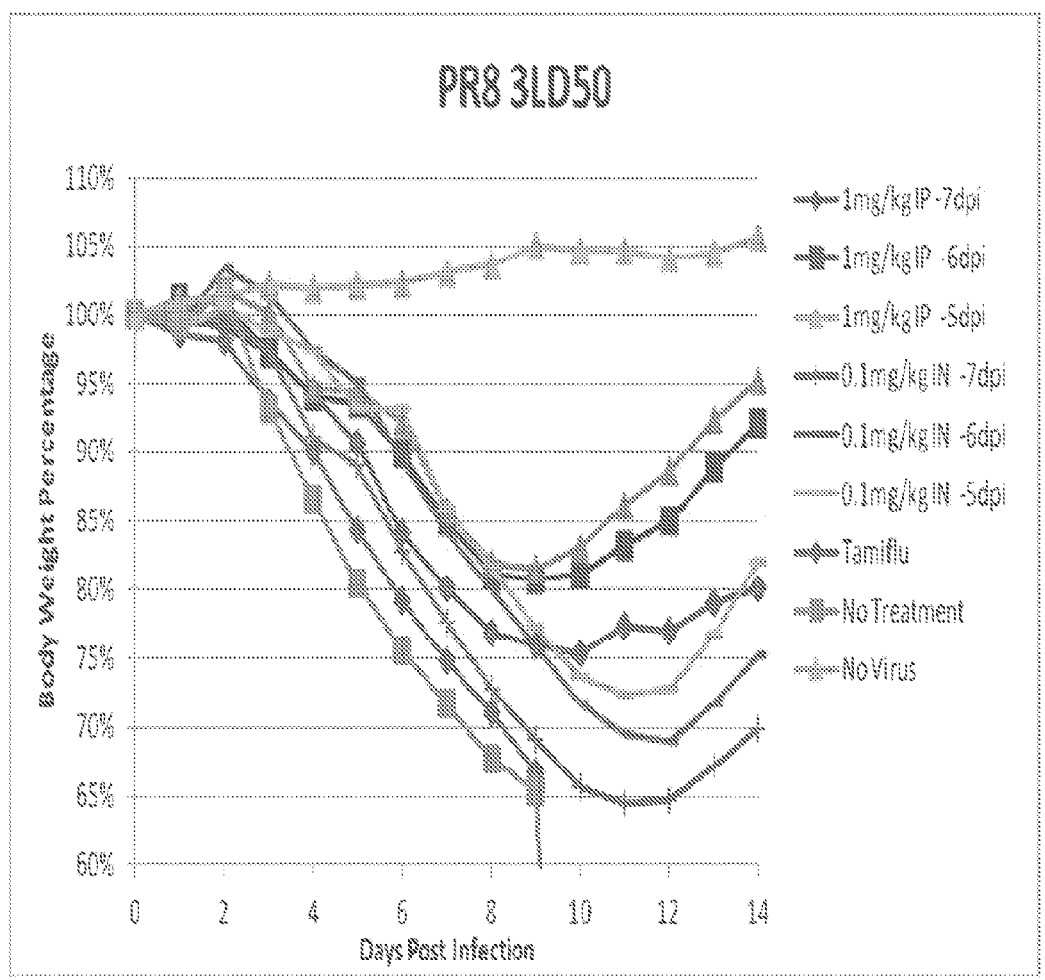
FIG. 33 depicts studies of IN and IP administration prophylactically 5, 6 or 7 days prior to infection with virus. Antibody CA6261 was administered IP (at 1 mg/kg) or IN (at 0.1 mg/kg) either 5, 6 or 7 days before challenge with 3×LD50 of H1 influenza virus PR8. Controls were Tamiflu (10 mg/kg given orally, twice a day for five days), no treatment and no virus. Animals were monitored for body weight daily for 14 days post infection and percent body weight of original day 0 weight is plotted.

Prophylactic efficacy was then evaluated 5, 6 and 7 days prior to virus infection, with the results depicted in FIG. 33. A tenfold higher dose IP was evaluated versus IN administration. Antibody CA6261 was administered IP (at 1 mg/kg) or IN (at 0.1 mg/kg) either 5, 6 or 7 days before challenge with 3×LD50 of H1 influenza virus PR8. Tamiflu administration (10 mg/kg orally, twice a day for five days) was also assessed for comparison. Efficacy was demonstrated at 0.1 mg/kg IN administration at −5 dpi. Not all mice survived with 0.1 mg/kg IN administration 6 or 7 days prior to virus challenge. The tenfold higher IP dose (10 mg/kg) was effective at 5, 6 or 7 days prior to challenge. Administration of antibody IN at 0.1 mg/kg 5 days prior to challenge was at least as effective as IP administration of a tenfold higher 1 mg/kg dose 7 days prior to challenge.

Figure 34:
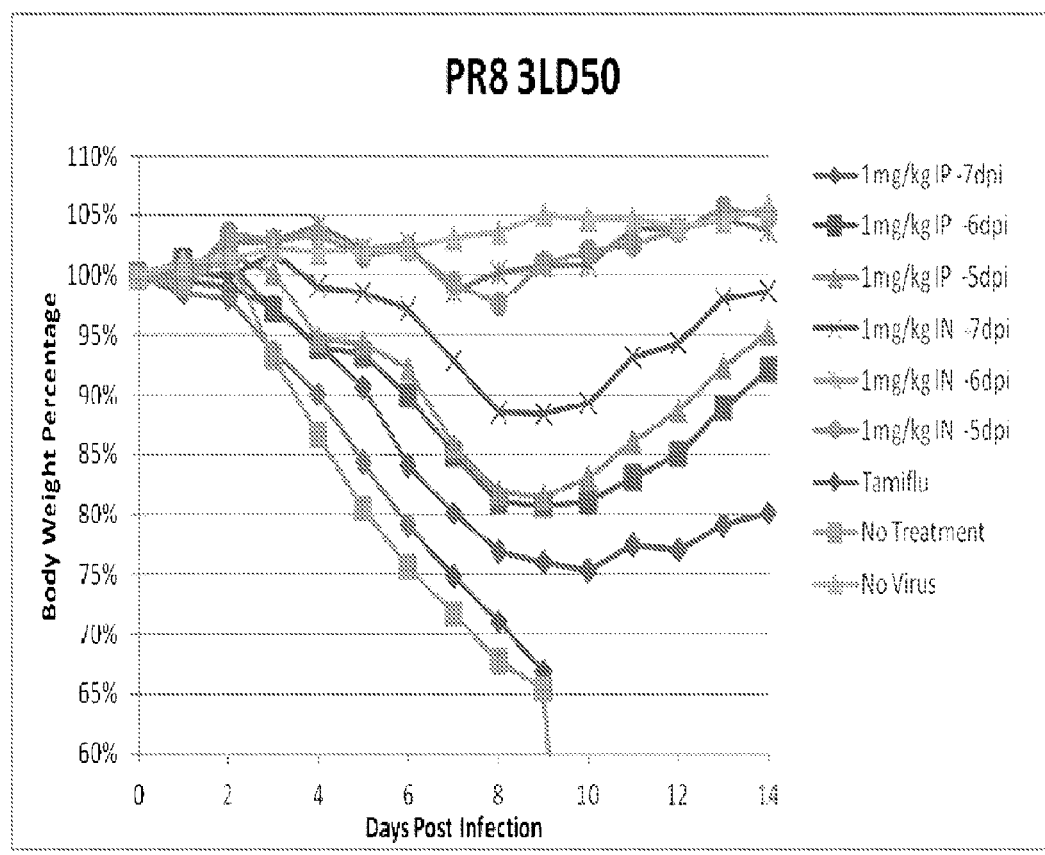
FIG. 34 depicts studies of IN and IP administration prophylactically 5, 6 or 7 days prior to infection with virus. Antibody CA6261 was administered IP (at 1 mg/kg) or IN (at 1 mg/kg) 5, 6 or 7 days before challenge with 3×LD50 of H1 influenza virus PR8. Controls were Tamiflu (10 mg/kg given orally, twice a day for five days), no treatment and no virus. Animals were monitored for body weight daily for 14 days post infection and percent body weight of original day 0 weight is plotted.

Higher IN doses at 1 mg/kg were then evaluated 5, 6 and 7 days prior to virus challenge. FIG. 34 depicts studies of IN versus IP administration with antibody CA6261 administered IP or IN at 1 mg/kg 5, 6 or 7 days before challenge with 3×LD50 virus PR8. IN administration of 1 mg/kg antibody was effective prophylactically up to 7 days prior to virus challenge, and in each instance IN was more effective than the same amount of antibody administered IP. IN fact, IN administration at any time (5, 6 or 7 days prior to challenge) was more effective than any IP administration, even if IP was administered closer to virus challenge. In all instances, antibody was more effective than Tamiflu.

The above studies demonstrate that IN administration is in fact superior to IP administration for prophylactic protection. IN administration of 0.1 mg/kg antibody is protective against challenge (3×LD50) up to 5 days pre-infection (−5 dpi). The same dose 0.1 mg/kg administered IP at any of 3-7 days before virus infection does not protect animal (against the same 3×LD50 dose of virus). At higher doses of IN administered antibody (1 mg/kg was evaluated), IN administered antibody can protect against challenge if administered at least up to 7 days in advance. IN administration more than 7 days in advance was not evaluated but may be efficacious.

Further, multiple dosing by IN administration prior to challenge is predicted to be potentially more efficacious (see above examples and FIG. 11). As shown in FIG. 11, repeated dosing post infection is efficacious and lower doses intranasally are effective when multi-dosed hours apart (8 hours, 32 hours, 52 hours). Similarly, repeated dosing prior to virus infection or exposure is predicted to be effective and may permit lower IN prophylactic dosing.

Figure 35:
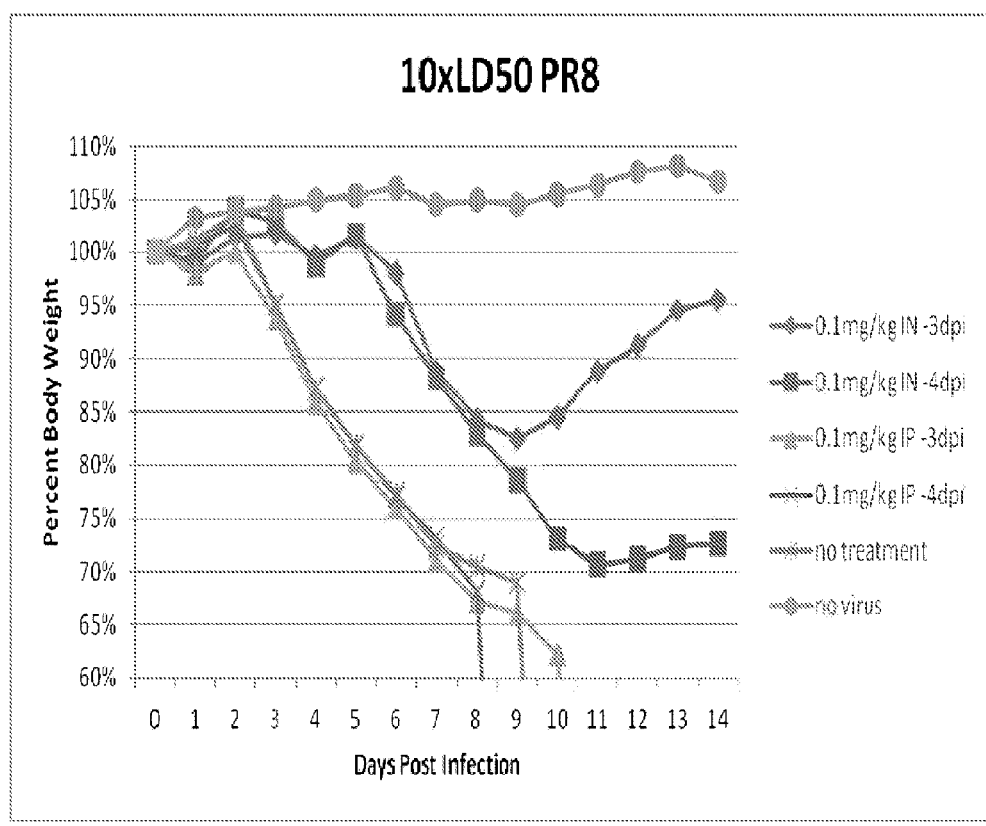
FIG. 35 depicts studies of IN and IP administration prophylactically 3 or 4 days prior to infection with virus, with virus challenge at higher dose of 10×LD50. Antibody CA6261 was administered IN or IP at 0.1 mg/kg 3 or 4 days before challenge with 10×LD50 of H1 virus PR8. Controls were no virus and no treatment. Animals were monitored for body weight daily for 14 days post infection and percent body weight of original day 0 weight is plotted.

Prophylactic efficacy was evaluated at higher doses of virus challenge, particularly administering the CA2621 antibody days before challenging with 10×LD50 of H1 virus PR8. Three and four days before challenge with 10×LD50 of PR8 H1 subtype virus, animals were administered 0.1 mg/kg CA6261 antibody either IN or IP (FIG. 35). IP administration of 0.1 mg/kg antibody 3 or 4 days before virus challenge was completely ineffective, with the IP treated animals succumbing to virus infections similar to animals who received no treatment. In contrast, animals administered 0.1 mg/kg antibody intranasally either 3 or 4 days prior to high titer virus challenge were protected from infection.

Figure 36:
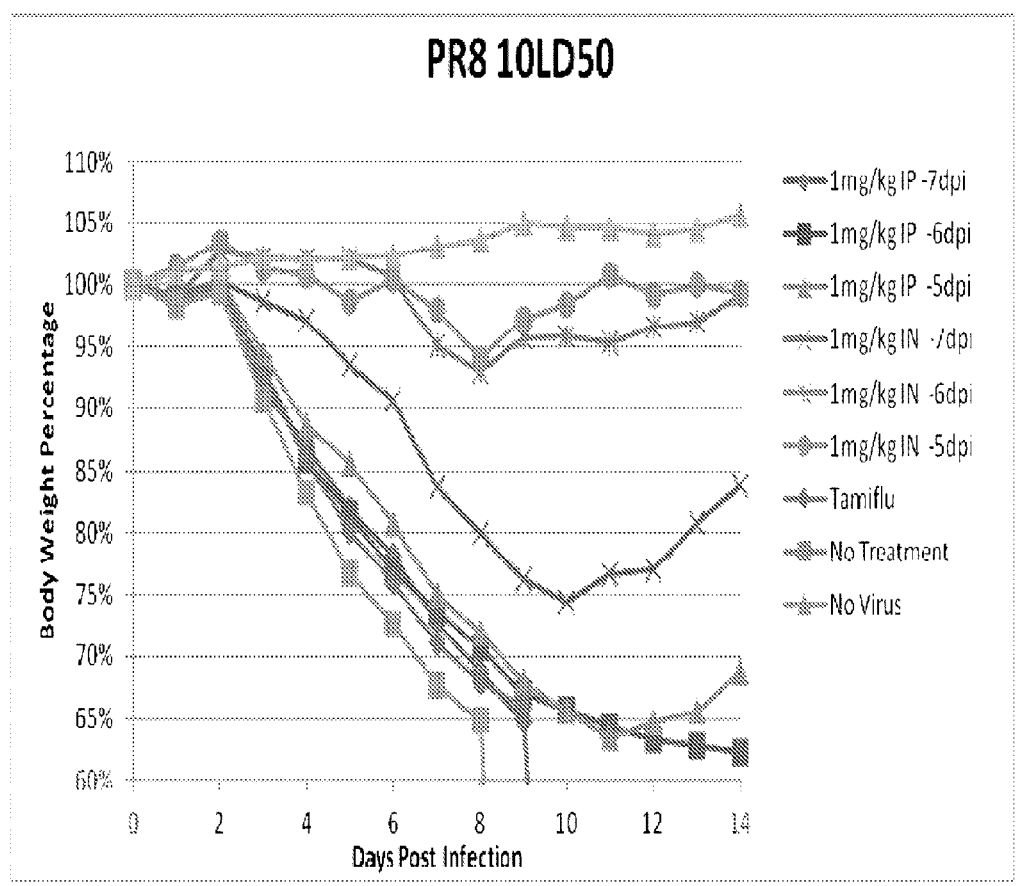
FIG. 36 depicts studies of IN and IP administration prophylactically 5, 6 or 7 days prior to infection with virus, with virus challenge at higher dose of 10×LD50. Antibody CA6261 was administered IP (at 1 mg/kg) or IN (at 1 mg/kg) 5, 6 or 7 days before challenge with 10×LD50 of H1 influenza virus PR8. Controls were Tamiflu (10 mg/kg given orally, twice a day for five days), no treatment and no virus. Animals were monitored for body weight daily for 14 days post infection and percent body weight of original day 0 weight is plotted.

Antibody administration 5, 6 and 7 days prior to high titer challenge was evaluated, with antibody administered at 1 mg/kg either IN or IP (FIG. 36). In this study, only animals administered antibody to the airway (via intranasal administration) completely survived virus challenge. Mice treated with 1 mg/kg of antibody administered 5, 6 or 7 days prior to virus challenge were not fully protected and mice died from the infection. Tamiflu was completely ineffective in protection. Mice treated with 0.1 mg/kg antibody intranasally either 5 or 6 days prior to virus infection survived virus challenge nearly as well as control animals that were not infected.

Thus, intranasal administration of anti-influenza antibodies is an effective protocol and method for prophylaxis against antibody infection. Influenza neutralizing antibody administered intranasally at least up to 7 days prior to virus infection was protective against virus challenge. Protection via intranasal administration at least as much as 7 days in advance was demonstrated for high titer virus, higher even than might be reasonably expected to represent a human's exposure to virus. Thus, the level of protection observed in these studies indicates that intranasal antibody administration will be effective in a human subject to protect against virus challenge and to block or reduce virus transmission. Intranasally administered antibody is protective under conditions and in instances where IP administration is ineffective.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for treatment or prophylaxis of influenza viral infection in a mammal exposed to or at risk of exposure to influenza virus or manifesting clinical symptoms of respiratory virus infection comprising administering intranasally (IN) or via inhalation to said mammal an effective amount of two or more monoclonal IgG antibodies capable of neutralizing influenza A virus of at least two HA subtypes, wherein the two or more antibodies are administered in a single unit dose of 1 mg/kg or less, with one or more doses being administered, wherein, when administered, multiple doses are administered at spaced apart intervals.

2. The method of claim 1 wherein the two or more antibodies comprise an antibody capable of neutralizing influenza A HI virus, an antibody capable of neutralizing influenza A H3 virus, and further comprise an antibody capable of neutralizing influenza B virus including Yamagata and/or Victoria lineage.

3. The method of claim 1 wherein each of the two or more antibodies is administered in a time period selected from the group consisting of (i) up to 24 hours post infection; (ii) up to 48 hours post infection and (iii) up to 72 hours post infection.

4. The method of claim 1 wherein the two or more antibodies are administered in one or more doses before infection or exposure to virus or before clinical manifestation of virus illness or symptoms associated therewith.

5. The method of claim 1 wherein the two or more antibodies are administered in a single dose of less than 0.5 mg/kg.

6. The method of claim 1 wherein the two or more antibodies are administered each in a single dose of less than 0.1 mg/kg.

7. The method of claim 1 wherein the two or more antibodies are administered each in a single dose of less than 0.05 mg/kg.

8. The method of claim 1 wherein two or more antibodies are administered intranasally or via inhalation in multiple doses of less than 1 mg/kg per dose, wherein the multiple doses are administered at least 2 hours apart and first administered up to 72 hours after presumed infection, exposure or manifestation of clinical symptoms.

9. The method of claim 1 further comprising additional administration intraperitoneally (IP) or intravenously (IV) of at least one virus specific monoclonal antibody wherein the antibody additionally administered is a neutralizing or non-neutralizing antibody and is the same as or different from at least one of the antibodies administered intranasally or by inhalation.

10. A protocol for administration of monoclonal antibody against influenza virus comprising administering an effective amount of at least two influenza virus neutralizing IgG antibodies intranasally or by inhalation, combined with administering at least one anti-influenza antibody intraperitoneally or intravenously, wherein the at least two antibodies administered by inhalation or intranasally are administered at a first dose of 1 mg/kg or less and the at least one antibody administered intraperitoneally or intravenously is administered at a second dose of 1 mg/kg or greater and is the same or a different at least one antibody as one or more of the at least two antibodies administered intranasally or by inhalation.

11. The protocol of claim 10 wherein the at least one antibody administered intraperitoneally or intravenously is a non-neutralizing antibody.

12. The protocol of claim 10 wherein the at least two antibodies administered intranasally or by inhalation are administered at a dose less than I mg/kg and the at least one antibody administered intraperitoneally or intravenously is administered at a dose at least 5 mg/kg.

13. The protocol of claim 10 wherein the intranasal or inhalation dose is less than 1 mg/kg and the IP or IV dose is at least 10-fold higher in mg/kg than the intranasal or inhalation dose.

14. The protocol of claim 10 wherein the intranasal or inhalation dose is less than 0.5 mg/kg and the IP or IV dose is at least 5 mg/kg.

15. The protocol of claim 10 wherein the intranasal or inhalation dose is less than I mg/kg and is administered within 24 hours after presumed infection, exposure or manifestation of clinical symptoms.

16. The protocol of claim 10 wherein the intranasal or inhalation dose is less than 1 mg/kg and is administered within 48 hours after presumed infection, exposure or manifestation of clinical symptoms.

* * * * *